United States Patent
Nicolaou et al.

(10) Patent No.: US 6,252,094 B1
(45) Date of Patent: Jun. 26, 2001

(54) CHEMICAL SWITCHING OF TAXO-DITERPENOIDS BETWEEN LOW SOLUBILITY ACTIVE FORMS AND HIGH SOLUBILITY INACTIVE FORMS

(75) Inventors: K. C. Nicolaou, La Jolla, CA (US); Wolfgang Wrasidlo, Berlin (DE); Rodney K. Guy, Alameda, CA (US); Emmanuel Pitsinos, Strosbourg (FR)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/750,638

(22) PCT Filed: Jan. 10, 1995

(86) PCT No.: PCT/US95/00481

§ 371 Date: Feb. 4, 1999

§ 102(e) Date: Feb. 4, 1999

(87) PCT Pub. No.: WO95/18798

PCT Pub. Date: Jul. 13, 1995

Related U.S. Application Data

(63) Continuation of application No. 08/180,135, filed on Jan. 11, 1994, now abandoned.

(51) Int. Cl.$^7$ ................................................. C07D 305/14
(52) U.S. Cl. ............................................ 549/510; 549/511
(58) Field of Search ..................................... 549/510, 511

(56) References Cited

U.S. PATENT DOCUMENTS

| | | | |
|---|---|---|---|
| 4,960,790 | 10/1990 | Stella et al. | 514/449 |
| 5,274,137 | 12/1993 | Nicolaou et al. | 549/510 |
| 5,422,364 | 6/1995 | Nicolaou et al. | 514/449 |
| 5,440,057 | 8/1995 | Nicolaou et al. | 549/511 |
| 5,461,169 | 10/1995 | Nicolaou et al. | 549/510 |
| 5,481,007 | 1/1996 | Nicolaou et al. | 549/229 |
| 5,504,222 | 4/1996 | Nicolaou et al. | 549/511 |
| 5,608,087 | 3/1997 | Nicolaou et al. | 549/510 |
| 5,750,691 | 5/1998 | Nicolaou et al. | 544/238 |
| 5,760,240 | 6/1998 | NIcolaou et al. | 546/347 |
| 5,786,489 | 7/1998 | Nicolaou et al. | 549/229 |
| 5,817,840 | 10/1998 | Nicolaou et al. | 549/510 |
| 6,043,382 | 3/2000 | Nicolaou et al. | 549/510 |

FOREIGN PATENT DOCUMENTS

| | | |
|---|---|---|
| 0 473 326 A1 | 8/1991 | (EP) . |
| 0473326 | 3/1992 | (EP) . |
| WO 89/08453 | 9/1989 | (WO) . |
| WO 94/05282 | 9/1993 | (WO) . |

OTHER PUBLICATIONS

Deutsch, et al., "Synthesis of Congeners and Prodrugs. 3. Water Soluble Prodrugs of Taxol with Potent Antitumor Activity", *J. Med. Chem.* 32: 788–782 (1989).

Zhao, et al., "Modified Taxols. 6 . Preparation of Water–Soluble Prodrugs of Taxol", *J. Nat. Prod.* 54: 1607–1611 (1991).

Mathew, et al., "Synthesis and Evaluation of Some Water–Soluble Prodrugs and Derivatives with Antitumor Activity", *J. Med. Chem.* 35: 145–151 (1992).

Nicolaou, et al., "Design, Synthesis and Biological Activity of Protaxols", *Nature* 364: 464–466 (1993).

Paloma, et al., "Conformation of a Water–Soluble Derivative of Taxol in Water by 2D–NMR Spectroscopy", *Chem. Biol. 1*: 107–112 (1994).

Nicolaou, et al., "A Water–Soluble Prodrug of Taxol with Self–Assembling Properties", *Angew. Chem. Int. Ed. Eng. 33*: 1538–1587 (1994).

Mukaiyama, "New Synthetic Reactions Based on the Onium Salts of Aza–Arenes", *Angew. Chem. Int. Ed. Eng. 18*: 707–721 (1979).

*Primary Examiner*—Ba K. Trinh
(74) *Attorney, Agent, or Firm*—Donald G. Lewis

(57) ABSTRACT

Cyclic chemical switching method is employed for solubilizing and desolubilizing taxo-diterpenoids with respect to aqueous solvents. 2-Halogenated onium salts of aza-arenes are employed to derivatize taxo-diterpenoids so as to alter their solubility in aqueous solvents. The onium salt of aza-arene includes a delocalized charge which imparts polarity and aqueous solubility to taxo-diterpenoid derivatives. Solubilization is achieved in a one step derivatization with the onium salt of 2-halogenated aza-arenes. Desolubilization is achieved by contacting onium salts of taxo-diterpenoid-$C^n$,2-O-aza-arenes with serum protein to displace the 2-O-aza-arene and form a soluble protein:taxo-diterpenoid intermediate. This protein:taxo-diterpenoid intermediate then dissociates over time to provide a bioactive taxo-diterpenoid. These same onium salts of taxo-diterpenoid-$C^n$,2-O-aza-arenes are employed as water soluble prodrugs. The toxicity of the activated form is comparable or greater than underivatized taxol. The invention is applicable to taxol and taxol memetics having hydroxyls that are reactive with onium salts of 2-halogenated-aza-arenes.

8 Claims, 5 Drawing Sheets

Figure 1:
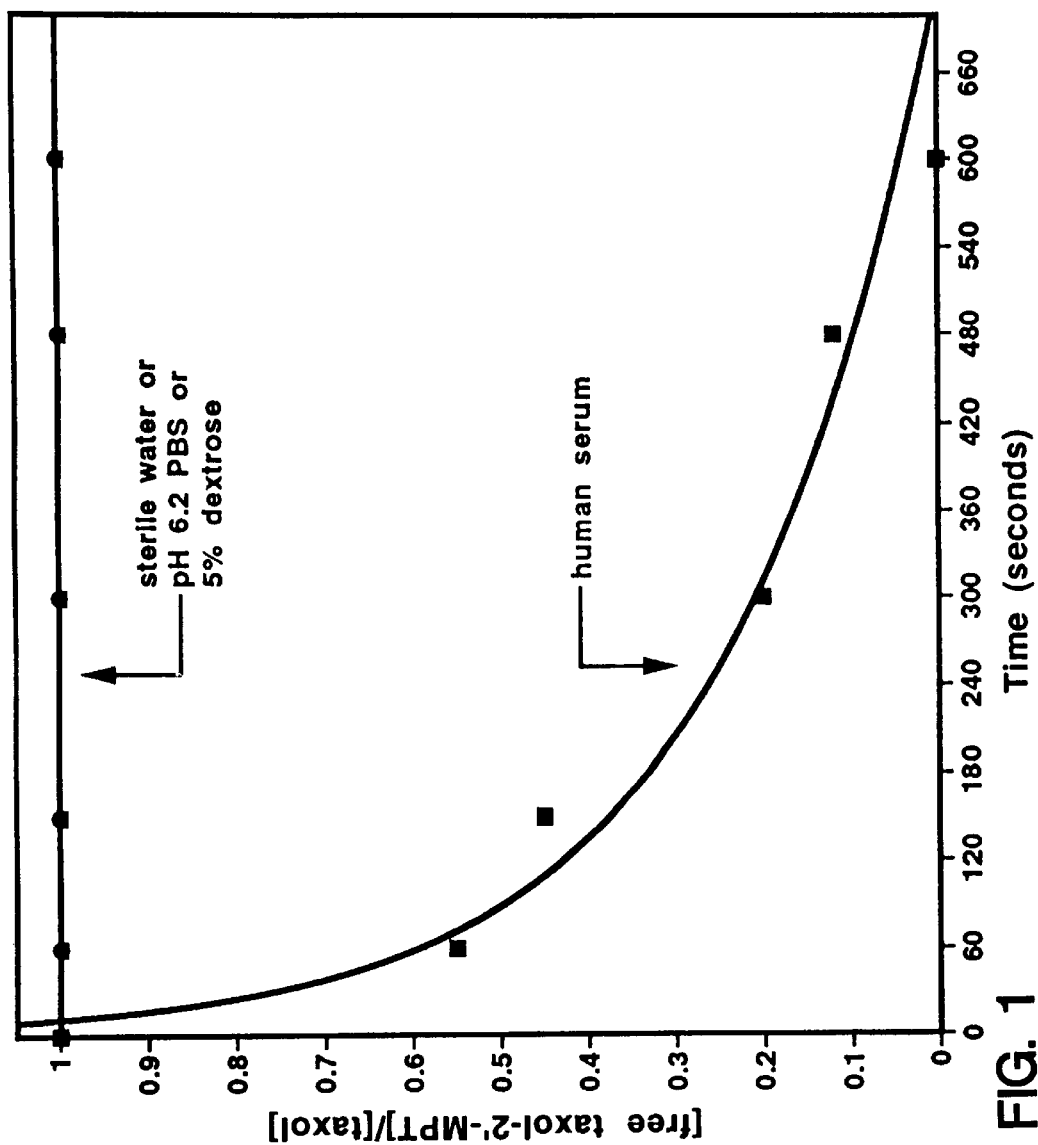

CHEMICAL SWITCHING OF TAXO-DITERPENOIDS BETWEEN LOW SOLUBILITY ACTIVE FORMS AND HIGH SOLUBILITY INACTIVE FORMS

DESCRIPTION

This is a 371 of PCT/US95/00481, filed on Jan. 10, 1995 which is a continuation of U.S. Pat. No. 08/180,135 filed Jan. 11, 1994, now abandoned.

This invention was made with government support under Contract No. CA 46446 by the National Institutes of Health. The government has certain rights in the invention.

TECHNICAL FIELD

The invention relates to taxol prodrugs. More particularly, the invention relates to a method employing derivatization with onium salts of 2-halogenated aza-arenes for chemically switching between low solubility active forms and high solubility inactive forms of taxol and taxol memetics.

BACKGROUND

Taxol, an antineoplastic agent originally isolated from Taxus brevifolia, is approved for usage in the treatment of ovarian cancer and is expected to see usage in breast, lung, and skin cancers as well. However, since Taxol possesses an extremely low water solubility, i.e., less than $1.5 \times 10^{-6}$ molar, it has been necessary to formulate Taxol in a mixture of Cremaphor™, a polyoxyethylated castor oil, and ethanol in order to achieve a therapeutic concentration. This formulation can induce a variety of significant side effects including hypersensitivity reactions.

While premedication and slow administration of the drug can circumvent these problems in the clinic, the entire protocol is quite cumbersome and requires extensive close monitoring of patients. Although taxol's dramatic efficacy has driven clinical usage forward despite these problems, a water soluble form of taxol could completely obviate the need for this troublesome protocol.

One approach to bypassing these formulation difficulties, previously attempted by several groups including our own, is the introduction of solubilizing functionality that normal metabolic pathways could remove in vivo. Compounds of this type, termed prodrugs, consist, in the case of taxol, primarily of ester derivatives at the 2' and 7 positions. Currently none of these protaxols have given success in the clinic. In each case, the prodrug is rapidly cleared from circulation by the kidneys.

Taxol is only one of a class of taxo-diterpenoids having bioactivity. Another preferred taxo-diterpenoid having clinically significant activity is Taxotere™. Unfortunately, all known bioactive taxo-diterpenoids have a low aqueous solubility.

What is needed is a method for chemically switching taxol and other taxo-diterpenoids between a high solubility and low solubility form in a manner which regulates its rate of clearance from circulation so that the prodrug is retained for a clinically significant period after administration.

Taxol itself is known to serve as a chemical switch with respect to tubulin. Binding of taxol to tubulin prevents its polymerization and the formation of microtubules. While unpolymerized tubulin is soluble in aqueous media, polymerization of tubulin leads to the formation of insoluble microtubules. Accordingly, the addition or removal of taxol drives the depolymerization or polymerization of tubulin and, in this manner, serves as a chemical switch for regulating the solubility of tubulin.

SUMMARY

The invention is a cyclic method employing chemical switching for solubilizing and desolubilizing taxo-diterpenoids with respect to aqueous solvents. The invention employs 2-halogenated onium salts of aza-arenes to derivatize taxo-diterpenoids so as to alter their solubility in aqueous solvents. The onium salt of aza-arene includes a delocalized charge which imparts polarity and aqueous solubility to taxo-diterpenoid derivatives. Solubilization includes a one step derivatization with the onium salt of 2-halogenated aza-arenes. Contacting onium salts of taxo-diterpenoid-$C^n$, 2-O-aza-arenes with the serum protein, causes the displacement of 2-O-aza-arene and the formation of a soluble protein:taxo-diterpenoid intermediate. This protein:taxo-diterpenoid intermediate then dissociates over time to provide a bioactive taxo-diterpenoid. Preferred taxo-diterpenoids include taxol, C-2 substituted analogs of taxol, and Taxotere™. Taxo-diterpenoid-$C^n$,2-O-aza-arene may be produced in a one step synthesis by reacting onium salts of 2-halogenated aza-arenes with reactive hydroxyls on the taxo-diterpenoid. Reactive hydroxyls on taxol and Taxotere™ are located at $C^{2'}$ and $C^7$. A preferred onium salt of 2-halogenated aza-arene is 2-fluoro-1-methylpyridinium tosylate. Other employable onium salts of 2-halogenated aza-arenes are disclosed by T. Mukaiyama, *Angewandte Chemie* 1979,18(18), 707–808, incorporated herein by reference.

More particularly, a first embodiment of the invention is directed a cyclic method employing chemical switching for solubilizing and desolubilizing taxo-diterpenoids with respect to aqueous solvents. Underivatized forms of the taxo-diterpenoid have low aqueous solubility and include a reactive $C^n$-hydroxyl, i.e., a reactive hydroxyl at the $C^n$ position. Preferred reactive $C^n$ hydroxyls for taxol and Taxotere™ are located at positions $C^{2'}$ and $C^7$. The method includes two steps. In the first step, the underivatized form of the taxo-diterpenoid is converted from low solubility to high solubility by derivatizing the reactive $C^n$-hydroxyl with the onium salt of the 2-halogenated aza-arene to form the onium salt of a taxo-diterpenoid-$C^n$,2-O-aza-arene derivative having high solubility. In the second step, the onium salt of the taxo-diterpenoid-$C^n$,2-O-aza-arene derivative is converted from high solubility to low solubility by contacting the taxo-diterpenoid-$C^n$,2-O-aza-arene derivative with serum protein for displacing the 2-O-aza-arene and forming a protein:taxo-diterpenoid intermediate. The protein:taxo-diterpenoid intermediate has a high solubility but then dissociates over time to produce the underviatized form of the taxo-diterpenoid employed in the first step, i.e., the taxo-diterpenoid is released from the protein:taxo-diterpenoid intermediate. The precise nature of the bonding between serum protein and the taxo-diterpenoid within the protein:taxo-diterpenoid intermediate has not been characterized, but can be stable over a period ranging from minutes to hours. A first alternative embodiment of the invention are directed to the derivatization of taxo-diterpenoids with onium salts of 2-halogenated aza-arenes. A second alternative embodiment is directed to conversion of onium salts of taxo-diterpenoid-$C^n$,2-O-aza-arene derivatives to protein:taxo-diterpenoid intermediates using serum protein. In this second alternative embodiment, the taxo-diterpenoid-$C^n$,2-O-aza-arene derivative is contacted with serum protein for displacing the 2-O-aza-arene and forming the protein:taxo-diterpenoid intermediate.

In a preferred embodiment, the taxo-diterpenoid-2-O-aza-arenes are represented by the following formula:

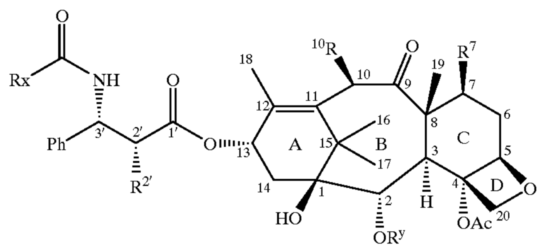

wherein $R^x$ is Ph or tBuO; $R^{10}$ is OAc or OH; RY is a C-2 substituent defined below; and $R^{2'}$ and $R^7$ are each selected from the group consisting of OH and an onium salt of a 2-O-aza-arene, with the proviso that at least one of $R^{2'}$ and $R^7$ is the onium salt of the 2-O-aza-arene. The onium salt of the 2-O-aza-arene can be represented by either of the following formulas for onium salt I or onium salt II:

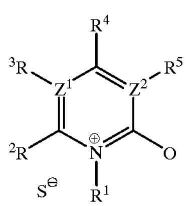

onium salt I 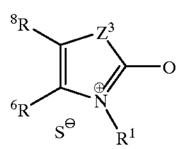 onium salt II wherein $Z^1$ and $Z^2$ are each either C or N; $Z^3$ is S or O; $R^1$ is selected from the group consisting of $C_1$–$C_6$ alkyl, allyl, arenxyl, propargyl, and fused aryl; $R^2$ and $R^6$ are each selected from the group consisting of H, $C_1$–$C_6$ alkyl, allyl, arenxyl, propargyl, and fused aryl; if $Z^1$ is C, then $R^3$ is selected from the group consisting of H, $C_1$–$C_6$ alkyl, allyl, arenxyl, propargyl, $C_1$–$C_6$ O-alkyl, OH, halogen, and fused aryl; if $Z^1$ is N, then $R^3$ is absent; $R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and if $Z^2$ is C, then $R^5$ is selected from the group consisting of H, $C_1$–$C_6$ alkyl, allyl, arenxyl, propargyl, $C_1$–$C_6$ O-alkyl, OH, halogen, and fused aryl; if $Z^2$ is N, then $R^5$ is absent; and S- is a counter ion.

$R^y$ is a C-2 substituent. Preferred C-2 substituents are represented by the following structures:

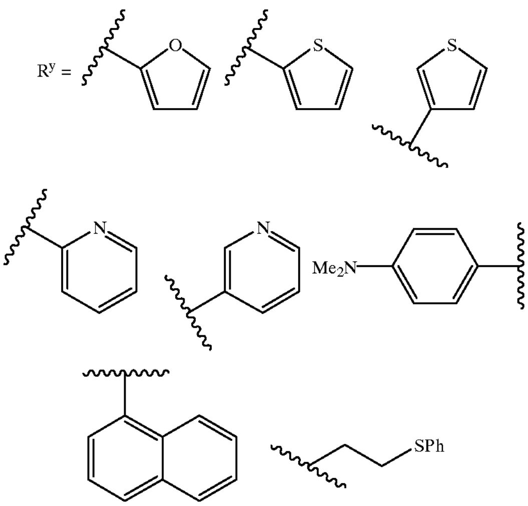

BRIEF DESCRIPTION OF THE DRAWINGS

FIG. 1 illustrates the kinetics of taxol release from taxol-2'-MPT (2) in various aqueous solutions at 25° C. (horizontal line). Although stable in water and aqueous buffer solutions, methylene chloride extraction of plasma treated with compound 2 showed complete conversion of 2 into taxol (1) within 10 minutes (curve, 20% of total recovered).

FIG. 2A illustrates a transmission electron micrograph (TEM) of self-assembled helical fibrous nanostructures of taxol-2'-MPT, i.e., compound 2 in buffered solutions (2,1 mM in 100 mM PBS) above the critical aggregation concentration (CAC) of this compound using a negative phosphotungstate stain and a magnification of ×25000. The inset shows a portion of one of the fibrils further magnified to illustrate the helical nature of the structure.

FIG. 2B illustrates a transmission electron micrograph (TEM) of self-assembled spherical nanostructures of taxol-2'-MPT (compound 2) in unbuffered solutions (2,1 mM in $H_2O$) above the critical aggregation concentration (CAC) of this compound using a negative uranyl acetate stain and a magnification of ×45000.

FIG. 3 illustrates a tubulin polymerization-depolymerization measurements with negative control (triangles), positive taxol control (diamonds), and taxol-2'-MPT, i.e., compound 2 (dots). Calcium chloride promoted depolymerization is suppressed by taxol but not by taxol-2'-MPT.

FIG. 4 illustrates the relative cytotoxicities of taxol-2'-MPT (compound 2) and taxol against a variety of cell lines.

FIG. 5 illustrates the efficacy of taxol-2'-MPT in lung tumor xenograft nude mouse model: 5% dextrose (triangles), taxol (diamonds), and taxol-2'-MPT (dots).

DETAILED DESCRIPTION

The synthesis, physical properties, and pharmaceutical profiles of water soluble onium salts of taxo-diterpenoid-$C^n$,2-O-aza-arenes are described.

Synthesis of Taxol-2'-MPT

Taxol-2'-MPT (methylpyridinium tosylate), compound 2, was synthesized according to the method of T. Mukaiyama, *Angewandte Chemie* 1979, 18(18), 707–808, incorporated herein by reference. Taxol (10 mg, 0.012 mM), from NaPro Biochemicals, Boulder Col., USA, was dried by azeotropic distillation with toluene (2×1.0 mL) and then dissolved in methylene chloride (0.4 mL) and treated sequentially under an atmosphere of dry argon, with freshly distilled triethylamine (5 microL, 0.04 mM, 3 equivalents) and 2-fluoro-1-methylpyridinium tosylate (5 mg, 0.018 mM, 1.5 equivalents) Aldrich Chemicals, and allowed to stir at ambient temperature for 30 minutes. The clear colorless solution rapidly turned to a clear pale yellow. The course of the reaction was monitored through thin layer chromatography (TLC) (E. Merck RP-18 silica, 65 tetrahydrofuran:35 water, UV/phosphomolybdic acid) and after thirty minutes of stirring at ambient temperature, judged complete as no taxol remained and only one compound was apparent by TLC (Rf 0.8). Purification via reverse phase high pressure liquid chromatography (HPLC) ($C_{18}$ column, 1 mM $NH_4O$ Ac pH 6.5 buffer/methanol gradient, 1.5 mL/min. UV) to give, after removal of solvent in vaccuo, pure taxol-2'-MPT (2) (12 mg, 93% yield) as a white amorphous solid. All spectroscopic data ($^1$H NMR and HRMS) were in accord with the structure assigned to 2. $^1$H NMR ($CDCl_3$, 125 MHz): 1.055 (s, 3 H, C17-H), 1.083 (s, 3 H, C19-H), 1.724 (s, 3 H, C19-H), 1.858 (m, 1 H, C6- H), 1.913 (s, 3 H, $CH_3$-Ph), 2.193 (s, 3 H, C10-OC(O)$CH_3$), 2.514 (m, 1 H, C6-aH), 3.663 (d, 1 H, J=7.0 Hz, C3-H), 4.110 (d, 1 H, J=8.5, C20- H, A of AB), 4.133 (s, 3 H, N-$CH_3$), 4.230 (d, 1 H, J=8.5, C20-aH, B of AB), 4.315 (dd, 1 H, J=8.7, 10.7, C7-H), 4.901 (dd, 1 H, J=1.0, 7.7, C5-H), 5.501 (d, 1 H, C2-H, J=7.0), 5.702 (bt, 1 H, C2'-H, J=8.0), 5.951 (dd, 1 H, C13-H, J=1.0, 8.0), 6.120 (bd, 1 H, C3'-H, J=10.0), 6.181 (s, 1 H, C10-H) 7.702 (t, 1 H, N-H, J=7.5), 7.33–7.45 (m, 8 H, Ar-H), 7.56–7.62 (m, 4 H, Ar-H), 7.56–7.62 (m, 4 H, Ar-H), 7.68–7.75 (m, 4 H, Ar-H), 8.00–8.05 (m, 1 H Ar-H), 8.23–8.28 (m, 1 H, Pyr-H), 8.41 (m, 1 H, Pyr-H). IR (neat, KCl plate) $cm^{-1}$: 3640–3120 (bm), 3030–2870 (bm), 2320 (m), 1720 (s), 1630 (m), 1560 (m), 1500 (m), 1360 (s), 1160 (m), 1070 (m), 700 (m). UV/Vis ($CHCl_3$) nm: 254, 280. FAB HRMS: calc for $C_{53}H_{57}O_{14}N_2$: 945.3810; found: 945.3810

The molecular structures of taxol, compound 1, and of taxol-2'-MPT, compound 2, are illustated in Scheme 1A. The synthesis of taxol-2'-MPT is illustrated in Scheme 1B.

Schemes 1A and 1B

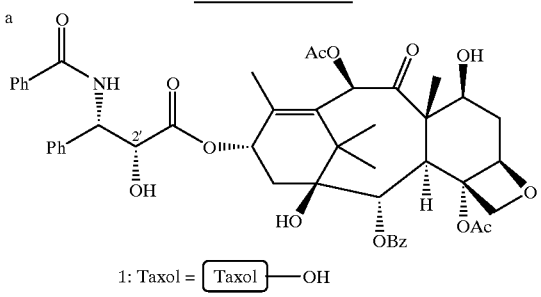

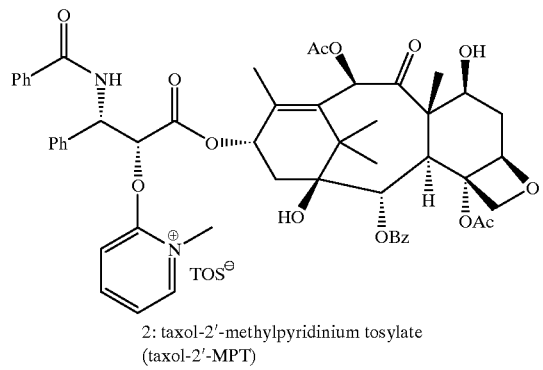

2: taxol-2'-methylpyridinium tosylate (taxol-2'-MPT)

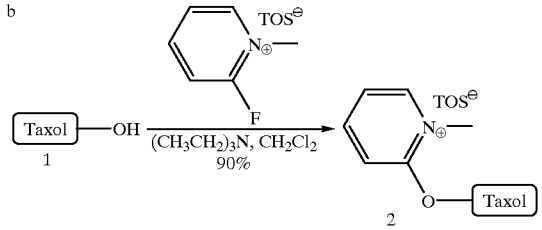

Synthesis of Taxol-7-MPT:

The synthesis of taxol-7-MPT differed only slightly from the synthesis of Taxol-2'-MPT. Taxol (10 mg, 0.012 mM), from NaPro Biochemicals, Boulder Col., USA, was dissolved in methylene chloride (2.0 mL) and treated sequentially with triethylamine (67 microL, 0.48 mM, 40 equivalents) and 2-fluoro-1- methylpyridinium tosylate (34 mg, 0.12 mM, 10 equivalents) Aldrich Chemicals, and allowed to stir at ambient temperature for 5 minutes. Purification via reverse phase high pressure liquid chromatography (HPLC) gave pure taxol-2'-MPT (2) (12 mg, 93% yield) as a white amorphous solid. The Rf of taxol-7-MPT is about 0.3 minutes less than the Rf of taxol-2'-MPT. The yield was 11 mg or 85%. Spectroscopic data ($^1$H NMR and HRMS) were as expected.

Synthesis of Taxol-bis-2',7-MPT

The synthesis of taxol-bis-2',7-MPT differed from the synthesis of Taxol-7-MPT only with respect to reaction time. Taxol (10 mg, 0.012 mM), from NaPro Biochemicals, Boulder Col., USA, was dissolved in methylene chloride (2.0 mL) and treated sequentially with triethylamine (67 microL, 0.48 mM, 40 equivalents) and 2-fluoro-1- methylpyridinium tosylate (34 mg, 0.12 mM, 10 equivalents) Aldrich Chemicals, and allowed to stir at ambient temperature for 18 hours. Purification via reverse phase high pressure liquid chromatography (HPLC) gave pure taxol-2'-MPT (2) (12 mg, 93% yield) as a white amorphous solid. The Rf of taxol-bis-2',7-MPT is about 0.3 minutes less than the Rf of taxol-2'-MPT. The yield was 13 mg or 85%. Spectroscopic data ($^1$H NMR and HRMS) were as expected.

Alternative synthetic schemes based upon the method of T. Mukaiyama (*Angewandte Chemie* 1979, 18(18), 707–808) using a variety of onium salts of 2-halogenated aza-arenes for derivatizing either the 2' or the 7 positions of taxol are illustrated in the following scheme:

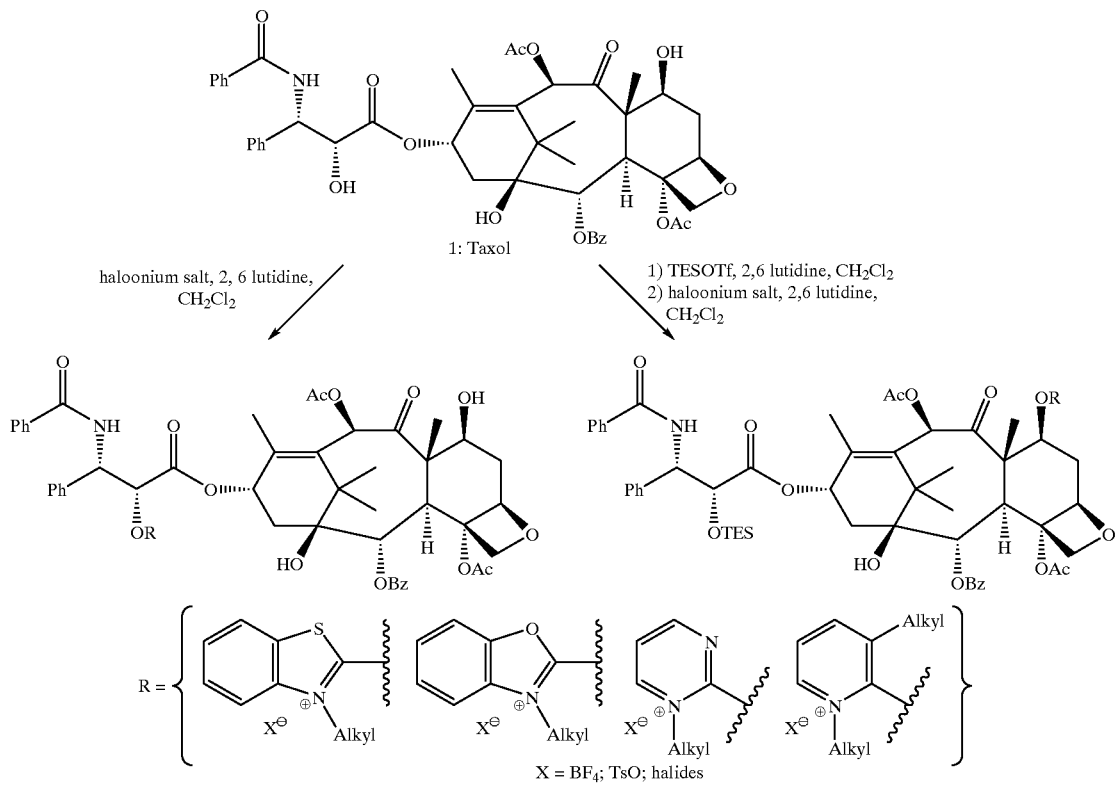

Stability measurements and Kinetics of Taxol release

Due to a difference in retention time using our standard HPLC conditions (see FIG. 1) and differing ultraviolet absorption maxima ($1_{280}/1_{254}$=1.6 for 2 and 0.3 for 1), the stability of 2 was easily assayed by HPLC (FIG. 1). In all of the ensuing studies, the only degradation products detected were taxol and the pyridinone that results from hydrolysis of pyridinium salts (FIG. 1c.). Taxol-2'-MPT appears completely stable in the solid state in a temperature range of −80° C. to 25° C. regardless of the presence of an inert atmosphere. In water, 5% dextrose, and 1.5% saline 2 is stable for several days but begins to exhibit slow degradation after 4 days. In phosphate buffered saline (PBS) or ammonium acetate—phosphate buffer systems of pH 6.0 to 7.3, 2 is stable at 25° C. for over 21 days. Taxol-2'-MPT (2) is, however, unstable in 5% HCl (pH 1.1) and brine. Most significantly, 2 breaks down rapidly when incubated at 37° C. with human plasma. This result suggests the presence of factors within plasma that initiate the degradation of 2 to taxol. Since taxol has been shown to bind to albumin to the extent of ca. 85% in sera, it is suspected that basic lysine residues on this protein may initiate breakdown.

The kinetics of taxol release from taxol-2'-MPT (2) in various aqueous solutions at 25° C. is shown in FIG. 1. In sterile water, pH 6.2 phosphate buffered saline, or 5% dextrose, no taxol release is observed over a period of 11 minutes, as shown by the horizontal line. Although stable in water and aqueous buffer solutions, methylene chloride extraction of plasma treated with compound 2 showed complete conversion of 2 into taxol (1) within 10 minutes, as shown by the curved line. Under these conditions 20% of total is recovered. More particularly, Taxol-2'-MPT (2) was dissolved in the aqueous system with the aid of sonication for five minutes. Aliquots were then removed at the times shown and partitioned into methylene chloride to quench the reaction. Samples were then analyzed using a Waters Maxima HPLC instrument equipped with an autoinjector (3.9×300 mm $C_{18}$ column equipped with a precolumn. The flow rate was 1.5 mL/minute. The eluent gradient A-B extended over 30 minutes. "A" was 80% 80 mM ammonium acetate, pH 6.0. "B" was 100% methanol. An ultraviolet diode array detector was employed. The ratio of compound 2 (Rf 16.2 min.) to taxol (compound 1, Rf 16.8 min.) remaining was determined from the relative areas of the peaks after normalization with previously determined calibration curves.

Solubility Measurements

The solubility and partition coefficient data for 2 and taxol were determined using an HPLC method.

|  | Taxol | 2'-MPT-taxol |
|---|---|---|
| Solubility in Water | <1.5 × 10$^{-6}$ | 1.7 × 10$^{-3}$ |
| Partition Coefficient [octanol/[water] | >10000 | 50 |

Solubility was found by forming a solution in water with the aid of sonication for five minutes, centrifugation of the samples, and injection of the supernatant. The values reported were normalized using calibration curves constructed for both compounds by preparing known concentrations in the range 1×10$^{-6}$ to 1×10$^{-3}$ M in methylene chloride and subjecting to HPLC analysis under the same conditions. One should note that the solubility of taxol is at the detection limit of the instrument and thus represents an upper limit. The solubility of 2 was found at a concentration at which the solution was clear (see below) and thus represents a lower limit. Compound 2 exhibited similar solubilities for various buffer systems in the pH range 6.2 to 7.4. Partition coefficients were determined by dissolving the compound in the organic phase, shaking the resulting solution with water for ten minutes, and analyzing each phase by HPLC as above. No degradation of 2 was noted during these studies. These data clearly show that 2 is significantly more soluble in water than the parent taxol. The solubility demonstrated in a range of aqueous systems is higher than the clinically relevant dosages (3 to 30 mM).

Self-Assembling Structures

Figure 2A:
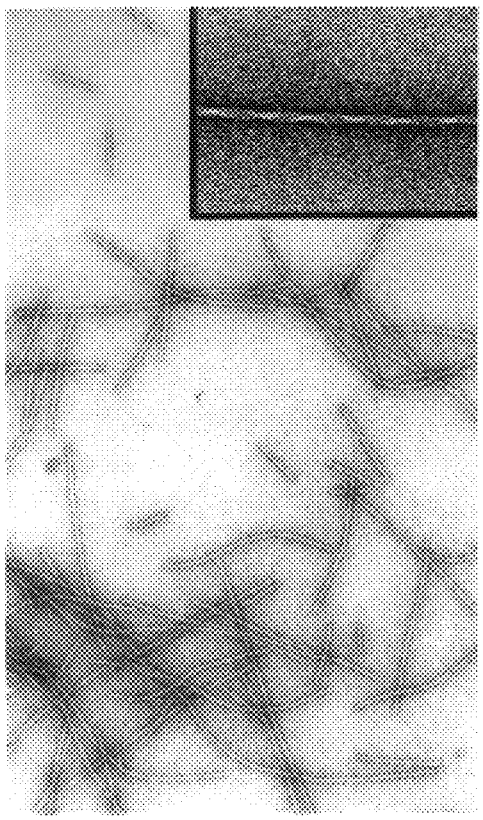
Figure 2B:
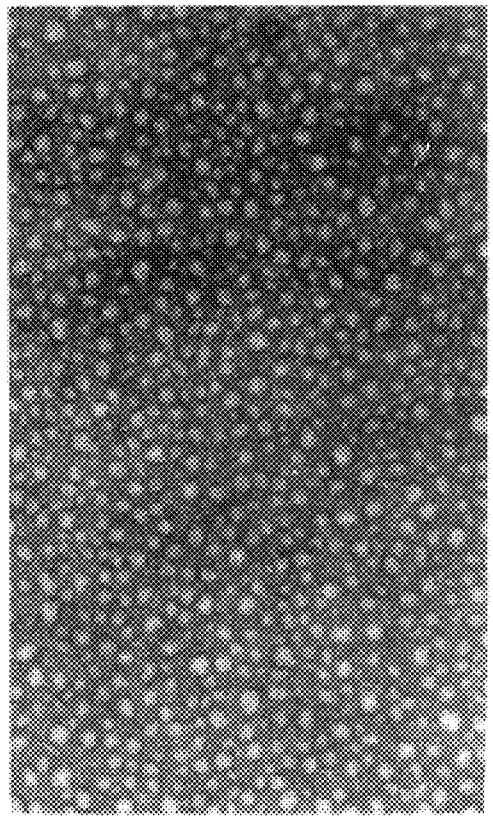

While the water solutions of 2 were optically clear at all concentrations examined, buffered solutions of concentrations greater than $1\times10^{-3}$ M exhibited a haze to the naked eye and diffuse scattering of monochromatic light. Ultraviolet spectroscopic absorption measurements at 340 nm (FIG. 3) showed an exponential increase in optical density (OD) above a critical concentration of $4\times10^{-4}$ M, a result characteristic of macromolecular structure in solution. Transmission electron microscopy (TEM) confirmed the presence of supramolecular structures in these solutions. Uniform aggregates of fibrillar structure (FIG. 2a) with helical conformations were observed. These structures exhibited varying (up to 800 Å) lengths but consistent diameter of ca. 80 Å with a helical twist of about 7. Additionally, freshly sonicated solutions of 2 showed the presence of spherical structures (FIG. 2b) with diameters of about 50 Å. It is likely that the long term stability of these solutions is due, at least in part, to stabilization provided by this structured environment.

Microtubule polymerization-depolymerization measurements

Microtubule polymerization-depolymerization measurements (FIG. 3) with taxol-2'-MPT (2) were very similar to GTP-saline controls and drastically different from taxol. Compound 2 does not appear to bind to tubulin in the manner of taxol. In the buffered aqueous environment of this assay, 2 is not converted to taxol and thus does not affect the tubulin-microtubule equilibria. Taxol, recovered from human plasma treated with 2, exhibited the expected microtubule stabilization, indicating that 2 does act as a prodrug for taxol.

Figure 3:
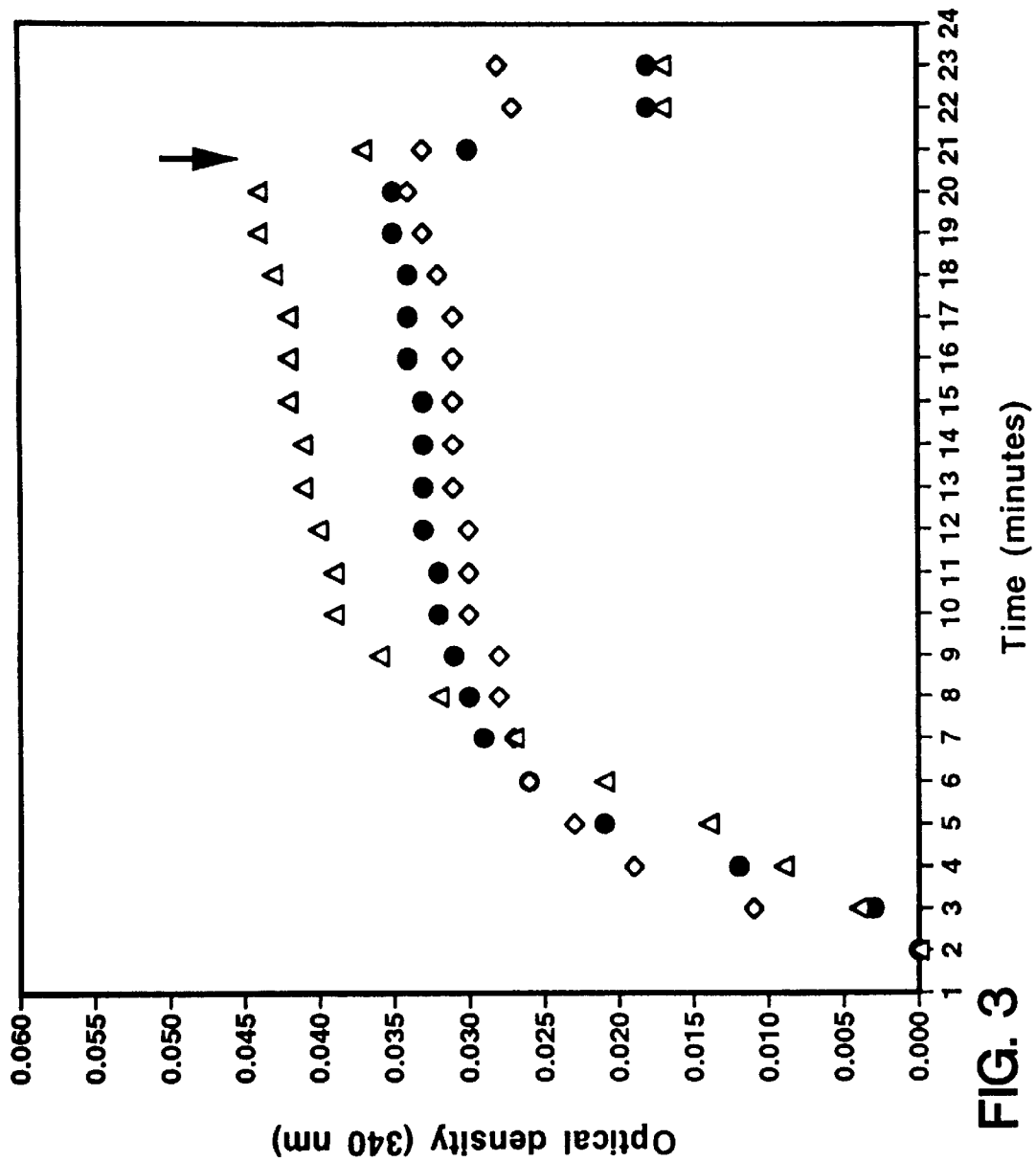

Tubulin polymerization-depolymerization measurements are illustrate in FIG. 3. Negative controls are shown with triangles; positive taxol controls are shown with diamonds; and taxol-2'-MPT, i.e., compound 2 is shown with dots. The measurements indicate that calcium chloride promoted depolymerization is suppressed by taxol but not by taxol-2'-MPT.

More particularly, measurement were performed in 96 well plates at 37° C. following the protocol of R. Merlock and W. Wrasidlo (*Analytical Biochemistry* 1993, in press). Calcium chloride addition is indicated by the arrow. In each case, 1.0 mM GTP was used to promote the initial polymerization of tubulin. Negative control employed tubulin (1.0 mg/mL) alone, $CaCl_2$ (0,25 mM) added after 20 minutes. Positive taxol control employed tubulin (1.0 mg/mL) with taxol ($10^{-6}$ M) and $CaCl_2$ (0.25 mM) added after 20 minutes. The experimental taxol-2'-MPT employed tubulin (1.0 mg/mL) with taxol-2'-MPT ($10^{-6}$) and $CaCl_2$ (0.25 mM) added after 20 minutes. Turbidity was measured as optical density at 340 nm using a microplate reader (Molecular Devices Thermomax).

Toxicity Measurements

Figure 4:
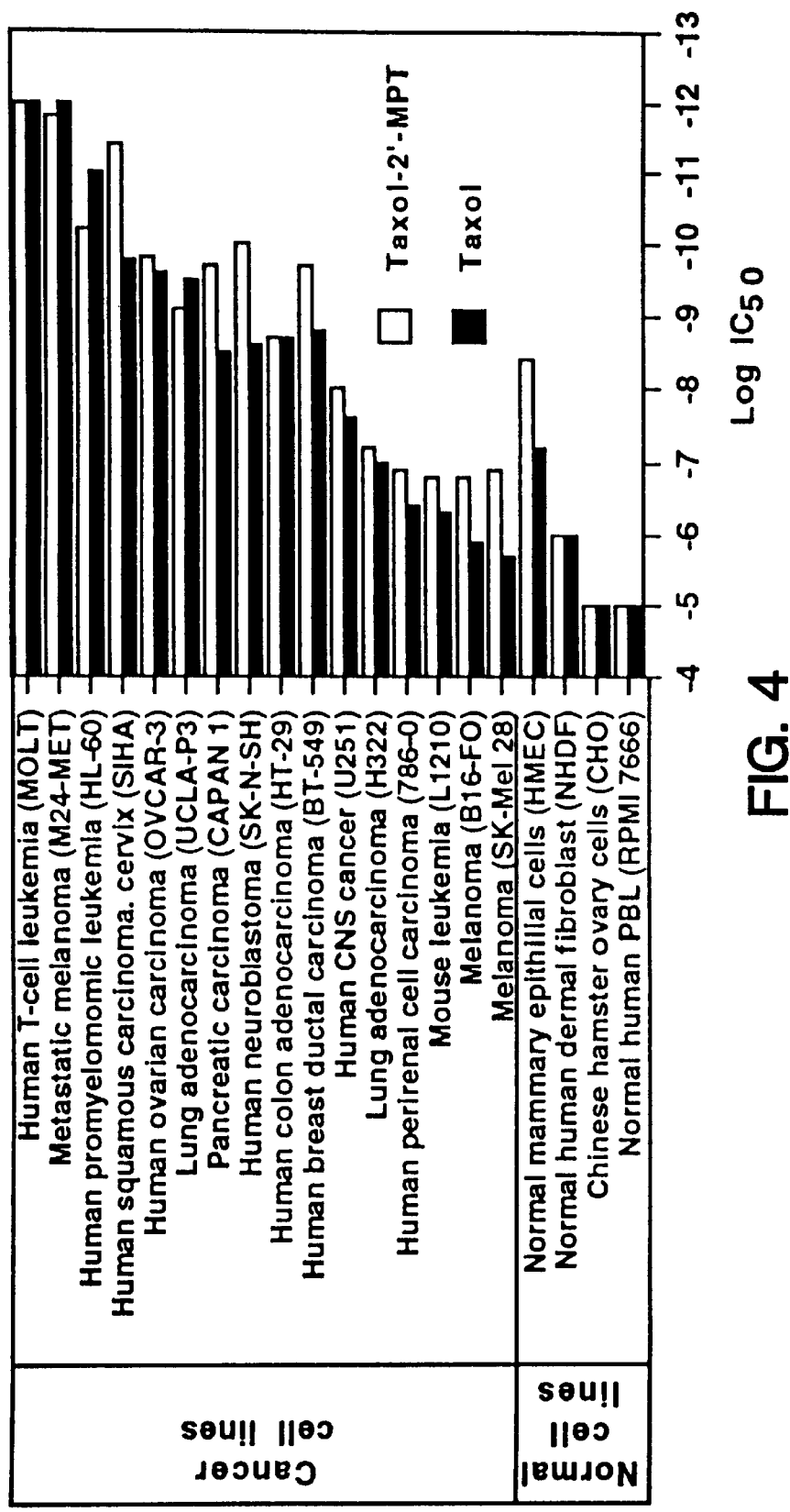

Compound 2 was tested for its cytotoxicity against a cell line panel including leukemia, ovarian, lung, and breast carcinoma cells (FIG. 4). The differential cytotoxicity profiles for 2 and taxol were similar, although some differences were noted. Both compounds exhibited $IC_{50}$ values ranging from $10^{-5}$ to $10^{-12}$ M with means close to one nanomolar. Normal cells had cytotoxicity levels three to four orders of magnitude below mean values. Extremely high cytotoxicity levels were recorded for human leukemia, metastatic melanoma and cervical carcinoma. As expected for a prodrug of taxol in the cellular environment, 2 shows the same remarkable tumor cell selectivity and cell line specificity as taxol.

The relative cytotoxicities of taxol-2'-MPT (compound 2) and taxol against a variety of cell lines are illustrated in FIG. 4. More particularly, cells were plated on 96 well plates with the following controls: no cells and toxic control ($1\times10^{-3}$ M SDS). The drug was added to the first set of wells and diluted via standard dilution method from the stock. Plates were incubated at 37° C., 5% $CO_2$ in sterile air in an humidified incubator for 72 hours. An aliquot of 50 L of a solution of 2,3-bis(methoxy-4-nitro-5-sulfophenyl)-5-[(phenylamino)carbonyl]-1H-tetrazolium hydroxide (XTT), 1 mg $mL^{-1}$, in phosphate buffered saline (PBS, 100 mM) was added to the wells. In the presence of viable cells, this colorless clear media is enzymatically altered to give a pink coloration. The plates were read at 450 nm using a plate reader. Percentage cytotoxicity was calculated using the formula: %C=1—(OD toxin)(OD growth control)$^{-1}$ (100).

Efficacy of taxol-2'-MPT in lung tumor xenograft

The encouraging in vitro data obtained with taxol-2'-MPT (2) prompted us to study its in vivo action using nude mice inflicted with human lung carcinoma xenografts (FIG. 1). The samples of 2 used for this study were formulated in sterile PBS without Cremaphor™, indicating the suitability of this compound for simple bolus administration. Preliminary data shows that the control of tumor growth exhibited by 2 is at least comparable to that of taxol and significantly (0.001 p-value, multiple linear regression model) different from controls. These results provide a reasonable indication that 2 is converted rapidly to taxol in vivo and should thus exhibit pharmacology similar to taxol. Indeed, in metabolic study using tritiated 2, only 5% of the compound was excreted through the kidneys, a result that is completely in accord with the behavior of taxol.

Figure 5:
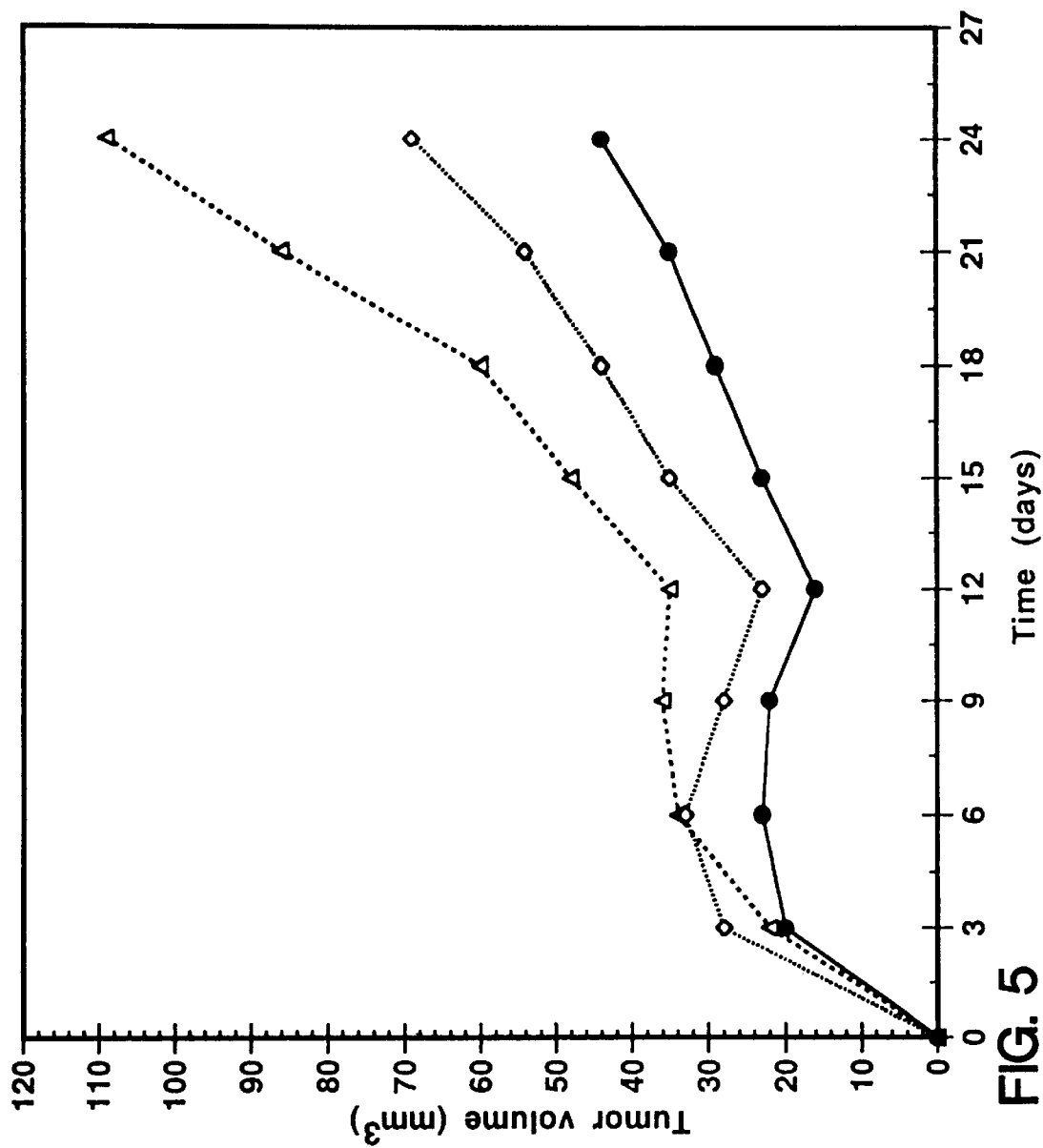

The efficacy of taxol-2'-MPT in lung tumor xenograft nude mouse model is illustrated in FIG. 5. The tumor model was generated from an ATCC A549 non-small cell lung adenocarcinoma cell line that was maintained under the standard cell proliferation conditions (37° C., 5% carbon dioxide in sterile air). Hemocytometer counted cells suspended in Hanks medium (Gibco, Grand Island N.Y.) were implanted S.C. ($10^6$ cells in 0.4 mL per tumor volume determined using the equation (length)(width)$^2$/2. The test compounds (1.0 microM) were injected I.P. on day 1,3, and 7 using the following media: control. 5% dextrose in water (D5W), triangles; taxol, suspended in Cremaphor/D5W (5/95, 18.0 mg/kg of animal weight), diamonds; and taxol-2'-MPT, dissolved in D5W (23.9 mg/kg of animal wight), dots. The procedures used for the maintenance of tumors and the experimental details were according to protocols set forth by the Developmental Therapeutics Program, National Cancer Institute, viz., *National Cancer Institute Cancer Chemotherapy Reports*, 3 (1972).

Mechanisms of taxol release

The mechanism of acid catalyzed taxol (1) release from taxol-2'-MPT is illustrated in Scheme 2.

Scheme 2

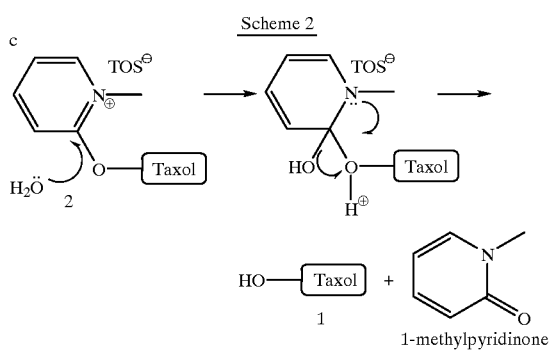

However, the release of taxol from taxol-2'-MPT can also be catalyzed by serum protein and by proteins having nucleophilic groups. When contacted with serum protein, taxol-2'-MPT is observed to displace its MPT group and form a protein:taxol intermediate. Dialysis of the protein:taxol intermediate indicates a dissociation period of hours or days. Displacement of the MPT group by serum proteins seems to be specific for such serum proteins. Tested non-serum proteins seemed to lack this activity. In particular, immunoglobulins and serum albumen seem to be particularly effective displacing the MPT group and forming protein:taxol intermediates. The precise nature of the bonding between the protein and taxol has not been characterized. Scheme 2 illustrates alternative pathways for MPT release.

Discussion

Taxol-2'-MPT has proven to be a remarkably stable compound in most aqueous media. It is probable that this stability is conferred upon 2 by the facile formation of supramolecular aggregates, a process that is probably driven by the amphiphillic nature of the compound. The stability, water solubility, and lack of cytotoxicity of taxol-2'-MPT makes this class of compound an ideal a prodrug for taxol and memetics of taxol. While essentially completely stable in aqueous media at physiological pH and ion strength, the compound rapidly discharges taxol in sera. This profile is ideal for a clinically useful prodrug to taxol. It is possible that these properties should allow the formulation of taxol-2'-MPT (2) without the use of Cremaphor™ or ethanol.

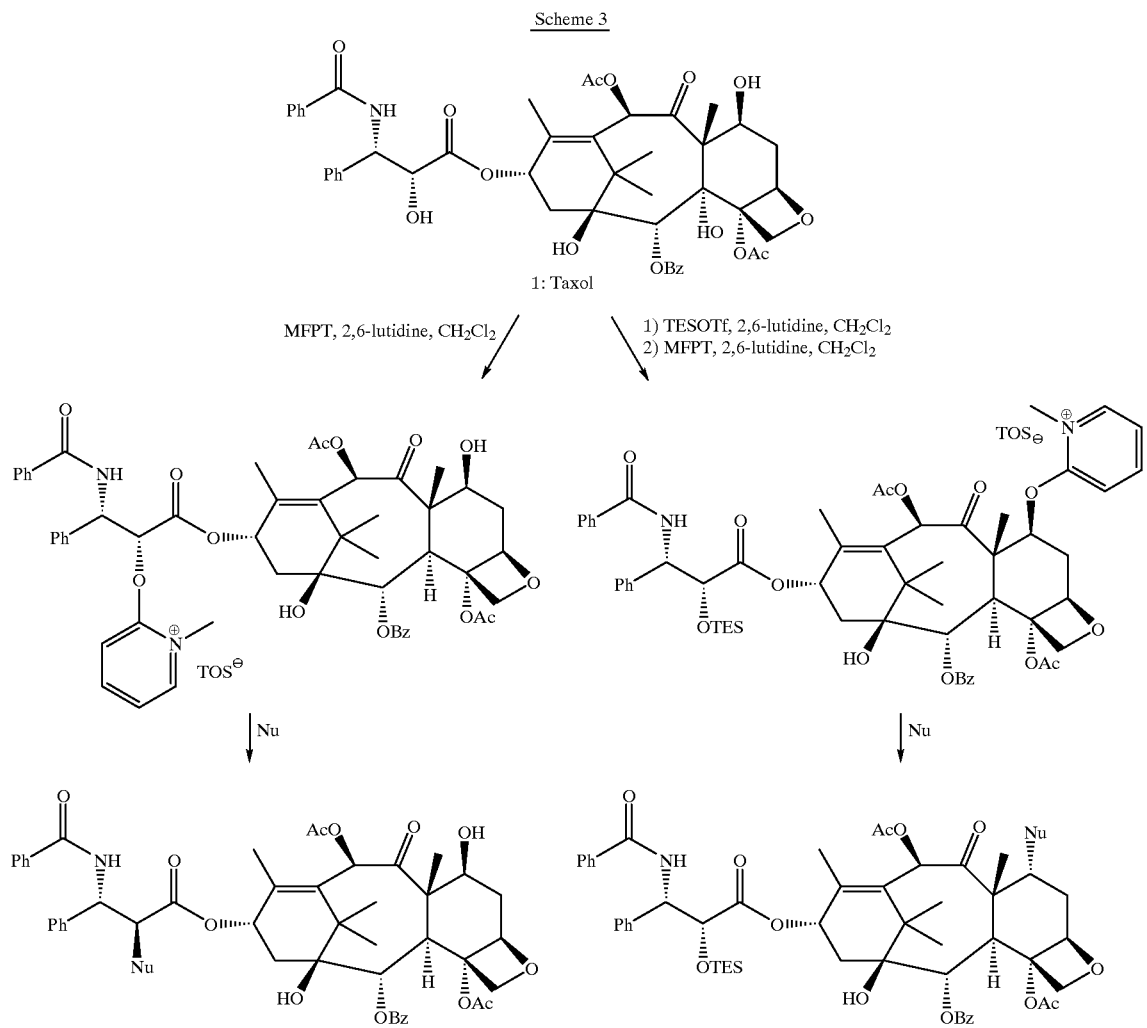

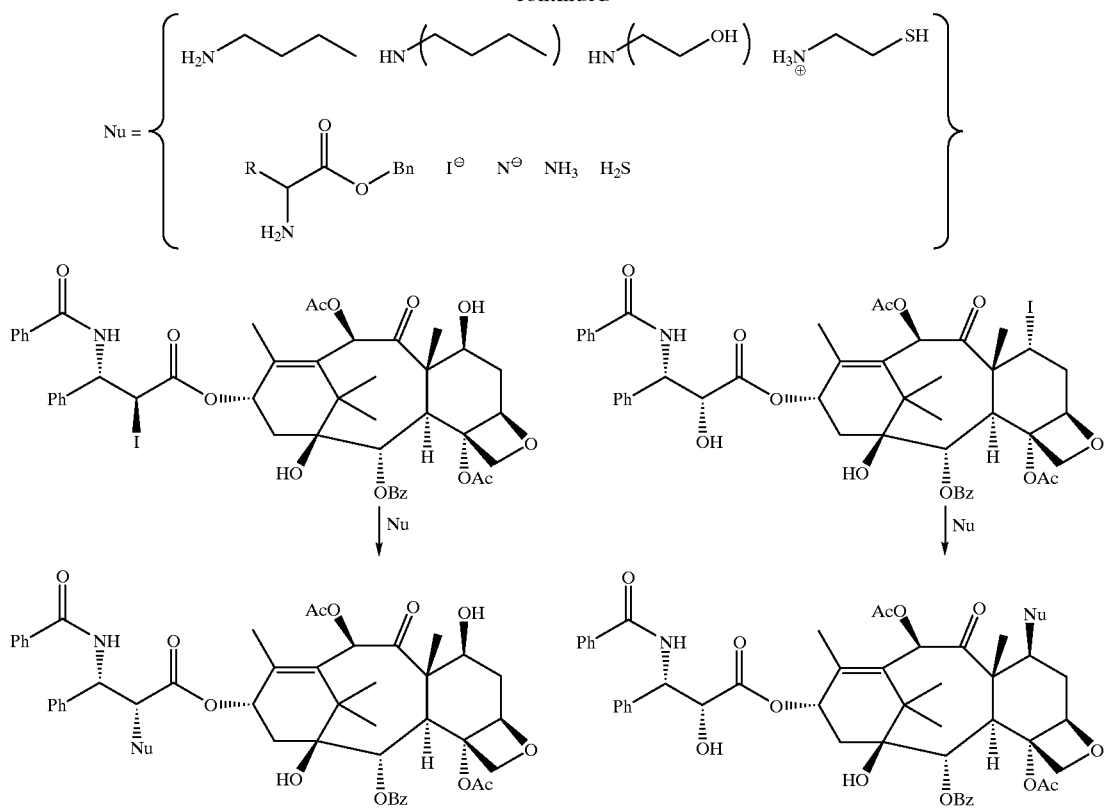

Synthetic Methods
Preparation of 7-TES deacetylbaccatin III (4)

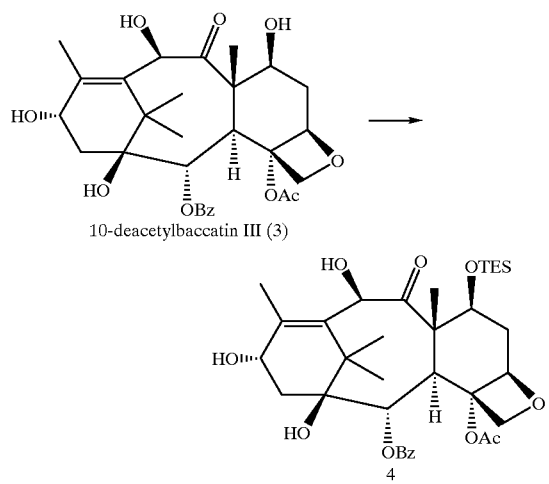

7-TES deacetylbaccatin III (4). To a solution of 10-deacetylbaccatin III (3, 3.0 g, 5.51 mnol, Indena Corpation, Italy) in pyridine (250 mL) was added chlorotriethylsilane (18.5 mL, 110 mmol) dropwise. The resulting solution was stirrred at 25° C. for 17 hours. After dilution with diethylether (750 mL), the solution was washed with aqueous $CuSO_4$ (3×200 mL) and brine (200 mL). The organic layer was dried ($MgSO_4$), concentrated, and purified by flash chromatography (silica, 35→50% ethylacetate in petroleum ether) to give alcohol 4 (3.39 g, 91%) as a white solid.

Physical Data for 7-TES deacetylbaccatin III (4). $R_f$ 0.32 (silica, 50% ethylacetate in hexanes); IR (thin film) $v_{max}$ 3464, 2954, 2282, 1710, 1453, 1362, 1271, 1242, 1105, 994 cm$^{-1}$; $^1$H NMR (500 MHz, CDCl$_3$) δ 8.06 (dd, J=8.0, 0.9 Hz, 2 H, Bz), 7.57 (t, J=7.9 Hz, 1 H, Bz), 7.44 (t, J=7.9 Hz, 2 H, Bz), 5.56 (d, J=7.0 Hz, 1 H, 2-H), 5.14 (d, J=1.9 Hz, 1 H, 10-H), 4.92 (d, J=9.5 Hz, 1 H, 5-H), 4.84–4.78 (m, 1 H, 13-H), 4.37 (dd, J=10.6, 7.0 Hz, 1 H, 7-H), 4.27 (d, J=8.5 Hz, 1 H, 20-H), 4.25 (d, J=1.9 Hz, 1 H, 10-OH), 4.12 (d, J=8.5 Hz, 1 H, 20-H), 3.91 (d, J=7.0 Hz, 1 H, 3-H), 2.48–2.40 (m, 1 H, 6-H), 2.25 (s, 3 H, Me), 2.25–2.17 (m, 2 H, 14-CH$_2$), 2.04 (s, 3 H, Me), 1.90–1.82 (m, 1 H, 6-H), 1.70 (s, 3 H, Me), 1.03 (s, 6 H, Me, Me), 0.90 (t, J=8 Hz, 9 H, Si(CH$_2$CH$_3$)$_3$), 0.58–0.42 (band, 6 H, Si(CH$_2$CH$_3$)$_3$); $^{13}$C NMR (125 MHz, CDCl$_3$) δ 210.3, 170.8, 167.0, 141.8, 135.1, 133.6, 130.1, 129.4, 128.6, 84.2, 80.7, 78.8, 76.5, 74.8, 74.6, 72.9, 67.9, 57.9, 47.0, 42.7, 38.6, 37.2, 26.8, 22.6, 19.5, 15.2, 9.9, 6.7, 5.1; FAB HRMS (NBA/CsI) m/e 791.2251, M+Cs$^+$ calcd for C$_{35}$H$_{50}$O$_{10}$Si 791.2228.

Preparation of enone 5

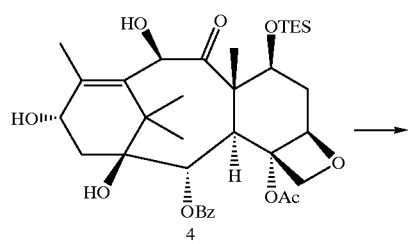

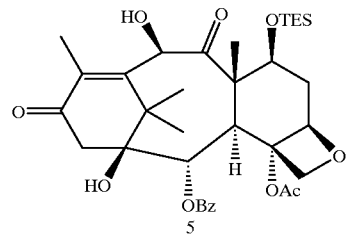

5

Enone 5. To a solution of 7-TES deacetylbaccatin III (4, 1.5 g, 2.28 mmol) and 4-methylmorpholine N-oxide (NMO, 240 mg, 2.05 mmol) in $CH_2Cl_2$ (5 mL) was added 4 Å molecular sieves (200 mg) and the suspension was stirred at 25° C. for 10 minutesutes. A catalytic amount of tetrapropylammonium perruthenate from Aldrich Chemical Company Inc. (TPAP, 40 mg, 0.11 mmol) was added by portions and the reaction mixture was stirred at 25° C. for 0.5 hours. Small amounts of 4-methylmorpholine N-oxide and TPAP were added alternatively at 0.5 hour intervals until the starting material was consumed to the extent of ca. 95% by TLC. The reaction mixture was filtered through silica gel, eluted with $CH_2Cl_2$ (100 mL), and concentrated to give enone 5 (1.44 g, 96%) as a white solid.

Physical Data for Enone 5. $R_f$=0.5 (silica, 50% ethylacetate in hexanes); IR (thin film) $v_{max}$ 3446, 2957, 2882, 1726, 1672, 1456, 1367, 1243, 1106 cm$^{-1}$; $^1$H NMR (500 MHz, CDCl$_3$) δ8.05 (dd,J=8.0, 1.0 Hz, 2 H, Bz), 7.61 (t,J=7.5 Hz, 1 H, Bz), 7.45 (t,J=7.5 Hz, 2 H, Bz), 5.63 (d,J=7.5 Hz, 1 H, 2-H), 5.30 (d,J=2.0 Hz, 1 H, 10-H), 4.90 (d, J=8.0 Hz, 1 H, 5-H), 4.36 (dd, J=10.5, 7.0 Hz, 1 H, 7-H), 4.31 (d, J=8.5 Hz, 1 H, 20-H), 4.30 (d, J=2.0 Hz, 1 H, 10-OH), 4.11 (d, J=8.5 Hz, 1 H, 20-H), 3.93 (d, J=7.5 Hz, 1 H, 3-H), 2.92 (d, J=19.5 Hz, 1 H, 14-H), 2.62 (d, J=19.5 Hz, 1 H, 14-H), 2.50–2.42 (m, 1 H, 6-H), 2.17 (s, 3 H, Me), 2.08 (s, 3 H, Me), 1.90–1.82 (m, 1 H, 6-H), 1.77 (s, 1 H, 1-OH), 1.70 (s, 3 H, Me), 1.21 (s, 3 H, Me), 1.14 (s, 3 H, Me), 0.90 (t, J=8.0 Hz, 9 H, Si(CH$_2$CH$_3$)$_3$), 0.60–0.42 (band, 6 H, Si(CH$_2$CH$_3$)$_3$); $^{13}$C NMR (125 MHz, CDCl$_3$) δ208.2, 198.1, 170.2, 166.8, 156.6, 139.1, 134.0, 130.0, 128.8, 128.8, 84.0, 80.4, 78.5, 76.2, 75.7, 72.9, 72.8, 58.8, 45.9, 43.4, 42.5, 37.2, 33.0, 21.7, 17.5, 13.6, 9.6, 6.7, 5.1; FAB HRMS (NBA/NaI) m/e 657.3070, M+Na$^+$ calcd for C$_{35}$H$_{48}$O$_{10}$Si 657.3095.

Preparation of triol 6

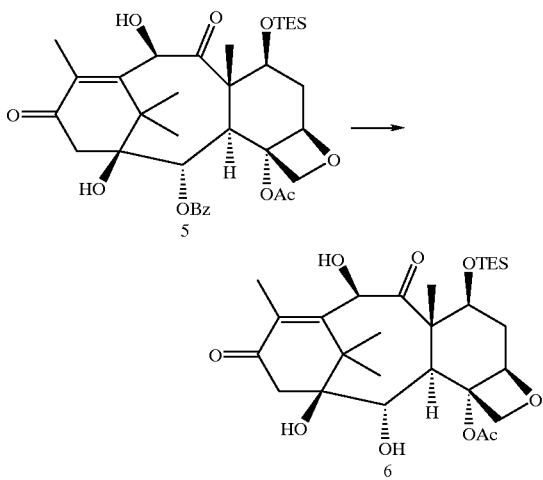

Triol 6. To a solution of enone 5 (1.44 g, 2.19 mmol) in MeOH (300 mL) at 0° C. was slowly added an aqueous solution of K$_2$CO$_3$ (3.0 g in 32 mL of H$_2$O). The solution was stirred at 0° C. for 2.5 hours. The reaction was then quenched with aqueous NH$_4$Cl (150 mL) and the resulting mixture was extracted with CH$_2$Cl$_2$ (2×200 mL). The organic layer was dried (Na$_2$SO$_4$), concentrated, and purified by flash chromatography (silica, 35→50% ethylacetate in petroleum ether) to give enone 5 (270 mg, 19%) and triol 6 (912 mg, 93% based on 81% conversion).

Physical Data for Triol 6. $R_f$=0.24 (silica, 50% ethylacetate in hexanes); IR (thin film) $v_{max}$ 3414, 2957, 2881, 1727, 1664, 1370 cm$^{-1}$; $^1$H NMR (500 MHz, CDCl$_3$) δ5.23 (d, J=9.5 Hz, 1 H, 10-H), 4.89 (d, J=9.5 Hz, 1 H, 5-H), 4.63 (d, J=9.5 Hz, 1 H, 20-H), 4.56 (d, J=9.5 Hz, 1 H, 20-H), 4.32 (dd, J=11.0, 7.0 Hz, 1 H, 7-H), 4.28 (d, J=2.5 Hz, 1 H, 10-OH), 3.89 (dd, J=6.5, 4.0 Hz, 1 H, 2-H), 3.57 (d, J=6.5 Hz, 1 H, 3-H), 2.78 (d, J=19.5 Hz, 1 H, 14-H), 2.58 (d, 4.0 Hz, 1 H, 2-OH), 2.52 (d, J=19.5 Hz, 1 H, 14-H), 2.49–2.42 (m, 1 H, 6-H), 2.03 (s, 3 H, Me), 1.92–1.84 (m, 1 H, 6-H), 1.68 (s, 3 H, Me), 1.21 (s, 3 H, Me), 1.04 (s, 3 H, Me), 0.90 (t, J=8.0 Hz, 9 H, Si(CH$_2$CH$_3$)$_3$), 0.60–0.40 (band, 6 H, Si(CH$_2$CH$_3$)$_3$); $^{13}$C NMR (125 MHz, CDCl$_3$) δ208.9, 198.5, 170.1, 156.7, 138.8, 83.8, 81.2, 77.6, 75.7, 72.8, 72.5, 58.8, 45.8, 43.1, 42.8, 37.3, 32.7, 21.6, 17.5, 13.6, 9.7, 6.7, 5.1; FAB HRMS (NBA/NaI) m/e 575.2648, M+Na$^+$ calcd for C$_{28}$H$_{44}$O$_9$Si 575.2652.

Preparation of Carbonate 7

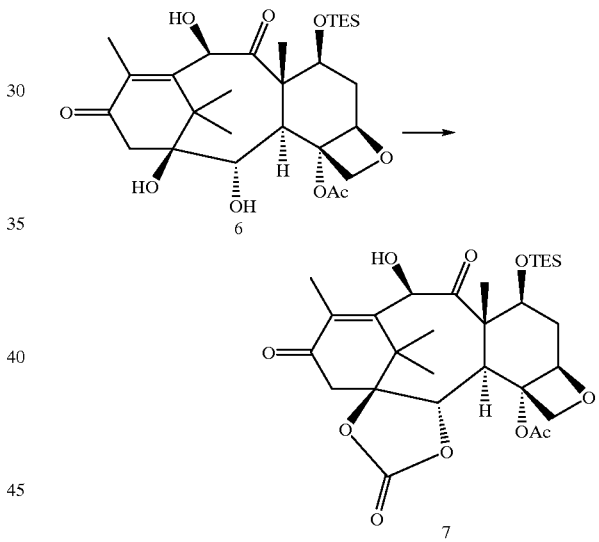

Carbonate 7. A solution of triol 6 (60.0 mg, 0.109 mmol) in THF (2 mL) was treated with carbonyldiimidazole (110.0 mg, 0.678 mmol) and stirred at 40° C. for 0.5 hour The reaction mixture was concentrated and redisolved in THF (5 mL). TLC analysis confirmed total consumption of starting material. 1 N aqueous HCl (5 mL) was added and the resulting solution was allowed to stir for 15 minutes at 25° C. diethylether (25 mL) was added, the organic layer was separated, washed with aqueous NaHCO$_3$ (10 mL) and brine (10 mL), dried (MgSO$_4$), and concentrated to give carbonate 7 (58 mg, 93%) as a white foam.

Physical Data for Carbonate 7. $R_f$=0.50 (silica, 35% ethylacetate in hexanes); IR (thin film) $v_{max}$ 3438, 2957, 2882, 1820, 1731, 1685, 1370, 1236 cm$^{-1}$; $^1$H NMR (500 MHz, CDCl$_3$) δ5.27 (d, J=2.5 Hz, 1 H, 10-H), 4.89 (d, J=9.0 Hz, 1 H, 5-H), 4.60 (d, J=9.0 Hz, 1 H, 20-H), 4.45 (d, J=9.0 Hz, 1 H, 20-H), 4.43 (d, J=6.0 Hz, 1 H, 2-H), 4.33 (dd, J=10.0, 7.5 Hz, 1 H, 7-H), 4.28 (d, J=2.5 Hz, 1 H, 10-OH), 3.54 (d, J=6.0 Hz, 1 H, 3-H), 2.88 (d, J=20.0 Hz, 1 H, 14-H), 2.75 (d, J=20.0 Hz, 1 H, 14-H), 2.54–2.47 (m, 1 H, 6-H), 2.08 (s, 3 H, Me), 2.06 (s, 3 H, Me), 1.92–1.84 (m, 1 H, 6-H), 1.77 (s, 3 H, Me), 1.31 (s, 3 H, Me), 1.15 (s, 3 H, Me), 0.88 (t, J=8.5 Hz, 9 H, Si(CH$_2$CH$_3$)$_3$), 0.55–0.45 (band, 6 H, Si(CH$_2$CH$_3$)$_3$); $^{13}$C NMR (125 MHz, CDCl$_3$) δ208.4, 195.5, 170.5, 154.0, 152.0, 141.2, 88.4, 83.9, 79.8, 79.0, 76.7, 75.7, 71.9, 60.3, 43.0, 41.6, 39.8, 37.7, 31.6, 21.5, 17.8, 14.4, 9.7, 6.6, 5.0;

FAB HRMS (NBA) m/e 579.2652, M+H$^+$ calcd for C$_{29}$H$_{42}$O$_{10}$Si 579.2626.

Preparation of n Butyl-C-2 ester derivative (Alcohol 8)

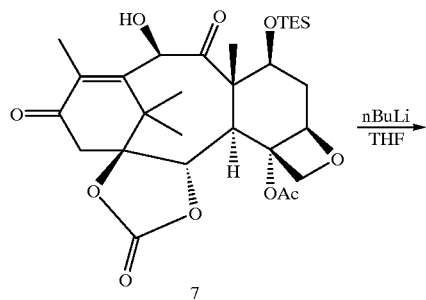

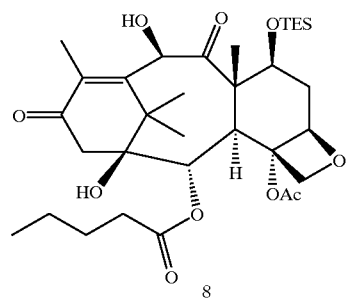

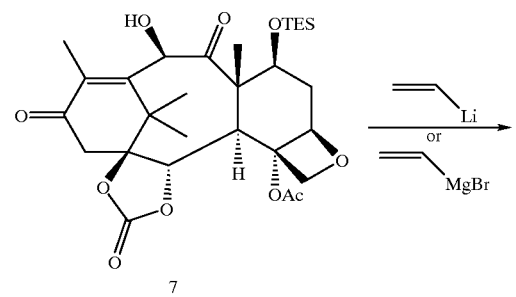

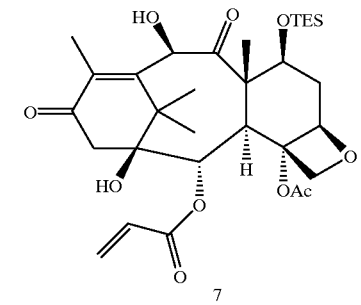

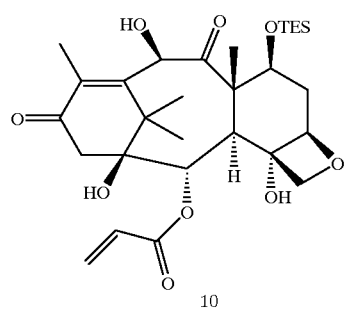

Alcohol 8. A solution of carbonate 7 (10 mg, 0.0173 mmol) in tetrahydrofuran (1 mL) at −78° C. was treated with n-Butyllithium from Aldrich Chemical Company, Inc. (0.087 mL of a 1.6 M solution in hexanes, 0.139 mmol) and stirred for 1.0 hour The reaction mixture was poured into a mixture of diethylether (10 mL) and aqueous NH$_4$Cl (5 mL). The organic layer was separated and the aqueous layer was extracted with diethylether (2×5 mL). The combined organic layer was washed with a saturated solution of brine (5 mL), dried (MgSO$_4$), concentrated, and purified by flash chromatography (silica, 35→50% ethylacetate in hexanes) to give 8 (7.9 mg, 72%) as an amorphous solid.

Physical Data for Alcohol 8. R$_f$=0.36 (silica, 35% ethylacetate in petroleum ether); IR (film) v$_{max}$ 3437, 2962, 2865, 1726, 1671, 1367, 1239, 1105 cm$^{-1}$; $^1$H NMR (500 MHz, CDCl$_3$) δ5.36 (d, J=6.5 Hz, 1 H, 2-H), 5.26 (d, J=2.5 Hz, 1 H, 10-H), 4.89 (br d, J=8.0 Hz, 1 H, 5-H), 4.47 (d, J=8.0 Hz, 1 H, 20-H), 4.32 (dd, J=10.5, 6.5 Hz, 1 H, 7-H), 4.26 (d, J=2.5 Hz, 1 H, 10-OH), 4.15 (d, J=8.0 Hz, 1 H, 20-H), 3.81 (d, J=6.5 Hz, 1 H, 3-H), 2.73 (d, J=20.0 Hz, 1 H, 14-H), 2.57 (d, J=20.0 Hz, 1 H, 14-H), 2.49–2.41 (m, 1 H, 6-H), 2.38–2.23 (m, 2 H, OCCH$_2$CH$_2$)$_2$CH$_3$), 2.06 (s, 3 H, Me), 2.04 (s, 3 H, Me), 1.90–1.82 (m, 1 H, 6-H), 1.67 (s, 1 H, OH), 1.64 (s, 3 H, Me), 1.68–1.52 (m, 2 H, OCCH$_2$CH$_2$CH$_2$CH$_3$), 1.41–1.30 (m, 2 H, OC(CH$_2$)$_2$CH$_2$CH$_3$), 1.19 (s, 3 H, Me), 1.07 (s, 3 H, Me), 0.94–0.86 (band, 12 H, CH$_3$ of Bu, OSi(CH$_2$CH$_3$)$_3$), 0.58–0.45 (band, 6 H, OSi(CH$_2$CH$_3$)$_3$); FAB HRMS (NBA) m/e 637.3421, M+H$^+$ calcd for C$_{33}$H$_{52}$O$_{10}$Si 637.3408.

Preparation of vinyl-C-2 ester derivative (Alcohols 9 and 10)

Alcohols 9 and 10. A solution of carbonate 7 (111.3 mg, 0.192 mmol) in tetrahydrofuran (2 mL) at −78° C. was treated with vinyllithium (3.7 mL of a 0.52 M solution in diethylether, 1.92 mmol, prepared from tetravinyltin and nButyllithium: methodology from Wakefield, B. J. *Organolithium Methods*, Academic Press: London, 1988, p. 46) and stirred for 2.25 hour. The reaction mixture was poured into a mixture of CH$_2$Cl$_2$ (20 mL) and aqueous NH$_4$Cl (10 mL), the organic layer was separated, and the aqueous layer was extracted with CH$_2$Cl$_2$ (3×10 mL). The combined organic layer was washed with brine (15 mL), dried (MgSO$_4$), concentrated, and purified by flash chromatography (silica, 30→50% ethylacetate in petroleum ether) to give 9 (60.0 mg, 52%), and 10 (25.7 mg, 24% ) as white foams.

Physical Data for Alcohol 9. R$_f$=0.52 (silica, 50% ethylacetate in hexanes); IR (film) v$_{max}$ 3442, 2956, 2882, 1727, 1672, 1407, 1368, 1243, 1182, 1110, 1050, 986, 826, 736 cm$^{-1}$; $^1$H NMR (500 MHz, CDCl$_3$) δ6.51 (dd, J=17.0, 1.0 Hz, 1 H, vinyl H), 6.13 (dd, J=17.0, 10.5 Hz, 1 H, vinyl H), 6.00 (dd, J=10.5, 1.0 Hz, 1 H, vinyl H), 5.45 (br d, J=6.5 Hz, 1 H, 2-H), 5.30 (d, J=2.5 Hz, 1 H, 10-H), 4.91 (br d, J=9.5 Hz, 1 H, 5-H), 4.44 (d, J=8.5 Hz, 1 H, 20-H), 4.35 (dd, J=10.5, 6.5 Hz, 1 H, 7-H), 4.30 (d, J=2.5 Hz, 1 H, 10-OH), 4.14 (d, J=8.5 Hz, 1 H, 20-H), 3.88 (d, J=6.5 Hz, 1 H, 3-H), 2.79 (d, J=20.0 Hz, 1 H, 14-H), 2.61 (d, J=20.0 Hz, 1 H, 14-H), 2.48 (ddd, J=14.5, 9.5, 6.5 Hz, 1 H, 6-H), 2.09 (s, 3 H, Me), 2.08 (s, 3H, Me), 1.89 (ddd, J=14.5, 10.5, 2.0 Hz, 1 H, 6-H), 1.72 (s, 1 H, OH), 1.68 (s, 3 H, Me), 1.22 (s, 3 H, Me), 1.12 (s, 3 H, Me), 0.92 (t, J=8.0 Hz, 9 H, OSi (CH$_2$CH$_3$)$_3$), 0.62–0.46 (band, 6 H, OSi(CH$_2$CH$_3$)$_3$); FAB HRMS (NBA/CsI) m/e 739.1925, M+Cs$^+$ calcd for C$_{31}$H$_{46}$O$_{10}$Si 739.1915.

Physical Data for Alcohol 10. $R_f$=0.24 (silica, 50% ethylacetate in hexanes); IR (film) $v_{max}$ 3439, 2955, 2881, 1711, 1671, 1409, 1365, 1188, 1115, 980, 833, 735 cm$^{-1}$; $^1$H NMR (500 MHz, CDCl$_3$) δ6.48 (br d, J=17.0 Hz, 1 H, vinyl H), 6.10 (dd, J=17.0, 10.5 Hz, 1 H, vinyl H), 5.97 (br d, J=10.5 Hz, 1 H, vinyl H), 5.47 (br d, J=6.0 Hz, 1 H, 2-H), 5.25 (d, J=2.5 Hz, 1 H, 10-H), 4.75 (dd, J=9.5, 3.5 Hz, 1 H, 5-H), 4.38 (d, J=8.5 Hz, 1 H, 20-H), 4.30 (d, J=2.5 Hz, 1 H, 10-OH), 4.24 (d, J=8.5 Hz, 1 H, 20-H), 3.90 (dd, J=11.5, 6.0 Hz, 1 H, 7-H), 3.28 (d, J=19.5 Hz, 1 H, 14-H), 3.24 (d, J=6.0 Hz, 1 H, 3-H), 3.06 (br s, 1 H, OH), 2.58 (d, J=19.5 Hz, 1 H, 14-H), 2.38 (ddd, J=14.5, 9.5, 6.0 Hz, 1 H, 6-H), 2.07 (s, 3 H, Me), 1.98 (ddd, J=14.5, 11.5, 3.5 Hz, 1 H, 6-H), 1.87 (s, 1 H, OH), 1.61 (s, 3 H, Me), 1.23 (s, 3 H, Me), 1.13 (s, 3 H, Me), 0.90 (t, J=8.0 Hz, 9 H, OSi(CH$_2$CH$_3$)$_3$), 0.59–0.45 (band, 6 H, OSi(CH$_2$CH$_3$)$_3$); FAB HRMS (NBA/CsI) m/e 697.1802, M+Cs$^+$ calcd for C$_{29}$H$_{44}$O$_9$Si 697.1809.

Preparation of 2-Furyl-C-2 ester derivative (Alcohol 11)

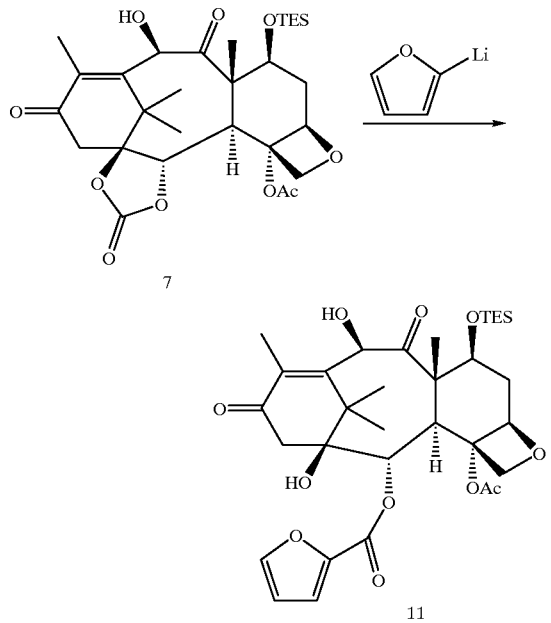

Alcohol 11. A solution of carbonate 7 (46 mg, 0.0795 mmol) in tetrahydrofuran (3 mL) at −78° C. was treated with 2-furyllithium (4 mL of a 0.47 M suspension in diethylether, 1.88 mmol, prepared from furan (Aldrich Chemical Company, Inc.) and n-Butyllithium (Aldrich Chemical Company, Inc.); methodology from Ramanathan, V.; Levine, R. *J. Org. Chem.* 1962, 27, 1216) and stirred for 10 minutesutes. The reaction mixture was poured into a mixture of CH$_2$Cl$_2$ (15 mL) and aqueous NH$_4$Cl (20 mL). The organic layer was separated and the aqueous layer was extracted with CH$_2$Cl$_2$ (2×10 mL). The combined organic layer was washed with brine (10 mL), dried (MgSO$_4$) and concentrated to give 11 which was taken into the next step without further purification.

Physical Data for Alcohol 11. $R_f$=0.38 (silica, 20% ethylacetate in petroleum ether); IR (film) $v_{max}$ 3442, 2956, 2882, 1727, 1672, 1468, 1300, 1240, 1110, 1007, 733 cm$^{-1}$; $^1$H NMR (500 MHz, CDCl$_3$) δ7.66–7.64 (m, 1 H, furan), 7.24 (br d, J=3.5 Hz, 1 H, furan), 6.58 (dd, J=3.5, 1.5 Hz, 1 H, furan), 5.55 (d, J=6.5 Hz, 1 H, 2-H), 5.31 (d, J=2.0 Hz, 1 H, 10-H), 4.92 (br d, J=9.0 Hz, 1 H, 5-H), 4.43 (d, J=8.5 Hz, 1 H, 20-H), 4.37 (dd, J=10.5, 6.5 Hz, 1 H, 7-H), 4.32 (d, J=2.0 Hz, 1 H, 10-OH), 4.18 (d, J=8.5 Hz, 1 H, 20-H), 3.93 (d, J=6.5 Hz, 1 H, 3-H), 2.88 (d, J=20.0 Hz, 1 H, 14-H), 2.63 (d, J=20.0 Hz, 1 H, 14-H), 2.55–2.37 (m, 1 H, 6-H), 2.15 (s, 3 H, Me), 2.09 (s, 3 H, Me), 1.93–1.87 (m, 1 H, 6-H), 1.81 (s, 1 H, OH), 1.71 (s, 3 H, Me), 1.23 (s, 3 H, Me), 1.15 (s, 3 H, Me), 0.93 (t, J=8.0 Hz, 9 H, OSi(CH$_2$CH$_3$)$_3$), 0.62–0.42 (band, 6 H, OSi(CH$_2$CH$_3$)$_3$); FAB HRMS (NBA/NaI) m/e 669.2717, M+Na$^+$ calcd for C$_{33}$H$_{46}$O$_{11}$Si 669.2707.

Preparation of 2-thiophenyl-C-2 ester derivative (Alcohol 12)

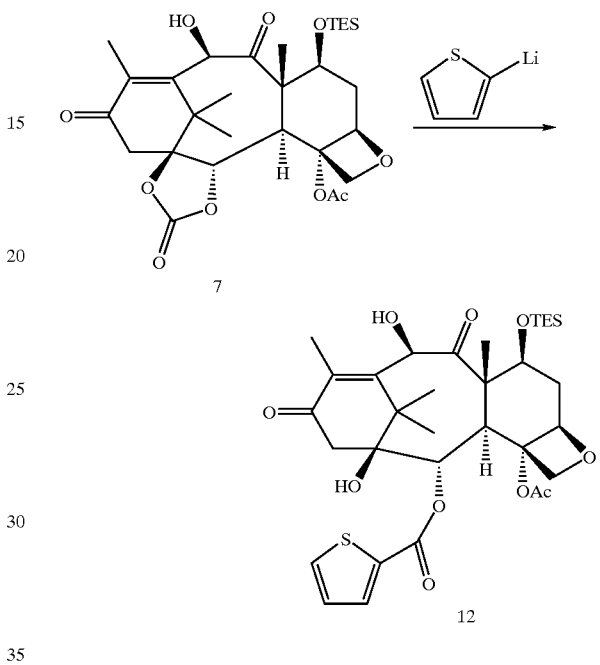

Alcohol 12. A solution of carbonate 7 (50.0 mg, 0.0864 mmol) in tetrahydrofuran (5 mL) at −78° C. was treated with 2-thienyllithium from Aldrich Chemical Company, inc. (1.30 mL of a 1.0 M solution in tetrahydrofuran, 1.30 mmol) and stirred for 0.5 hour. The reaction mixture was poured into a mixture of diethylether (10 mL) and aqueous NH$_4$Cl (5 mL). The organic layer was separated and the aqueous layer was extracted with diethylether (2×10 mL). The combined organic layer was washed with brine (10 mL), dried (MgSO$_4$), concentrated, and purified by flash chromatography (silica, 10→35% ethylacetate in hexanes) to give 7 (16.5 mg, 33%), 12 (36.8 mg, 96% based on 67% conversion) as an amorphous solid.

Physical Data for Alcohol 12. $R_f$=0.56 (silica, 50% ethylacetate in hexanes); IR (film) $v_{max}$ 3403, 2945, 2881, 1717, 1669, 1520, 1413, 1360, 1248, 1078; $^1$H NMR (500 MHz, CDCl$_3$) δ7.84 (dd, J=3.5, 1.0 Hz, 1 H, thiophene), 7.64 (d, J=1.0, 5.0 Hz, 1 H, thiophene), 7.14 (dd, J=5.0, 3.5 Hz, 1 H, thiophene), 5.53 (br d, J=6.5 Hz, 1 H, 2-H), 5.29 (d, J=2.5 Hz, 1 H, 10-H), 4.90 (br d, J=7.5 Hz, 1 H, 5-H), 4.44 (d, J=8.5 Hz, 1 H, 20-H), 4.35 (dd, J=10.5, 6.5 Hz, 1 H, 7-H), 4.29 (d, J=2.5 Hz, 1 H, 10-OH), 4.19 (d, J=8.5 Hz, 1 H, 20-H), 3.90 (d, J=6.5 Hz, 1 H, 3-H), 2.89 (d, J=19.5 Hz, 1 H, 14-H), 2.62 (d, J=19.5 Hz, 1 H, 14-H), 2.49–2.43 (m, 1 H, 6-H), 2.15 (s, 3 H, Me), 2.07 (s, 3 H, Me), 1.92–1.84 (m, 1 H, 6-H), 1.73 (s, 1 H, OH), 1.71 (s, 3 H, Me), 1.21 (s, 3 H, Me), 1.13 (s, 3 H, Me), 0.91 (t, J=8.0 Hz, 9 H, OSi(CH$_2$CH$_3$)$_3$), 0.56–0.49 (band, 6 H, OSi(CH$_2$CH$_3$)$_3$); FAB HRMS (NBA) m/e 663.2655, M+H$^+$ calcd for C$_{33}$H$_{46}$O$_{10}$SSi 663.2659.

Preparation of 3-thiophenyl-C-2 ester derivatives (Alcohol 13 and 14)

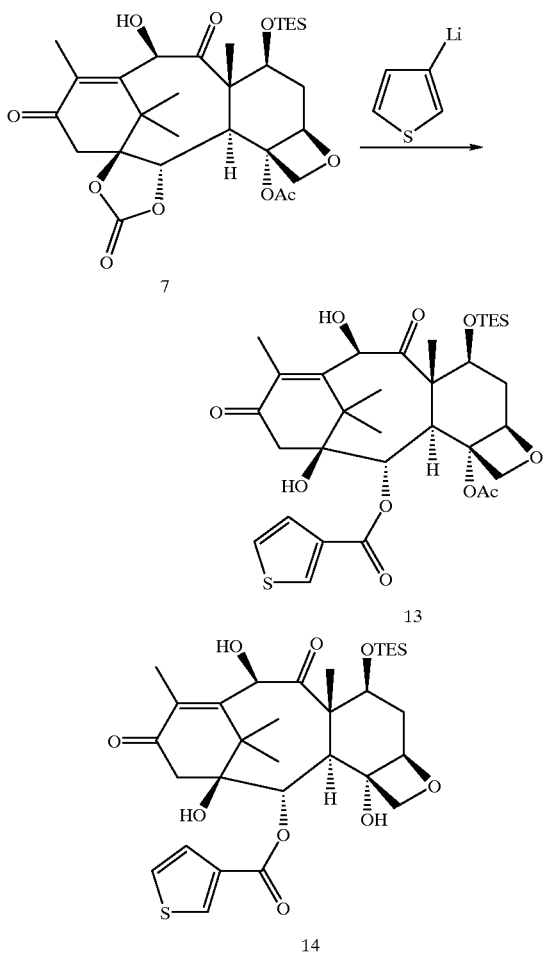

J=14.5, 9.5, 6.5 Hz, 1 H, 6-H), 2.18 (s, 3 H, Me), 2.10 (s, 3 H, Me), 1.89 (ddd, J=14.5, 10.5, 2.0 Hz, 1 H, 6-H), 1.81 (br s, 1 H, OH), 1.72 (s, 3 H, Me), 1.23 (s, 3 H, Me), 1.15 (s, 3 H, Me), 0.93 (t, J=8.0 Hz, 9 H, OSi(CH$_2$CH$_3$)$_3$), 0.62–0.48 (band, 6 H, Si(CH$_2$CH$_3$)$_3$); FAB HRMS (NBA/CsI) m/e 795.1640, M+Cs$^+$ calcd for C$_{33}$H$_{46}$O$_{10}$SSi 795.1635.

Physical Data for Alcohol 14: R$_f$=0.54 (silica, 50% ethylacetate in hexanes); IR (thin film) v$_{max}$ 3437, 3108, 2955, 2880, 1709, 1674, 1605, 1520, 1410, 1360, 1258, 1194, 1103, 1004, 829, 744 cm$^{-1}$; $^1$H NMR (500 MHz, CDCl$_3$) δ8.15 (dd, J=3.0, 1.0 Hz, 1 H, thiophene), 7.49 (dd, J=5.0, 1.0 Hz, 1 H, thiophene), 7.35 (dd, J=5.0, 3.0 Hz, 1 H, thiophene), 5.59 (d, J=6.0 Hz, 1 H, 2-H), 5.27 (d, J=2.5 Hz, 1 H, 10-H), 4.73 (dd, J=9.5, 3.5 Hz, 1 H, 5-H), 4.40 (d, J=8.5 Hz, 1 H, 20-H), 4.32 (d, J=2.5 Hz, 1 H, 10-OH), 4.15 (d, J=8.5 Hz, 1 H, 20-H), 3.92 (dd, J=11.5, 6.0 Hz, 1 H, 7-H), 3.44 (d, J=19.5 Hz, 1 H, 14-H), 3.30 (d, J=6.0 Hz, 1 H, 3-H), 2.91 (br s, 1 H, OH), 2.61 (d, J=19.5 Hz, 1 H, 14-H), 2.38 (ddd, J=14.5, 9.5, 6.0 Hz, 1 H, 6-H), 2.09 (s, 3 H, Me), 1.99 (ddd, J=14.5, 11.5, 3.5 Hz, 1 H, 6-H), 1.81 (br s, 1 H, OH), 1.65 (s, 3 H, Me), 1.24 (s, 3 H, Me), 1.16 (s, 3 H, Me), 0.91 (t, J=8.0 Hz, 9 H, OSi(CH$_2$CH$_3$)$_3$), 0.60–0.46 (band, 6 H, OSi(CH$_2$CH$_3$)$_3$); FAB HRMS (NBA/CsI) m/e 753.1530, M+Cs$^+$ calcd for C$_{31}$H$_{44}$O$_9$SSi 753.1530.

Preparation of 2-pyridinyl-C-2 ester derivatives (Alcohol 15, 16 and triol 6)

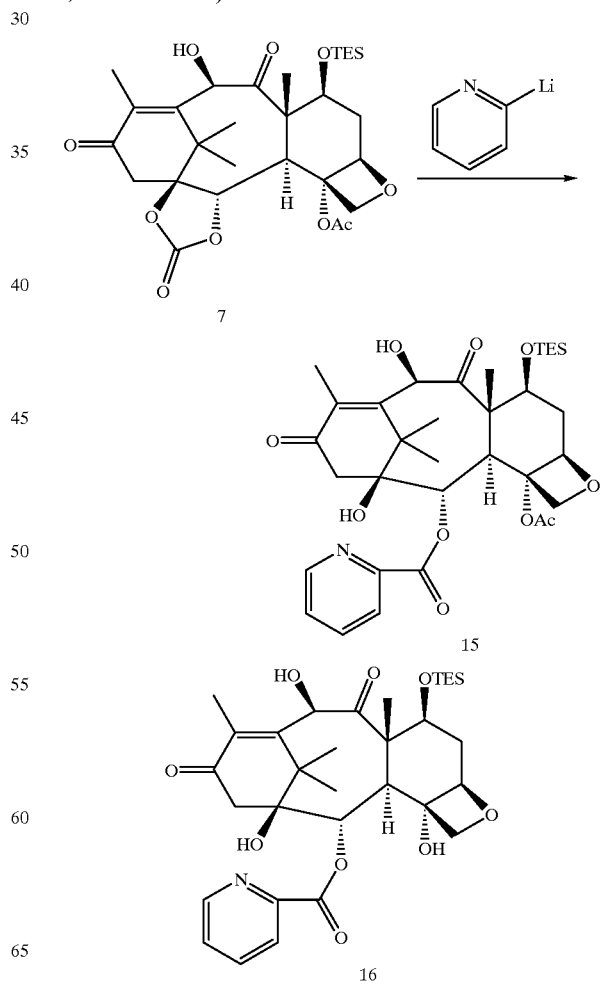

Alcohols 13 and 14. A solution of carbonate 7 (107.9 mg, 0.186 mmol) in tetrahydrofuran (6.2 mL) at −78° C. was treated with 3-thienyllithium (2.76 mL of a 0.41 M solution in diethylether tetrahydrofuran:hexanes (4.5:1:2), 1.13 mmol, prepared from 3-bromothiophene and n-Butyllithium; methodology from Camici, L.; Ricci, A.; Taddei, M. *Tetrahedron Lett.* 1986, 27, 5155) and stirred for 1.5 hour The reaction mixture was poured into a mixture of CH$_2$Cl$_2$ (15 mL) and aqueous NH$_4$Cl (20 mL), the organic layer was separated, and the aqueous layer was extracted with CH$_2$Cl$_2$ (2×10 mL). The combined organic layer was washed with brine (10 mL), dried (MgSO$_4$), concentrated, and purified by flash chromatography (silica, 20→30% ethylacetate in hexanes) to give 7 (16.9 mg, 16%), 13 (87.0 mg, 83% based on 84% conversion), and hydrolyzed C4 acetate 14 (C4-hydrolyzed side product, 9.7 mg, 10% based on 84% conversion) as amorphous solids.

Physical Data for Alcohol 13. R$_f$=0.74 (silica, 50% ethylacetate in hexanes), 0.41 (silica, 10% ethylacetate in benzene, 3 elutions); IR (thin film) v$_{max}$ 3442, 3110, 2956, 2882, 1725, 1672, 1410, 1368, 1244, 1198, 1101, 988, 825, 744 cm$^{-1}$; $^1$H NMR (500 MHz, CDCl$_3$) δ8.18 (dd, J=3.0, 1.2 Hz, 1 H, thiophene), 7.54 (dd, J=5.0, 1.2 Hz, 1 H, thiophene), 7.37 (dd, J=5.0, 3.0 Hz, 1 H, thiophene), 5.56 (dd, J=6.5, 1.0 Hz, 1 H, 2-H), 5.31 (d, J=2.5 Hz, 1 H, 10-H), 4.92 (dd, J=7.5, 2.0 Hz, 1 H, 5-H), 4.40–4.34 (m, 2 H, 20-H, 7-H), 4.31 (d, J=2.5 Hz, 1 H, 10-OH), 4.15 (d, J=8.5 Hz, 1 H, 20-H), 3.93 (d, J=6.5 Hz, 1 H, 3-H), 2.88 (d, J=20 Hz, 1 H, 14-H), 2.63 (dd, J=20.0, 1.0 Hz, 1 H, 14-H), 2.47 (ddd,

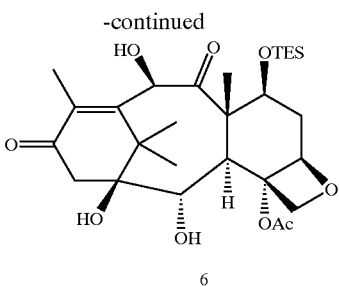

6

Alcohol 15 and 16, and triol 6. A solution of carbonate 7 (62.6 mg, 0.108 mmol) in tetrahydrofuran (5.4 mL) at −78° C. was treated with 2-lithiopyridine (1.15 mL of a 0.44 M solution in diethylether-pentane 1:1, 0.506 mmol, prepared from 2-bromopyridine and t-Butyllithium; methodology from Malmberg, H.; Nilsson, M. *Tetrahedron*, 1986, 42, 3981) and stirred for 1.3 hour The reaction mixture was poured into a mixture of ethylacetate (10 mL) and aqueous $NH_4Cl$ (5 mL), the organic layer was separated, and the aqueous layer was extracted with ethylacetate (2×10 mL). The combined organic layer was washed with brine (5 mL), dried ($MgSO_4$), concentrated, and purified by flash chromatography (silica, 70→100% ethylacetate in petroleum ether) to give 6 (16.3 mg, 27%), 15 (28.0 mg, 39%), and 16 (8.4 mg, 13%) as amorphous solids.

Physical Data for Alcohol 15. $R_f$=0.60 (silica, ethylacetate); $^1H$ NMR (500 MHz, $CDCl_3$) δ8.77 (ddd, J=4.5, 1.7, 1.0 Hz, 1 H, pyridine), 8.05 (br d, J=7.5 Hz, 1 H, pyridine), 7.89 (ddd, J=7.5, 7.5, 1.7 Hz, 1 H, pyridine), 7.53 (ddd, J=7.5, 4.5, 1.0 Hz, 1 H, pyridine), 5.61 (dd, J=6.5, 1.0 Hz, 1 H, 2-H), 5.33 (d, J=2.5 Hz, 1 H, 10-H), 4.92 (dd, J=9.5, 2.0 Hz, 1 H, 5-H), 4.39 (dd, J=10.5, 6.5 Hz, 1 H, 7-H), 4.36 (d, J=9.0 Hz, 1 H, 20-H), 4.33 (d, J=2.5 Hz, 1 H, 10-OH), 4.28 (d, J=9.0 Hz, 1 H, 20-H), 3.96 (d, J=6.5 Hz, 1 H, 3-H), 2.98 (d, J=20.0 Hz, 1 H, 14-H), 2.71 (dd, J=20.0, 1.0 Hz, 1 H, 14-H), 2.50 (s, 1 H, OH), 2.48 (ddd, J=14.5, 9.5, 6.5 Hz, 1 H, 6-H), 2.15 (s, 3 H, Me), 2.11 (s, 3 H, Me), 1.90 (ddd, J=14.5, 10.5, 2.0 Hz, 1 H, 6-H), 1.76 (s, 3 H, Me), 1.24 (s, 3 H, Me), 1.16 (s, 3 H, Me), 0.93 (t, J=8.0 Hz, 9 H, $OSi(CH_2CH_3)_3$), 0.63–0.47 (band, 6 H, $OSi(CH_2CH_3)_3$); FAB HRMS (NBA/CsI) m/e 790.2060, M+Cs$^+$ calcd for $C_{34}H_{47}O_{10}NSi$ 790.2024.

Physical Data for Alcohol 16. $R_f$=0.45 (silica, ethylacetate); IR (film) $v_{max}$ 3435, 2954, 2879, 1732, 1674, 1589, 1362, 1305, 1241, 1116, 998, 829, 741 cm$^{-1}$; $^1H$ NMR (500 MHz, $CDCl_3$) δ8.73 (br d, J=4.5 Hz, 1 H, pyridine), 8.15 (br d, J=7.5 Hz, 1 H, pyridine), 7.90 (ddd, J=7.5, 7.5, 1.7 Hz, 1 H, pyridine), 7.56 (ddd, J=7.5, 4.5, 1.0 Hz, 1 H, pyridine), 5.53 (dd, J=7.5, 1.0, 1 H, 2-H), 5.30 (d, J=2.5 Hz, 1 H, 10-H), 4.84 (dd, J=9.5, 3.0 Hz, 1 H, 5-H), 4.81 (br s, 1 H, OH), 4.31 (d, J=2.5 Hz, 1 H, 10-OH), 4.25 (s, 2 H, 20-$CH_2$), 3.97 (dd, J=11.5, 6.5 Hz, 1 H, 7-H), 3.31 (d, J=19.5 Hz, 1 H, 14-H), 3.23 (d, J=7.5 Hz, 1 H, 3-H), 2.57 (br d, J=19.5 Hz, 1 H, 14-H), 2.43 (ddd, J=14.5, 9.5, 6.5 Hz, 1 H, 6-H), 2.11 (s, 3 H, Me), 1.95 (ddd, J=14.5, 11.5, 3.0 Hz, 1 H, 6-H), 1.92 (br s, 1 H, OH), 1.70 (s, 3 H, Me), 1.24 (s, 3 H, Me), 1.17 (s, 3 H, Me), 0.91 (t, J=8.0 Hz, 9 H, $OSi(CH_2CH_3)_3$), 0.60–0.46 (band, 6 H, $OSi(CH_2CH_3)_3$).

Physical Data for Triol 6. $R_f$=0.24 (silica, 50% ethylacetate in hexanes); IR (thin film) $v_{max}$ 3414, 2957, 2881, 1727, 1664, 1370 cm$^{-1}$; $^1H$ NMR (500 MHz, $CDCl_3$) δ5.23 (d, J=9.5 Hz, 1 H, 10-H), 4.89 (d, J=9.5 Hz, 1 H, 5-H), 4.63 (d, J=9.5 Hz, 1 H, 20-H), 4.56 (d, J=9.5 Hz, 1 H, 20-H), 4.32 (dd, J=11.0, 7.0 Hz, 1 H, 7-H), 4.28 (d, J=2.5 Hz, 1 H, 10-OH), 3.89 (dd, J=6.5, 4.0 Hz, 1 H, 2-H), 3.57 (d, J=6.5 Hz, 1 H, 3-H), 2.78 (d, J=19.5 Hz, 1 H, 14-H), 2.58 (d, 4.0 Hz, 1 H, 2-OH), 2.52 (d, J=19.5 Hz, 1 H, 14-H), 2.49–2.42 (m, 1 H, 6-H), 2.03 (s, 3 H, Me), 1.92–1.84 (m, 1 H, 6-H), 1.68 (s, 3 H, Me), 1.21 (s, 3 H, Me), 1.04 (s, 3 H, Me), 0.90 (t, J=8.0 Hz, 9 H, $Si(CH_2CH_3)_3$), 0.60–0.40 (band, 6 H, $Si(CH_2CH_3)_3$); $^{13}C$ NMR (125 MHz, $CDCl_3$) δ208.9, 198.5, 170.1, 156.7, 138.8, 83.8, 81.2, 77.6, 75.7, 72.8, 72.5, 58.8, 45.8, 43.1, 42.8, 37.3, 32.7, 21.6, 17.5, 13.6, 9.7, 6.7, 5.1; FAB HRMS (NBA/NaI) m/e 575.2648, M+Na$^+$ calcd for $C_{28}H_{44}O_9Si$ 575.2652.

Preparation of 3-pyridinyl-C-2 ester derivative (Alcohol 17)

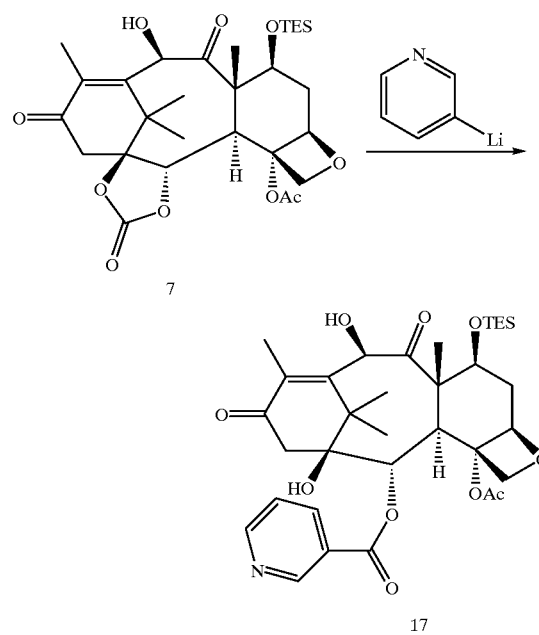

Alcohol 17. To a solution of 3-lithiopyridine (1.15 mmol) in tetrahydrofuran (7 mL), prepared from 3-bromopyridine (Aldrich Chemical Company Inc.) and n-Butyllithium (Aldrich Chemical Company Inc.) at −100° C. (methodology from Parham, W. E.; Piccirilli, R. M. *J. Org. Chem.* 1977, 42, 257), was added a solution of carbonate 7 (133.1 mg, 0.230 mmol) in tetrahydrofuran (2 mL) via cannula. The resulting solution was stirred for 1 h, allowed to warm to −78° C., stirred for 1 h, and poured into a mixture of ethylacetate (10 mL) and aqueous $NH_4Cl$ (10 mL). The organic layer was separated and the aqueous layer was extracted with ethylacetate (2×10 mL). The combined organic layer was washed with brine (10 mL), dried ($MgSO_4$), concentrated, and purified by flash chromatography (silica, 70→95% ethylacetate in petroleum ether) to give 7 (64.8 mg, 49%) and 17 (43.9 mg, 57% based on 51% conversion) as an amorphous solid.

Physical Data for Alcohol 17. $R_f$=0.56 (silica, ethylacetate); IR (film) $v_{max}$ 3435, 2956, 2882, 1731, 1671, 1592, 1366, 1280, 1240, 1109, 991, 824, 739 cm$^{-1}$; $^1H$ NMR (500 MHz, $CDCl_3$) δ9.24 (br s, 1 H, pyridine), 8.81 (d, J=1.0, 4.5 Hz, 1 H, pyridine), 8.30 (ddd, J=8.0, 2.0, 2.0 Hz, 1 H, pyridine), 7.44 (dd, J=8.0, 4.5 Hz, 1 H, pyridine), 5.66 (d, J=6.5 Hz, 1 H, 2-H), 5.32 (s, 1 H, 10-H), 4.92 (dd, J=9.5, 2.0 Hz, 1 H, 5-H), 4.38 (dd, J=10.5, 6.5 Hz, 1 H, 7-H), 4.32 (br s, 1 H, OH), 4.30 (d, J=8.5 Hz, 1 H, 20-H), 4.13 (d, J=8.5 Hz, 1 H, 20-H), 3.96 (d, J=6.5 Hz, 1 H, 3-H), 2.92 (d, J=19.5 Hz, 1 H, 14-H), 2.66 (d, J=19.5 Hz, 1 H, 14-H), 2.48 (ddd, J=15.5, 9.5, 6.5 Hz, 1 H, 6-H), 2.18 (s, 3 H, Me), 2.10 (s, 3 H, Me), 2.03 (s, 1 H, OH), 1.89 (ddd, J=14.5, 10.5, 2.0 Hz, 1 H, 6-H), 1.72 (s, 3 H, Me), 1.23 (s, 3 H, Me), 1.16 (s, 3 H, Me), 0.92 (t, J=8.0 Hz, 9 H, OSi(CH$_2$CH$_3$)$_3$), 0.62–0.48 (band, 6 H, OSi(CH$_2$CH$_3$)$_3$); FAB HRMS (NBA/CSI) m/e 790.2030, M+Cs$^+$ calcd for C$_{34}$H$_{47}$O$_{10}$NSi 790.2024.

Preparation of 4-N, N-dimethylaniline-C-2 ester derivative (Alcohol 18)

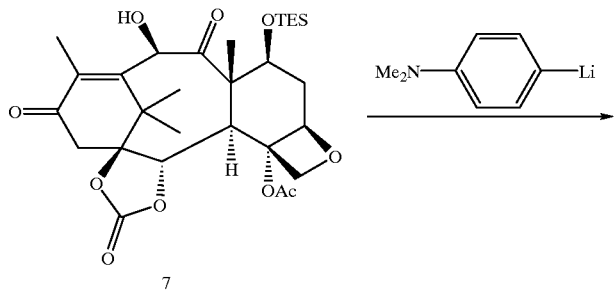

Alcohol 18. A solution of carbonate 7 (150 mg, 0.259 mmol) in tetrahydrofuran (20 mL) at −78° C. was treated with 4-lithio-N,N-dimethylaniline (6.5 mL of a 0.39 M solution in diethylether:pentane (3:1), 2.54 mmol, prepared from 4-bromo-N,N-dimethylaniline and t-Butyllithium; methodology from Jones, F. N.; Hauser, C. R. *J. Org. Chem.* 1962, 27, 4389) and stirred for 15 minutesutes. The reaction mixture was poured into a mixture of CH$_2$Cl$_2$ (35 mL) and aqueous NH$_4$Cl (20 mL), the organic layer was separated, and the aqueous layer was extracted with CH$_2$Cl$_2$ (2×20 mL). The combined organic layer was washed with brine (20 mL), dried (MgSO$_4$), concentrated, and purified by flash chromatography (silica, 10→35% ethylacetate in petroleum ether) to give 18 (55.0 mg, 30%) as an amorphous solid.

Physical Data for Alcohol 18. R$_f$=0.26 (silica, 35% ethylacetate in hexanes); IR (film) v$_{max}$ 3414, 2924, 1706, 1669, 1605, 1530, 1094; $^1$H NMR (500 MHz, CDCl$_3$) δ7.90 (d, J=9.0 Hz, 2 H, Ar), 6.64 (d, J=9.0 Hz, 2 H, Ar), 5.60 (br d, J=7.0 Hz, 1 H, 2-H), 5.29 (d, J=2.5 Hz, 1 H, 10-H), 4.89 (br d, J=9.5 Hz, 1 H, 5-H), 4.37 (d, J=8.5 Hz, 1 H, 20-H), 4.36 (dd, J=10.5, 6.5 Hz, 1 H, 7-H), 4.31 (d, J=2.5 Hz, 1 H, 10-OH), 4.13 (br d, J=8.5 Hz, 1 H, 20-H), 3.90 (d, J=7.0 Hz, 1 H, 3-H), 3.05 (s, 6 H, NMe$_2$), 2.93 (s, 1 H, OH), 2.90 (d, J=20.0 Hz, 1 H, 14-H), 2.61 (br d, J=20.0 Hz, 1 H, 14-H), 2.49–2.40 (m, 1 H, 6-H), 2.16 (s, 3 H, Me), 2.08 (s, 3 H, Me), 1.90–1.83 (m, 1 H, 6-H), 1.69 (s, 3 H, Me), 1.20 (s, 3 H, Me), 1.13 (s, 3 H, Me), 0.90 (t, J=8.0 Hz, 9 H, OSi(CH$_2$CH$_3$)$_3$), 0.56–0.49 (band, 6 H, OSi(CH$_2$CH$_3$)$_3$); FAB HRMS (NBA/NaI) m/e 722.3354, M+Na$^+$ calcd for C$_{37}$H$_{53}$O$_{10}$NSi 722.3336.

Preparation of 1-naphthalene-C-2 ester derivative (Alcohol 19)

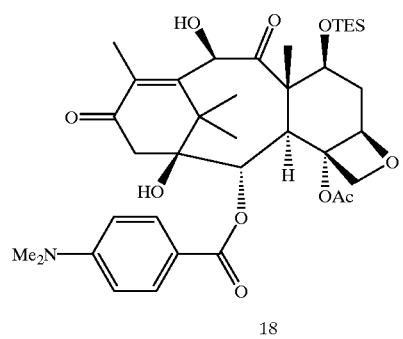

Alcohol 19. A solution of carbonate 7 (47 mg, 0.0812 mmol) in tetrahydrofuran (2 mL) at −78° C. was treated with 1-lithionaphthalene (6.3 mL of a 0.32 M solution in diethylether, 2.03 mmol, prepared from 1-bromonaphthalene from Aldrich Chemical Company Inc.

and tButyllithium; methodology from Gilman, H.; Moore, F. W. *J. Am. Chem. Soc.* 1940, 62, 1843) and stirred for 5 minutesutes. The reaction mixture was poured into a mixture of $CH_2Cl_2$ (15 mL) and aqueous $NH_4Cl$ (20 mL), the organic layer was separated, and the aqueous layer was extracted with $CH_2Cl_2$ (2×10 mL). The combined organic layer was washed with brine (10 mL), dried ($MgSO_4$) and concentrated to give alcohol 19 which was taken into the next step without further purification.

Physical Data for Alcohol 19. $R_f$=0.27 (20% ethylacetate in petroleum ether); IR (film) $v_{max}$ 3442, 2954, 2882, 1724, 1671, 1461, 1362, 1279, 1228, 1195, 1092, 987, 826, 736 cm$^{-1}$; $^1$H NMR (500 MHz, $CDCl_3$) δ8.66 (s, 1 H, naphthalene), 8.07 (dd, J=9.0, 2.0 Hz, 1 H, naphthalene), 7.97–7.89 (m, 3 H, naphthalene), 7.68–7.57 (m, 2 H, naphthalene), 5.71 (br d, J=6.5 Hz, 1 H, 2-H), 5.35 (d, J=2.5 Hz, 1 H, 10-H), 4.94 (br d, J=8.0 Hz, 1 H, 5-H), 4.41 (dd, J=11.0, 7.0 Hz, 1 H, 7-H), 4.37 (d, J=8.5 Hz, 1 H, 20-H), 4.35 (d, J=2.0 Hz, 1 H, 10-OH), 4.18 (d, J=8.5 Hz, 1 H, 20-H), 4.00 (d, J=6.5 Hz, 1 H, 3-H), 3.02 (d, J=19.5 Hz, 1 H, 14-H), 2.69 (d, J=19.5 Hz, 1 H, 14-H), 2.54–2.45 (m, 1 H, 6-H), 2.27 (s, 3 H, Me), 2.13 (s, 3 H, Me), 1.94–1.87 (m, 1 H, 6-H), 1.86 (s, 1 H, OH), 1.75 (s, 3 H, Me), 1.25 (s, 3 H, Me), 1.20 (s, 3 H, Me), 0.94 (t, J=8.0 Hz, 9 H, OSi($CH_2Cl_3$)$_3$), 0.63–0.49 (band, 6 H, OSi($CH_2CH_3$)$_3$); FAB HRMS (NBA) m/e 707.3270, M+H$^+$ calcd for $C_{39}H_{50}O_{10}Si$ 707.3252.

Preparation of phenylacetylide-C-2 ester derivative (Alcohol 20)

Physical Data for Alcohol 20. $R_f$=0.59 (50% ethylacetate in hexanes); $^1$H NMR (300 MHz, $CDCl_3$) δ7.63–7.57 (m, 2 H, Ar), 7.53–7.27 (m, 3 H, Ar), 5.43 (d, J=6.5 Hz, 1 H, 2-H), 5.28 (d, J=2.5 Hz, 1 H, 10-H), 4.90 (br d, J=7.5 Hz, 1 H, 5-H), 4.67 (d, J=8.5 Hz, 1 H, 20-H), 4.44 (d, J=8.5 Hz, 1 H, 20-H), 4.37–4.30 (m, 1 H, 7-H), 4.28 (d, J=2.5 Hz, 1 H, 10-OH), 3.88 (d, J=6.5 Hz, 1 H, 3-H), 2.85 (d, J=20.2 Hz, 1 H, 14-H), 2.63 (d, J=20.2 Hz, 1 H, 14-H), 2.55–2.47 (m, 1 H, 6-H), 2.11 (s, 3 H, OAc), 2.08 (s, 3 H, 18-Me), 1.94–1.85 (m, 1 H, 6-H), 1.67 (s, 3 H, Me), 1.41 (s, 3 H, Me), 1.21 (s, 3 H, Me), 0.91 (t, J=8.0 Hz, 9 H, OSi($CH_2CH_3$)$_3$), δ0.59–0.42 (band, 6 H, OSi($CH_2CH_3$)$_3$).

Preparation of Hydroxycarbamate-C-2 ester derivative (Alcohol 21)

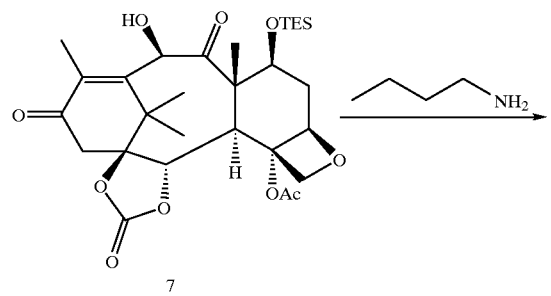

7

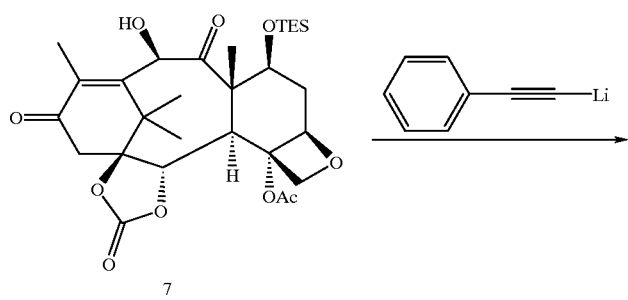

7

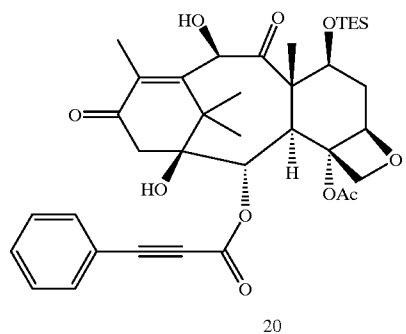

20

Alcohol 20. A solution of carbonate 7 (5.0 mg, 0.00864 mmol) in tetrahydrofuran (0.5 mL) at −78° C. was treated with lithium phenylacetylide from Aldrich Chemical Company Inc. (0.13 mL of a 1.0 M solution in tetrahydrofuran, 0.13 mmol) and stirred for 0.5 hour The reaction mixture was treated with aqueous $NH_4Cl$ (0.5 mL), allowed to warm to 25° C., and diluted with $H_2O$ (5 mL) and diethylether (5 mL). The organic layer was separated, dried, and concentrated to give a 9:1 mixture of carbonate 7 and alcohol 20 (5.0 mg, 95%) as a film.

-continued

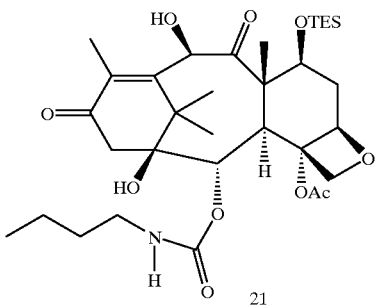

Alcohol 21. A solution of carbonate 7 (5.0 mg, 0.00864 mmol) in MeOH (0.5 mL) at 25° C. was treated with n-Butyl-NH$_2$ from Aldrich Chemical Company Inc. (0.05 mL, 0.506 nmmol) and stirred for 10 minutes. The reaction mixture was concentrated and purified by flash chromatography (silica, 30→50% ethylacetate in petroleum ether) to give 21 (5.2 mg, 92%) as an amorphous solid.

Physical Data for Alcohol 21. R$_f$=0.13 (silica, 30% ethylacetate in petroleum ether); IR (film) v$_{max}$ 3434, 2957, 2881, 1711, 1671, 1368, 1243, 1108, 987, 829 cm$^{-1}$; $^1$H NMR (500 MHz, CDCl$_3$) δ5.27 (d, J=2.0 Hz, 1 H, 10-H), 5.23 (d, J=6.5 Hz, 1 H, 2-H), 4.91 (br d, J=8.0 Hz, 1 H, 5-H). 4.79 (t, J=6.0 Hz, 1 H, NH), 4.47 (d, J=8.5 Hz, 1 H, 20-H), 4.34 (dd, J=11.0, 7.0 Hz, 1 H, 7-H), 4.30 (d, J=2.5 Hz, 1 H, 10-OH), 4.28 (d, J=8.5 Hz, 1 H, 20-H), 3.78 (d, J=6.5 Hz, 1 H, 3-H), 3.29–3.12 (m, 2 H, NHCH$_2$), 2.70 (d, J=20.0 Hz, IH, 14-H), 2.60 (d, J=20.0 Hz, 1 H, 14-H), 2.51–2.42 (m, 1 H, 6-H), 2.24 (s, 1 H, OH), 2.06 (s, 3 H, Me), 2.05 (s, 3 H, Me), 1.94–1.86 (m, 1 H, 6-H), 1.69 (s, 3 H, Me), 1.55–1.46 (m, 2 H, NHCH$_2$CH$_2$), 1.40–1.30 (m, 2 H, NHCH$_2$CH$_2$CH$_2$), 1.21 (s, 3 H, Me), 1.09 (s, 3 H, Me), 0.95–0.80 (m, 12 H, CH$_3$ of Bu, OSi(CH$_2$CH$_3$)$_3$), 0.61–0.47 (band, 6 H, OSi(CH$_2$CH$_3$)$_3$); FAB HRMS (NBA/NaI) m/e 674.3336, M+Na$^+$ calcd for C$_{33}$H$_{53}$O$_{10}$NSi 674.3336.

Preparation of NN-methyl-phenyl-hydroxycarbamate-C-2 ester derivative (Alcohol 22)

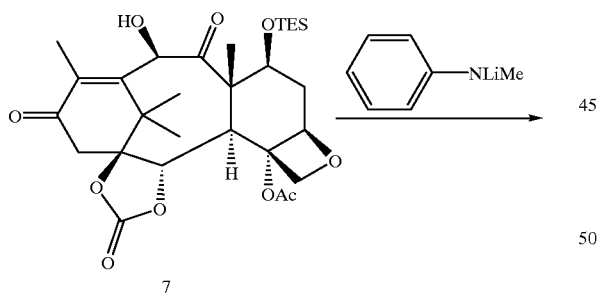

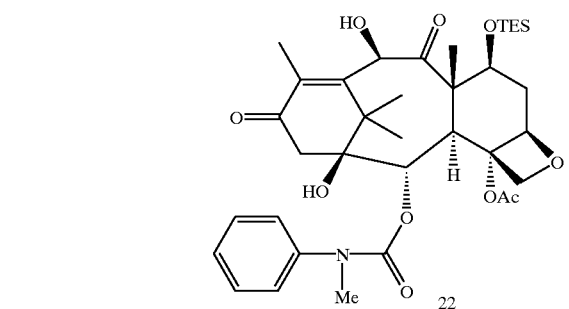

Alcohol 22. A solution of carbonate 7 (5.0 mg, 0.00864 mmol) in tetrahydrofuran (0.5 mL) at −78° C. was treated with LiNMePh (0.2 mL of a 0.47 M solution in diethylether, 0.094 mmol, prepared from N-methylaniline (Aldrich) and n-Butyllithium) and stirred for 1.25 hour. The reaction mixture was poured into a mixture of diethylether (5 mL) and aqueous NH$_4$Cl (5 mL), the organic layer was separated, and the aqueous layer was extracted with diethylether (2×5 mL). The combined organic layer was washed with brine (5 mL), dried (MgSO$_4$), concentrated, and purified by flash chromatography (silica, 15→35% ethylacetate in hexanes) to give 7 (2.5 mg, 50%) and 22 (2.8 mg, 93% based on 50% conversion) as an amorphous solid.

Physical Data for Alcohol 22. R$_f$=0.22 (silica 35% ethylacetate in petroleum ether); $^1$H NMR (500 MHz, CDCl$_3$) δ7.45–7.18 (band, 5 H), 5.25 (br d, J=6.5 Hz, 1 H, 2-H), 5.20 (d, J=2.5 Hz, 1 H, 10-H), 4.70 (br d, J=8.0 Hz, 1 H, 5-H), 4.26 (d, J=2.5 Hz, 1 H, 10-OH), 4.22 (dd, J=10.5, 6.5 Hz, 1 H, 7-H), 4.19 (d, J=8.5 Hz, 1 H, 20-H), 4.16 (d, J=8.5 Hz, 1 H, 20-H), 3.58 (d, J=7.0 Hz, 1 H, 3-H), 3.27 (s, 3 H, MeN), 2.52 (d, J=20.0 Hz, 1 H, 14-H), 2.35 (d, J=20.0 Hz, 1 H, 14-H), 2.40–2.31 (m, 1 H, 6-H), 2.03 (s, 1 H, OH), 1.97 (s, 3 H, Me), 1.85–1.76 (m, 1 H, 6-H), 1.66 (s, 3 H, Me), 1.57 (s, 3 H, Me), 1.18 (s, 3 H, Me), 1.08 (s, 3 H, Me), 0.87 (t, J=8.0 Hz, 9 H, OSi(CH$_2$CH$_3$)$_3$), 0.55–0.43 (band, 6 H, OSi(CH$_2$CH$_3$)$_3$); FAB HRMS (NBA) m/e 686.3358, M+H$^+$ calcd for C$_{36}$H$_{51}$O$_{10}$NSi 686.3361.

Preparation of Thioether-C-2 ester derivative (Alcohol 23)

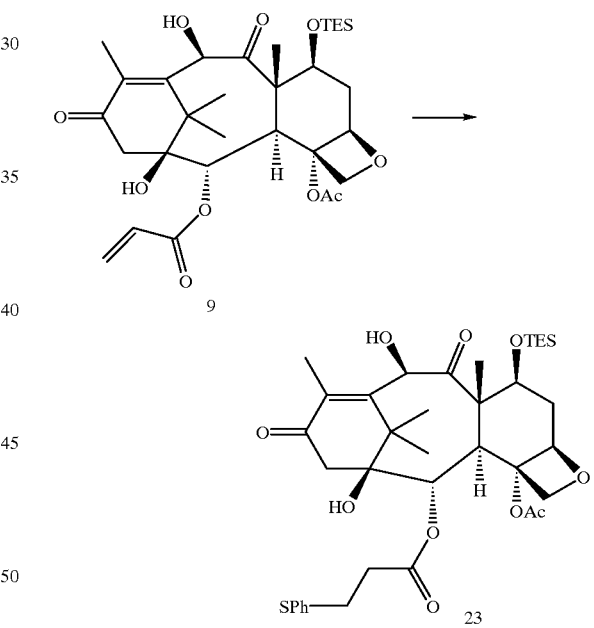

Alcohol 23. A solution of vinyl ester 9 (55.6 mg, 0.0916 mmol) and 4-dimethylaminutesopyridine from Aldrich Chemical Company Inc. (DMAP, 1.8 mg, 0.0147 mmol) in CH$_2$Cl$_2$ (4.3 mL) at 25° C. was treated with PhSH from Aldrich Chemical Company Inc. (0.030 mL, 0.292 mmol) and stirred for 1.5 hour The reaction mixture was concentrated and purified by flash chromatography (silica, 30% ethylacetate in petroleum ether) to give 23 (58.1, 88%) as a white solid.

Physical Data for Alcohol 23. R$_f$=0.37 (silica, 30% ethylacetate in hexanes), 0.34 (10% ethylacetate in PhH, 2 elutions); IR (film) v$_{max}$ 3441, 3057, 2956, 2883, 1732, 1672, 1600, 1367, 1238, 1111, 988, 825, 739 cm$^{-1}$; $^1$H NMR (500 MHz, CDC$_{13}$) δ7.39–7.24 (band, 5 H), 5.44 (d, J=6.5

Hz, 1 H, 2-H), 5.28. (d, J=2.5 Hz, 1 H, 10-H), 4.90 (dd, J=9.5, 2.0 Hz, 1 H, 5-H), 4.38 (d, J=8.0 Hz, 1 H, 20-H), 4.33 (dd, J=10.5, 6.5Hz, 1 H, 7-H), 4.29 (d, J=2.5 Hz, 1 H, 10-OH), 4.18 (d, J=8.0 Hz, 1 H, 20-H), 3.83 (d, J=6.5 Hz, 1 H, 3-H), 3.24–3.13 (m, 2 H, CH$_2$SPh), 2.76 (d, J=19.5 Hz, 1 H, 14-H), 2.72–2.58 (m, 3 H, 14-H, CH$_2$CH$_2$SPh), 2.47 (ddd, J=14.5, 9.5, 6.5 Hz, 1 H, 6-H), 2.39 (s, 1 H, OH), 2.07 (s, 3 H, Me), 2.05 (s, 3 H, Me), 1.89 (ddd, J=14.5, 10.5, 2.0 Hz, 1 H, 6-H), 1.68 (s, 3 H, Me), 1.23 (s, 3 H, Me), 1.12 (s, 3 H, Me), 0.92 (t, J=8.0 Hz, 9 H, OSi(CH$_2$CH$_3$)$_3$), 0.61–0.47 (band, 6 H, OSi(CH$_2$CH$_3$)$_3$); FAB HRMS (NBA/CsI) m/e 849.2085, M+Cs$^+$ calcd for C$_{37}$H$_{52}$O$_{10}$SSi 849.2105.

Preparation of intermediates 25–27 and 2-furanyl-C-2-taxoid (28)

3 H, Me), 2.14 (s, 3 H, Me), 1.90–1.83 (m, 1 H, 6-H), 1.65 (s, 3 H, Me), 1.25 (s, 3 H, Me), 1.18 (s, 3 H, Me), 0.91 (t, J=8.0 Hz, 9 H, OSi(CH$_2$CH$_3$)$_3$), 0.64–0.52 (band, 6 H, OSi(CH$_2$CH$_3$)$_3$); FAB HRMS (NBA/CsI) m/e 821.1966, M+Cs$^+$ calcd for C$_{35}$H$_{48}$O$_{12}$Si 821.1969.

Alcohol 26. A solution of enone 25 (36 mg, 0.0523 mmol) in MeOH (3 mL) containing two drops of CH$_3$COOH at 0° C. was treated with NaBH$_4$ (200 mg, 5.29 mmol, added by portions) and stirred for 6 h. The reaction mixture was diluted with CH$_2$Cl$_2$ (10 mL), treated with aqueous NH$_4$Cl (5 mL), and stirred for 10 min. The organic layer was separated and the aqueous layer was extracted with CH$_2$Cl$_2$ (2×10 mL). The combined organic layer was washed with brine (5 mL), dried (MgSO$_4$), concentrated, and purified by

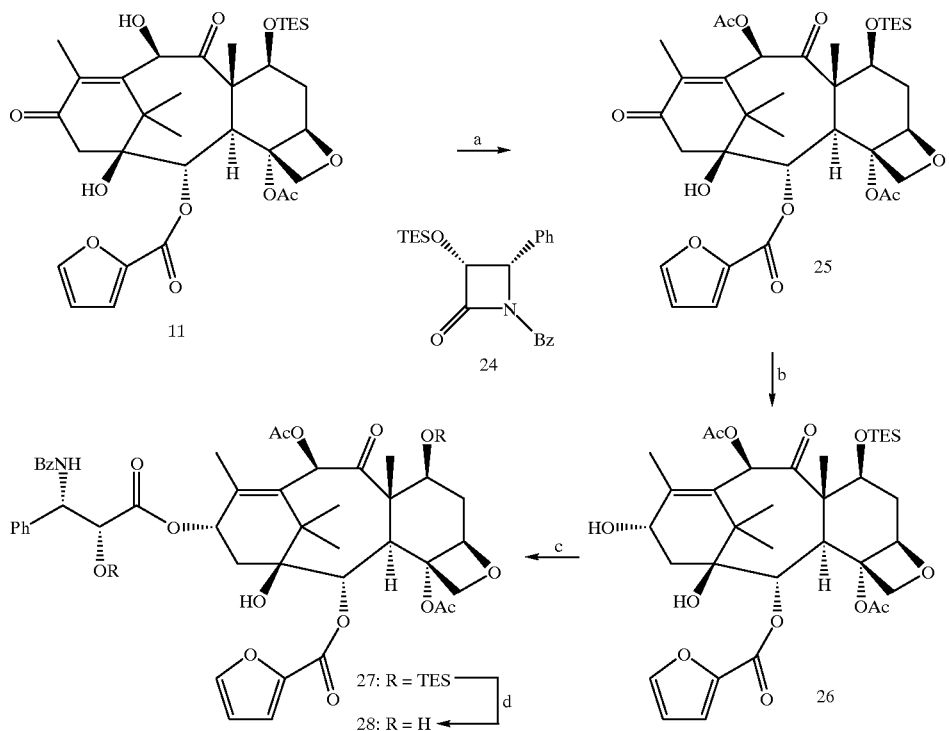

Acetate 25. A solution of alcohol 11 and 4-dimethylaminopyridine (DMAP, 100 mg, 0.819 mnmol) in CH$_2$Cl$_2$ (3 mL) at 25° C. was treated with acetic anhydride (0.50 mL, 5.30 mmol) and stirred for 3 h. The reaction mixture was diluted with CH$_2$Cl$_2$ (5 mL), treated with aqueous NaHCO$_3$ (7 mL), and stirred vigorously for 25 min. The organic layer was separated and the aqueous layer was extracted with CH$_2$Cl$_2$ (2×10 mL). The combined organic layer was washed with brine (5 mL), dried (MgSO$_4$), concentrated, and purified by preparative TLC (silica, 10% ethylacetate in benzene, 3 elutions) to give 25 (36 mig, 66% from carbonate 7) as a white foam.

Physical Data for Acetate 25. R$_f$=0.38 (20% ethylacetate in petroleum ether); IR (film) v$_{max}$ 3509, 2956, 2881, 1727, 1674, 1469, 1371, 1299, 1227, 1108, 746 cm$^{-1}$; $^1$H NMR (500 MHz, CDCl$_3$) δ7.65 (br s, 1 H, furan), 7.24 ( br d, J=3.0 Hz, 1 H, furan), 6.58–6.54 (m, 2 H, 10-H, furan), 5.59 (d, J=6.5 Hz, 1 H, 2-H), 4.92 (br d, J=7.5 Hz, 1 H, 5-H), 4.46 (dd, J=10.5, 6.5 Hz, 1 H, 7-H), 4.42 (d, J=8.5 Hz, 1 H, 20-H), 4.16 (d, J=8.5 Hz, 1 H, 20-H), 3.87 (d, J=6.5 Hz, 1 H, 3-H), 2.89 (d, J=20.0 Hz, 1 H, 14-H), 2.63 (d, J=20.0 Hz, 1 H, 14-H), 2.59–2.48 (m, 1 H, 6-H), 2.22 (s, 3 H, Me), 2.17 (s, preparative TLC (silica, 50% ethylacetate in petroleum ether) to give 26 (30 mg, 83% ) as an amorphous solid.

Physical Data for Alcohol 26. R$_f$=0.42 (silica, 50% ethylacetate in petroleum ether); $^1$H NMR (300 MHz, CDCl$_3$) δ7.62 (br s, 1 H, furan), 7.25 (d, J=3.5 Hz, 1 H, furan), 6.58 (d, J=3.5 Hz, 1 H, furan), 6.43 (s, 1 H, 10-H), 5.51 (d, J=7.0 Hz, 1 H, 2-H), 4.96 (d, J=7.5 Hz, 1 H, 5-H), 4.85–4.79 (m, 1 H, 13-H), 4.48 (dd, J=10.5, 7.5 Hz, 1 H, 7-H), 4.38 (d, J=8.0 Hz, 1 H, 20-H), 4.15 (d, J=8.0 Hz, 1 H, 20-H), 3.82 (d, J=7.0 Hz, 1 H, 3-H), 2.61–2.48 (m, 2 H, 6-H and 14-H), 2.28 (s, 3 H, OAc), 2.20–2.10 (m, 1 H, 14-H), 2.18 (s, 6 H, OAc and 18-Me), 1.98–1.80 (m, 1 H, 6-H), 1.18 (s, 3 H, 16-Me), 1.04 (s, 3 H, 17-Me), 0.90 (t, J=8.0 Hz, 9 H, OSi(CH$_2$CH$_3$)$_3$), 0.65–0.50 (band, 6 H, OSi(CH$_2$CH$_3$)$_3$).

DiTES taxoid 27. To a solution of alcohol 26 (30.0 mg, 0.0434 mmol, previously azeotroped twice with benzene) and β-lactam 24 (28.0 mg, 0.0734 mmol, previously azeotroped twice with benzene) in THF (2 mL), prepared from the Ojima-Holton protocol (Holton, R. A. ChemAbstr. 1990, 114, 164568q; Ojima, I.; Habus, I.; Zhao, M.; Georg, G. I.; Jayasinghe, L. R. J. Org. Chem. 1991, 56, 1681–1683; Ojima, I.; Habus, I.; Zhao, M.; Zucco, M.; Park, Y. H.; Sun, C. M.; Brigaud, T. *Tetrahedron* 1992, 48, 6985–7012), at 0° C. was added NaN(SiMe$_3$)$_2$ (0.130 mL of a 1.0 M solution in THF, 0.130 mmol) dropwise. The resulting solution was stirred for 5 min and poured into a mixture of CH$_2$Cl$_2$ (10 mL) and aqueous NH$_4$Cl (5 mL). The organic layer was separated and the aqueous layer was extracted with CH$_2$Cl$_2$ (2×5 mL). The combined organic layer was washed with brine (5 mL), dried (MgSO$_4$), concentrated, and purified by preparative TLC (silica, 60% ethylacetate in petroleum ether) to give 27 (12 mg, 26%) as an amorphous solid which was taken directly into the next step.

Taxoid 28. A solution of silyl ether 27 (6 mg, 0.00560 mmol) in THF (1 mL) at 25° C. was treated with HF·pyridine (1 mL) and stirred for 1 h. The reaction mixture was poured into a mixture of ethylacetate (10 mL) and aqueous NaHCO$_3$ (10 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by preparative TLC (silica, 60% ethylacetate in petroleum ether) to give 28 (3 mg, 64%) as a colorless film.

Physical Data for Taxoid 28. R$_f$=0.1 (50% ethylacetate in petroleum ether); IR (film) v$_{max}$ 3383, 2933, 2898, 1729, 1649, 1519, 1242, 1110, 1071 cm$^{-1}$; $^1$H NMR (500 MHz, CDCl$_3$) δ7.77–7.73 (m, 2 H), 7.68–7.66 (m, 1 H, furan), 7.55–7.33 (band, 9 H), 6.98 (d, J=30 9.0 Hz, 1 H, NH), 6.58 (dd, J=3.5, 1.5 Hz, 1 H, furan), 6.27–6.21 (m, 2 H, 10-H, 13-H), 5.80 (dd, J=9.0, 2.0 Hz, 1 H, 3'-H), 5.57 (d, J=7.0 Hz, 1 H, 2-H), 4.96 (dd, J=10.0, 2.0 Hz, 1 H, 5-H), 4.80 (d, J=2.0 Hz, 1 H, 2'-H), 4.43–4.37 (m, 2 H, 7-H, 20-H), 4.24 (d, J=8.5 Hz, 1 H, 20-H), 3.77 (d, J=7.0 Hz,1 H, 3-H), 2.60–2.52 (m, 1 H, 6-H), 2.47 (d, J=4.0 Hz, 1 H, OH), 2.38 (s, 3 H, Me), 2.35–2.21 (m, 2 H, 14-CH$_2$), 2.25 (s, 3 H, Me), 1.94–1.86 (m, 1 H, 6-H), 1.81 (br s, 3 H, Me), 1.76 (s, 1 H, OH), 1.68 (s, 3 H, Me), 1.25 (s, 3 H, Me), 1.13 (s, 3 H, Me).

Preparation of 2-thiophenyl-C-2 taxol (32)

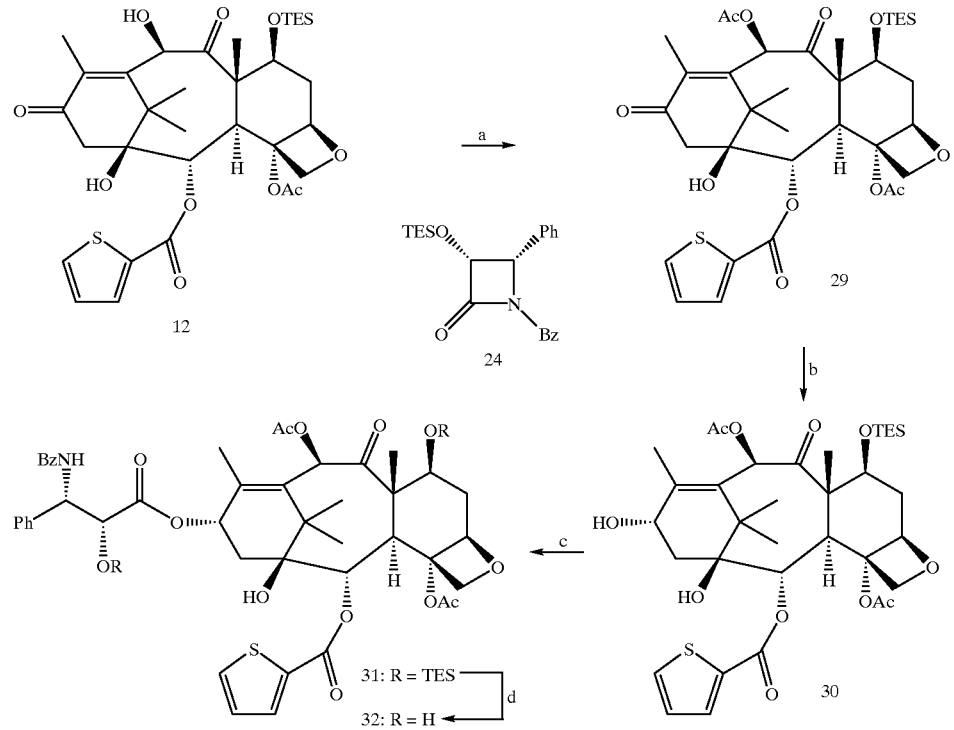

Acetate 29. A solution of alcohol 12 (36.0 mg, 0.0543 mmol) and 4-dimethylaminopyridine (DMAP, 33.0 mg, 0.270 mmol) in CH$_2$Cl$_2$ (3.0 mL) at 25° C. was treated with acetic anhydride (0.50 mL, 5.30 mmol) and stirred for 1 h. The reaction mixture was diluted with CH$_2$Cl$_2$ (10 mL), treated with aqueous NaHCO$_3$ (7 mL), and stirred vigorously for 0.5 h. The organic layer was separated and the aqueous layer was extracted with CH$_2$Cl$_2$ (2×10 mL). The combined organic layer was washed with brine (5 mL), dried (MgSO$_4$), concentrated, and purified by flash chromatography (silica, 10→35% ethylacetate in hexanes) to give 29 (29.5 mg, 77%) as an amorphous solid.

Physical Data for Acetate 29. R$_f$=0.56 (silica, 50% ethylacetate in petroleum ether); IR (film) v$_{max}$ 3457, 2956, 1712, 1669, 1525, 1413, 1376, 1264, 1227, 1073; $^1$H NMR (500 MHz, CDCl$_3$) δ7.84 (dd, J=4.0, 1.5 Hz, 1 H, thiophene), 7.63 (dd, J=5.0, 1.5 Hz, 1 H, thiophene), 7.13 (dd, J=5.0, 4.0 Hz, 1 H, thiophene), 6.56 (s, 1 H, 10-H), 5.58 (br d, J=6.5 Hz, 1 H, 2-H), 4.90 (br d, J=8.0 Hz, 1 H, 5-H), 4.44 (dd, J=10.5, 7.0 Hz, 1 H, 7-H), 4.42 (d, J=8.5 Hz, 1 H, 20-H), 4.18 (d, J=8.5 Hz, 1 H, 20-H), 3.85 (d, J=6.5 Hz, 1 H, 3-H), 2.91 (d, J=19.5 Hz, 1 H, 14-H), 2.64 (dd, J=19.5, 1.0 Hz, 1 H, 14-H), 2.55–2.48 (m, 1 H, 6-H), 2.20 (s, 3 H, Me), 2.15 (s, 3 H, Me), 2.14 (s, 3 H, Me), 1.89–1.82 (m, 1

H, 6-H), 1.65 (s, 3 H, Me), 1.23 (s, 3 H, Me), 1.16 (s, 3 H, Me), 0.88 (t, J=8.0 Hz, 9 H, OSi(CH$_2$CH$_3$)$_3$), 0.59–0.53 (band, 6 H, OSi(CH$_2$CH$_3$)$_3$); FAB HRMS (NBA/CsI) m/e 837.1736, M+Cs$^+$ calcd for C$_{35}$H$_{48}$O$_{11}$SSi 837.1741.

Alcohol 30. A solution of enone 29 (29.0 mg, 0.0411 mmol) in MeOH (5 mL) at 0° C. was treated with NaBH$_4$ (30.2 mg, 0.80 mmol, added by portions) and stirred for 2.5 h. The reaction mixture was diluted with CH$_2$Cl$_2$ (15 mL), treated with aqueous NH$_4$Cl (5 mL), and stirred for 10 min. The organic layer was separated and the aqueous layer was extracted with CH$_2$Cl$_2$ (2×10 mL). The combined organic layer was washed with brine (5 mL), dried (MgSO$_4$), concentrated, and purified by flash chromatography (silica, 25→50% ethylacetate in petroleum ether) to give 29 (4.0 mg, 14%) and 30 (14.7 mg, 59% based on 86% conversion) as an amorphous solid.

Physical Data for Alcohol 30. R$_f$=0.34 (silica, 50% ethylacetate in petroleum ether); IR (film) v$_{max}$ 3478, 2946, 2892, 1717, 1520, 1365, 1238, 1083; $^1$H NMR (500 MHz, CDCl$_3$) δ7.85 (dd, J=3.5, 1.5 Hz, 1 H, thiophene), 7.61 (dd, J=5.0, 1.5 Hz, 1 H, thiophene), 7.12 (dd, J=5.0, 3.5 Hz, 1 H, thiophene), 6.43 (s, 1 H, 10-H), 5.51 (d, J=7.0 Hz, 1 H, 2-H), 4.94 (br d, J=7.5 Hz, 1 H, 5-H), 4.83–4.77 (m, 1 H, 13-H), 4.45 (dd, J=10.5, 7.5 Hz, 1 H, 7-H), 4.41 (d, J=8.0 Hz, 1 H, 20-H), 4.19 (br d, J=8.0 Hz, 1 H, 20-H), 3.82 (d, J=7.0 Hz, 1 H, 3-H), 2.55–2.48 (m, 1 H, 6-H), 2.24 (s, 3 H, Me), 2.26–2.21 (m, 2 H, 14-CH$_2$), 2.16 (d, J=1.0 Hz, 3 H, 18-Me), 2.15 (s, 3 H, Me), 2.00 (d, J=5.0 Hz, 1 H, OH), 1.90–1.82 (m, 1 H, 6-H), 1.66 (s, 3 H, Me), 1.58 (s, 1 H, OH), 1.15 (s, 3 H, Me), 1.02 (s, 3 H, Me), 0.90 (t, J=8.0 Hz, 9 H, OSiCH$_2$CH$_3$)$_3$), 0.59–0.55 (band, 6 H, OSi(CH$_2$CH$_3$)$_3$); FAB HRMS (NBA/CsI) m/e 839.1893, M+Cs$^+$ calcd for C$_{35}$H$_{50}$O$_{11}$SSi 839.1897.

DITES taxoid 31. To a solution of alcohol 30 (14.5 mg, 0.0205 mmol, previously azeotroped twice with benzene) and β-lactam 24 (16.0 mg, 0.0420 mmol, previously azeotroped twice with benzene) in THF (1.0 mL), prepared from the Ojima-Holton protocol (Holton, R. A. Chem Abstr. 1990, 114, 164568q; Ojima, I.; Habus, I.; Zhao, M.; Georg, G. I.; Jayasinghe, L. R. J. Org. Chem. 1991, 56, 1681–1683; Ojima, I.; Habus, I.; Zhao, M.; Zucco, M.; Park, Y. H.; Sun, C. M.; Brigaud, T. Tetrahedron 1992, 48, 6985–7012), at −78° C. was added NaN(SiMe$_3$)$_2$ (0.051 mnL of a 1.0 M solution in THF, 0.051 mmol) dropwise. The resulting solution was stirred for 0.5 h and poured into a mixture of diethylether (10 mL) and aqueous NH$_4$Cl (5 mL). The organic layer was separated and the aqueous layer was extracted with diethylether (2×5 mL). The combined organic layer was washed with brine (5 mL), dried (MgSO$_4$), concentrated, and purified by flash chromatography (silica, 10→35% ethylacetate in hexanes) followed by preparative TLC (silica, 15% ethylacetate in benzene) to give 30 (3.0 mg, 21%) and 31 (7.6 mg, 43% based on 79% conversion) as a white solid.

Physical Data for DITES taxoid 31. R$_f$=0.48 (silica, 50% ethylacetate in hexanes); IR (film) v$_{max}$ 3382, 2913, 2850, 1722, 1653, 1461, 1243, 1083, 1014; $^1$H NMR (500 MHz, CDCl$_3$) δ7.90 (br d, J=4.0 Hz, 1 H, thiophene), 7.74 (d, J=8.0 Hz, 2 H, NBz), 7.62 (br d, J=5.0 Hz, 1 H, thiophene), 7.48 (t, J=7.0 Hz, 1 H, Ar), 7.42–7.28 (band, 7 H, Ar), 7.14 (dd, J=5.0, 4.0 Hz, 1 H, thiophene), 7.10 (d, J=9.0 Hz, 1 H, NH), 6.42 (s, 1 H, 10-H), 6.20 (br t, J=9.0 Hz, 1 H, 13-H), 5.65 (br d, J=9.0 Hz, 1 H, 3'-H), 5.57 (d, J=7.0 Hz, 1 H, 2-H), 4.94 (br d, J=8.5 Hz, 1 H, 5-H), 4.67 (d, J=1.5 Hz, 1 H, 2'-H), 4.44 (dd, J=11.0, 6.5 Hz, 1 H, 7-H), 4.43 (d, J=8.5 Hz, 1 H, 20-H), 4.26 (d, J=8.5 Hz, 1 H, 20-H), 3.77 (d, J=7.0 Hz, 1 H, 3-H), 2.51 (s, 3 H, Me), 2.54–2.47 (m, 1 H, 6-H), 2.34 (dd, J=15.0, 9.5 Hz, 1 H, 14-H), 2.15 (s, 3 H, Me), 2.10 (dd, J=15.0, 9.0, 1 H, 14-H), 1.99 (s, 3 H, Me), 1.93–1.86 (m, 1 H, 6-H), 1.72 (s, 1 H, OH), 1.68 (s, 3 H, Me), 1.18 (s, 3 H, Me), 1.16 (s, 3 H, Me), 0.90 (t, J=8.0 Hz, 9 H, Si(CH$_2$Cl$_3$)$_3$), 0.79 (t, J=8.0 Hz, 9 H, Si(CH$_2$CH$_3$)$_3$), 0.57–0.55 (band, 6 H, Si(CH$_2$CH$_3$)$_3$), 0.45–0.40 (band, 6 H, Si(CH$_2$CH$_3$)$_3$); FAB HRMS (NBA/CsI) m/e 1220.3685 M+Cs$^+$ calcd for C$_{57}$H$_{77}$O$_{14}$NSSi$_2$ 1220.3658.

Taxoid 32. A solution of silyl ether 31 (7.5 mg, 0.00689 mmol) in THF (0.8 mL) at 25° C. was treated with HF•pyridine (0.150 mL) and stirred for 1 h. The reaction mixture was poured into a mixture of ethylacetate (10 mL) and aqueous NaHCO$_3$ (5 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by flash chromatography (silica, 50→100% ethylacetate in petroleum ether) to give 32 (4.2 mg, 71%) as a colorless film.

Physical Data for Taxoid 32. R$_f$=0.44 (silica, 75% ethylacetate in petroleum ether); IR (film) v$_{max}$ 3417, 2929, 1716, 1649, 1521, 1460, 1417, 1368, 1247, 1076; $^1$H NMR (500 MHz, CDCl$_3$) δ7.90 (dd, J=4.0, 1.0 Hz, 1 H, thiophene), 7.73 (d, J=7.0 Hz, 2 H, NBz), 7.63 (dd, J=5.0, 1.0 Hz, 1 H, thiophene), 7.51–7.32 (band, 8 H, Ar), 7.14 (dd, J=5.0, 4.0 Hz, 1 H, thiophene), 6.96 (d, J=9.0 Hz, 1 H, NH), 6.24 (s, 1 H, 10-H), 6.19 (br t, J=9.0 Hz, 1 H, 13-H), 5.75 (dd, J=9.0, 2.5 Hz, 1 H, 3'-H), 5.55 (d, J=7.0 Hz, 1 H, 2-H), 4.94 (br d, J=8.0 Hz, 1 H, 5-H), 4.76 (dd, J=5.0, 2.5 Hz, 1 H, 2'-H), 4.41 (d, J=8.5 Hz, 1 H, 20-H), 4.40–4.33 (m, 1 H, 7-H), 4.24 (d, J=8.5 Hz, 1 H, 20-H), 3.73 (d, J=7.0 Hz, 1 H, 3-H), 3.52 (d, J=5.0 Hz, 1 H, 2'-OH), 2.58–2.49 (m, 1 H, 6-H), 2.44 (d, J=4.0 Hz, 1 H, 7-OH), 2.35 (s, 3 H, Me), 2.29 (d, J=9.0 Hz, 2 H, 14-CH$_2$), 2.22 (s, 3 H, Me), 1.91–1.83 (m, 1 H, 6-H), 1.76 (s, 3 H, Me), 1.66 (s, 3 H, Me), 1.23 (s, 3 H, Me), 1.10 (s, 3 H, Me); FAB HRMS (NBA/CsI) m/e 992.1252, M+Cs$^+$ calcd for C$_{45}$H$_{49}$NO$_{14}$S 992.1928.

Preparation of 3-thiophenyl-C-2 taxol (36)

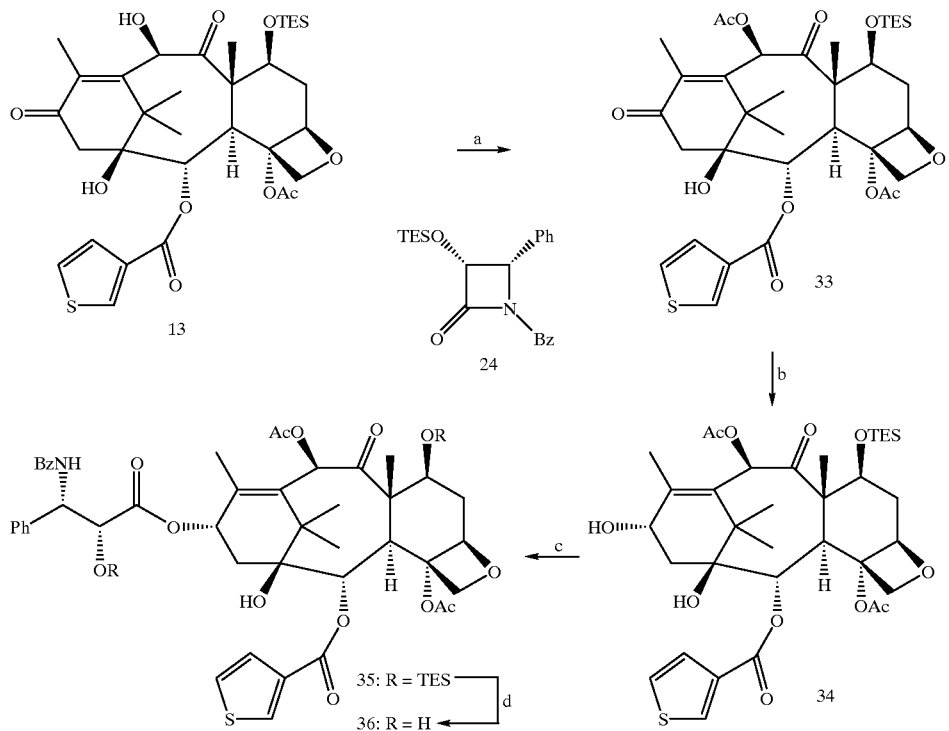

Acetate 33. A solution of alcohol 13 (68.4 mg, 0.103 mmol) and 4-dimethylaminopyridine (DMAP, 37.8 mg, 0.309 mmol) in $CH_2Cl_2$ (4.4 mL) at 25° C. was treated with acetic anhydride (0.370 mL, 3.92 mmol) and stirred for 2 h. The reaction mixture was diluted with $CH_2Cl_2$ (5 mL), treated with aqueous $NaHCO_3$ (7 mL), and stirred vigorously for 25 min. The organic layer was separated and the aqueous layer was extracted with $CH_2Cl_2$ (2×10 mL). The combined organic layer was washed with brine (5 mL), dried ($MgSO_4$), concentrated, and purified by flash chromatography (silica, 30% ethylacetate in hexanes) to give 33 (66.0 mg, 91%) as an amorphous solid.

Physical Data for Acetate 33. $R_f$=0.48 (silica, 10% ethylacetate in benzene, 3 elutions); IR (film) $v_{max}$ 3518, 2956, 2881, 1727, 1676, 1520, 1460, 1371, 1236, 1098, 985, 824, 744 cm$^{-1}$; $^1$H NMR (500 MHz, $CDCl_3$) δ8.19 (dd, J=3.0, 1.1 Hz, 1 H, thiophene), 7.55 (dd, J=5.0, 1.1 Hz, 1 H, thiophene), 7.38 (dd, J=5.0, 3.0 Hz, 1 H, thiophene), 6.58 (s, 1 H, 10-H), 5.61 (dd, J=6.5, 0.7 Hz, 1 H, 2-H), 4.92 (dd, J=9.5, 2.0 Hz, 1 H, 5-H), 4.47 (dd, J=10.5, 6.5 Hz, 1 H, 7-H), 4.38 (d, J=8.5 Hz, 1 H, 20-H), 4.14 (d, J=8.5 Hz, 1 H, 20-H), 3.88 (d, J=6.5 Hz, 1 H, 3-H), 2.89 (d, J=20 Hz, 1 H, 14-H), 2.64 (br d, J=20 Hz, 1 H, 14-H), 2.54 (ddd, J=14.5, 9.5, 6.5 Hz, 1 H, 6-H), 2.23 (s, 3 H, Me), 2.18 (s, 3 H, Me), 2.17 (s, 3 H, Me), 1.87 (ddd, J=14.5, 10.5, 2.0, 1 H, 6-H), 1.85 (s, 1 H, OH), 1.66 (s, 3 H, Me), 1.26 (s, 3 H, Me), 1.19 (s, 3 H, Me), 0.92 (t, J=8.0 Hz, 9 H, OSi($CH_2CH_3$)$_3$), 0.65–0.54 (band, 6 H, OSi($CH_2CH_3$)$_3$); FAB HRMS (NBA/CsI) m/e 837.1760, M+Cs$^+$ calcd for $C_{35}H_{48}O_{11}$SSi 837.1741.

Alcohol 34. A solution of enone 33 (57.3 mg, 0.0813 mmol) in MeOH-THF (5:1, 4.1 mL) at 0° C. was treated with $NaBH_4$ (69.1 mg, 1.83 mmol, added by portions) and stirred for 2.5 h. The reaction mixture was diluted with $CH_2Cl_2$ (10 mL), treated with aqueous $NH_4Cl$ (5 mL), and stirred for 10 min. The organic layer was separated and the aqueous layer was extracted with $CH_2Cl_2$ (2×10 mL). The combined organic layer was washed with brine (5 mL), dried ($MgSO_4$), concentrated, and purified by flash chromatography (silica, 30% ethylacetate in hexanes) to give 33 (6.8 mg, 12%) and 34 (45.2 mg, 89% based on 88% conversion) as an amorphous solid.

Physical Data for Alcohol 34. $R_f$=0.48 (silica, 50% ethylacetate in hexanes); IR (film) $v_{max}$ 3520, 2953, 2881, 1719, 1520, 1370, 1238, 1100, 979, 823, 746 cm$^{-1}$; $^1$H NMR (500 MHz, $CDCl_3$) δ8.20 (dd, J=3.0, 1.0 Hz, 1 H, thiophene), 7.57 (dd, J=5.0, 1.0 Hz, 1 H, thiophene), 7.35 (dd, J=5.0, 3.0 Hz, 1 H, thiophene), 6.45 (s, 1 H, 10-H), 5.54 (d, J=7.0 Hz, 1 H, 2-H), 4.96 (br d, J=8.5 Hz, 1 H, 5–25 H), 4.82 (br dd, J=12.0, 8.0 Hz, 1 H, 13-H), 4.48 (dd, J=10.5, 6.5 Hz, 1 H, 7-H), 4.36 (d, J=8.5 Hz, 1 H, 20-H), 4.15 (d, J=8.5 Hz, 1 H, 20-H), 3.85 (d, J=7.0 Hz, 1 H, 3-H), 2.53 (ddd, J=14.5, 9.5, 6.5, 1 H, 6-H), 2.27 (s, 3 H, Me), 2.28–2.21 (m, 2 H, 14-$CH_2$), 2.18 (s, 6 H, Me, Me), 2.03 (s, 1 H, OH), 1.87 (ddd, J=14.5, 10.5, 2.0 Hz, 1 H, 6-H), 1.67 (s, 3 H, Me), 1.65 (s, 1 H, OH), 1.18 (s, 3 H, Me), 1.04 (s, 3 H, Me), 0.92 (t, J=8.0 Hz, 9 H, OSi($CH_2CH_3$)$_3$), 0.64–0.50 (band, 6 H, OSi($CH_2CH_3$)$_3$); FAB HRMS (NBA/CsI) m/e 839.1908 M+Cs$^+$ calcd for $C_{35}H_{50}O_{11}$SSi 839.1897.

DiTES taxoid 35. To a solution of alcohol 34 (19.5 mg, 0.0276 mmol, previously azeotroped twice with benzene) and β-lactam 24 (27.5 mg, 0.0721 mmol, previously azeotroped twice with benzene) in THF (1.4 mL), prepared from the Ojima-Holton protocol (Holton, R. A. *Chem Abstr.* 1990,114, 164568q; Ojima, I.; Habus, I.; Zhao, M.; Georg, G. I.; Jayasinghe, L. R. *J. Org. Chem.* 1991, 56, 1681–1683; Ojima, I.; Habus, I.; Zhao, M.; Zucco, M.; Park, Y. H.; Sun, C. M.; Brigaud, T. *Tetrahedron* 1992, 48, 6985–7012), at 0° C. was added NaN(SiMe$_3$)$_2$ (0.066 mL of a 1.0 M solution in THF, 0.066 mmol) dropwise. The resulting solution was stirred for 0.5 h and poured into a mixture of $CH_2Cl_2$ (10 mL) and aqueous $NH_4Cl$ (5 mL). The organic layer was separated and the aqueous layer was extracted with $CH_2Cl_2$ (2×5 mL). The combined organic layer was washed with brine (5 mL), dried (MgSO$_4$), concentrated, and purified by flash chromatography (silica, 20→30 % ethylacetate in hexanes) to give 34 (1.1 mg, 6%) and 35 (17.3 mg, 61% based on 94% conversion) as a white solid.

Physical Data for DiTES taxoid 35. R$_f$=0.86 (silica, 50% ethylacetate in hexanes); IR (film) v$_{max}$ 3519, 3437, 2953, 2879, 1726, 1666, 1515, 1483, 1369, 1240, 1100, 979, 825, 746 cm$^{-1}$; $^1$H NMR (500 MHz, CDCl$_3$) δ8.32 (dd, J=3.0, 1.2 Hz, 1 H, thiophene), 7.76–7.73 (m, 2 H), 7.60 (dd, J=5.0, 1.2 Hz, 1 H, thiophene), 7.52–7.29 (band, 9 H), 7.10 (d, J=9.0 Hz, 1 H, NH), 6.44 (s, 1 H, 10-H), 6.26 (br t, J=9.0 Hz, 1 H, 13-H), 5.72 (dd, J=9.0, 2.0 Hz, 1 H, 3'-H), 5.61 (d, J=7.0 Hz, 1 H, 2-H), 4.95 (dd, J=9.5, 2.0 Hz, 1 H, 5-H), 4.70 (d, J=2.0 Hz, 1 H, 2'-H), 4.48 (dd, J=10.5, 6.5 Hz, 1 H, 7-H), 4.37 (d, J=8.5 Hz, 1 H, 20-H), 4.23 (d, J=8.5 Hz, 1 H, 20-H), 3.81 (d, J=7.0 Hz, 1 H, 3-H), 2.56–2.49 (m, 1 H, 6-H), 2.54 (s, 3 H, Me), 2.35 (dd, J=15.5, 9.0 Hz, 1 H, 14-H), 2.17 (s, 3 H, Me), 2.07 (dd, J=15.5, 9.0 Hz, 1 H, 14-H), 2.03 (d, J=1.0 Hz, 3 H, 18-Me), 1.94–1.87 (m, 1 H, 6-H), 1.69 (s, 3 H, Me), 1.68 (s, 1 H, OH), 1.20 (s, 3 H, Me), 1.18 (s, 3 H, Me), 0.93 (t, J=8.0 Hz, 9 H, OSi(CH$_2$CH$_3$)$_3$), 0.81 (t, J=8.0 Hz, 9 H, OSi(CH$_2$CH3)$_3$), 0.63–0.53 (band, 6 H, OSi(CH$_2$CH$_3$)$_3$), 0.52–0.36 (band, 6 H, OSi(CH$_2$CH$_3$)$_3$); FAB HRMS (NBA/CsI) m/e 1220.3675, M+Cs$^+$ calcd for C$_{57}$H$_{77}$O$_{14}$SSi$_2$N 1220.3658.

Taxoid 36. A solution of silyl ether 35 (17.3 mg, 0.0159 mmol) in THF (0.6 mL) at 25° C. was treated with HF-pyridine (0.150 mL) and stirred for 2 h. The reaction mixture was poured into a mixture of ethylacetate (10 mL) and aqueous NaHCO$_3$ (5 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by preparative TLC (silica, 25% ethylacetate in petroleum ether) to give 36 (7.7 mg, 56%) as a colorless film.

Preparation of Taxoid 36. R$_f$=0.11 (silica, 50% ethylacetate in hexanes); IR (film) v$_{max}$ 3496, 3434, 2940, 1723, 1648, 1519, 1370, 1243, 1071, 975 cm$^{-1}$; $^1$H NMR (500 MHz, CDCl$_3$) δ8.32 (dd, J=3.0, 1.0 Hz, 1 H, thiophene), 7.75–7.72 (m, 2 H), 7.60 (dd, J=5.0, 1.0 Hz, 1 H, thiophene), 7.53–7.33 (band, 9 H), 6.95 (d, J=9.0 Hz, 1 H, NH), 6.28–6.23 (m, 2 H, 10-H, 13-H), 5.81 (dd, J=9.0, 2.0 Hz, 1 H, 3'-H), 5.58 (d, J=7.0 Hz, 1 H, 2-H), 4.95 (dd, J=9.5, 2.0 Hz, 1 H, 5-H), 4.80 (dd, J=4.5, 2.0 Hz, 1 H, 2'-H), 4.41 (br t, J=7.5 Hz, 1 H, 7-H), 4.36 (d, J=8.5 Hz, 1 H, 20-H), 4.22 (d, J=8.5 Hz, 1 H, 20-H), 3.78 (d, J=7.0 Hz, 1 H, 3-H), 3.49 (d, J=4.5 Hz, 1 H, 2'-OH), 2.55 (ddd, J=14.5, 9.5, 6.5 Hz, 1 H, 6-H), 2.45 (br s, 1 H, OH), 2.40 (s, 3 H, Me), 2.34 (dd, J=15.5, 9.0 Hz, 1 H, 14-H), 2.25 (dd, J=15.5, 9.0 Hz, 1 H, 14-H), 2.24 (s, 3 H, Me), 1.89 (ddd, J=14.5, 11.0, 2.0 Hz, 1 H, 6-H), 1.81 (d, J=2.0 Hz, 3 H, 18-Me), 1.74 (br s, 1 H, OH), 1.67 (s, 3 H, Me), 1.24 (s, 3 H, Me), 1.13 (s, 3 H, Me); FAB HRMS (NBA/CsI) m/e 992.1940, M+Cs$^+$ calcd for C$_{45}$H$_{49}$O$_{14}$NS 992.1928.

Preparation of 2-pyridinyl-C-2 taxol (40)

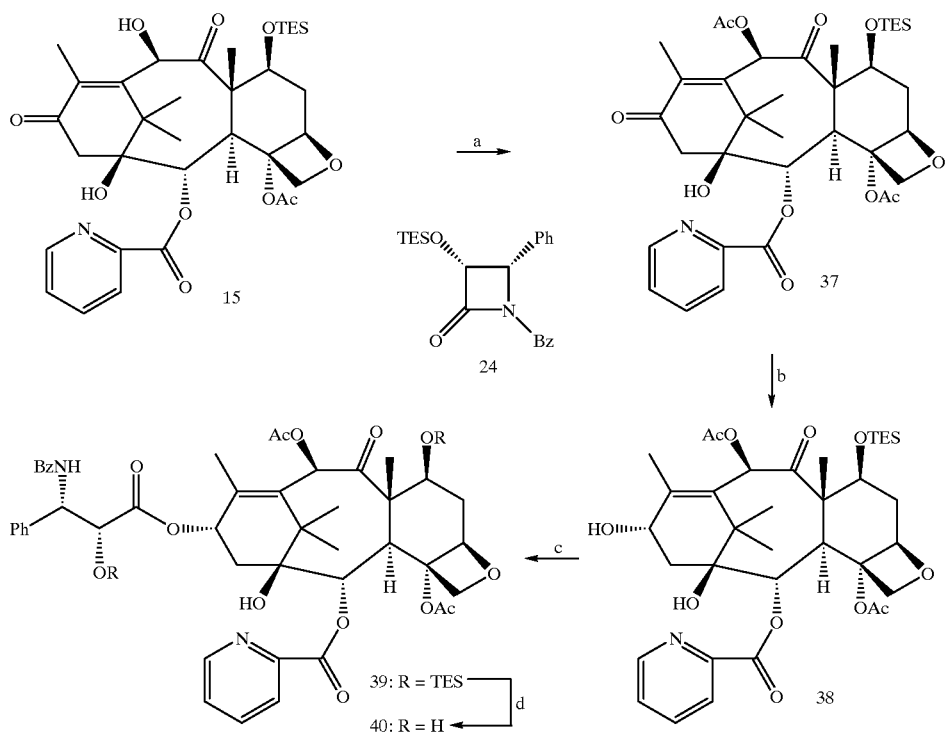

Acetate 37. A solution1 of alcohol 15. (23.2 mg, 0.0353 mnmol) and 4-dimethylaminopyridine (DMAP, 12.9 mg, 0.106 mnmol) in CH$_2$Cl$_2$ (1.5 mL) at 25° C. was treated with acetic anhydride (0.126 mL, 1.34 mmol) and stirred for 2 h. The reaction mixture was diluted with ethylacetate (5 mL), treated with aqueous NaHCO$_3$ (7 mL), and stirred vigorously for 25 min. The organic layer was separated and the aqueous layer was extracted with ethylacetate (2×10 mL). The combined organic layer was washed with brine (5 mL), dried (MgSO$_4$), concentrated, and purified by flash chromatography (silica, 70→100% ethylacetate in petroleum ether) to give 37 (19.0 mg, 77%) as an amorphous solid.

Preparation of Acetate 37. $R_f$=0.58 (silica, ethylacetate); IR (film) $V_{max}$ 3482, 2954, 2881, 1730, 1675, 1370, 1304, 1231, 1118, 987, 823, 739 cm$^{-1}$; $^1$H NMR (500 MHz, CDCl$_3$) δ8.77 (ddd, J=4.5, 1.7, 1.0 Hz, 1 H, pyridine), 8.05 (ddd, J=8.0, 1.0, 1.0 Hz, 1 H. pyridine), 7.89 (ddd, J=8.0, 8.0, 1.7 Hz, 1 H, pyridine), 7.53 (ddd, J=8.0, 4.5, 1.0 Hz, 1 H, pyridine), 6.59 (s, 1 H, 10-H), 5.65 (dd, J=6.6, 1.0 Hz, 1 H, 2-H), 4.92 (dd, J 9.5, 2.0 Hz, 1 H, 5-H), 4.48 (dd, J=10.5, 7.0 Hz, 1 H, 7-H), 4.35 (d, J=8.5 Hz, 1 H, 20-H), 4.26 (dd, J=8.5, 1.0 Hz, 1 H, 20-H), 3.91 (d, J=6.5 Hz, 1 H, 3-H), 3.00 (d, J=20.0 Hz, 1 H, 14-H), 2.71 (dd, J=20.0, 1.0 Hz, 1 H, 14-H), 2.54 (ddd, J=14.5, 9.5, 7.0 Hz, 1 H, 6-H), 2.53 (s, 1 H, OH), 2.23 (s, 3 H, Me), 2.18 (s, 3 H, Me), 2.14 (s, 3 H, Me), 1.88 (ddd, J=14.5, 10.5, 2.0 Hz, 1 H, 6-H), 1.70 (s, 3 H, Me), 1.27 (s, 3 H, Me), 1.20 (s, 3 H, Me), 0.92 (t, 9 H, J=8.0 Hz, OSi(CH$_2$CH$_3$)$_3$), 0.64–0.52 (band, 6 H, OSi(CH$_2$CH$_3$)$_3$); FAB HRMS (NBA/CsI) m/e 832.2139, M+Cs$^+$ calcd for C$_{36}$H$_{49}$O$_{11}$NSi 832.2129.

Alcohol 38. A solution of enone 37 (47.6 mg, 0.0680 mmol) in MeOH-THF (5 1, 3.8 mL) at 0° C. was treated with NaBH$_4$ (46.0 mg, 1.22 mmol, added by portions) and stirred for 1.5 h. The reaction mixture was diluted with ethylacetate (10 mL), treated with aqueous NH$_4$Cl (5 mL), and stirred for 10 min. The organic layer was separated and the aqueous layer was extracted with ethylacetate (2×10 mL). The combined organic layer was washed with brine (5 mL), dried (MgSO$_4$), concentrated, and purified by flash chromatography (basic alumina, ethylacetate →10% MeOH in ethylacetate) to give 27f (28.0 mg, 59%) as an amorphous solid.

Physical Data for Alcohol 38. $R_f$=0.36 (silica, ethylacetate); IR (film) $v_{max}$ 3487, 2951, 2880, 1736, 1583, 1369, 1307, 1236, 1132, 983, 824, 739 cm$^{-1}$; $^1$H NMR (500 MHz, CDCl$_3$) δ8.79 (dm, J=4.5 Hz, 1 H, pyridine), 8.13 (br d, J=7.5 Hz, 1 H, pyridine), 7.88 (ddd, J=7.5, 7.5, 1.7 Hz, 1 H, pyridine), 7.51 (ddd, J=7.5, 4.5, 1.0 Hz, 1 H, pyridine), 6.46 (s, 1 H, 10-H), 5.64 (d, J=7.0 Hz, 1 H, 2-H), 4.96 (dd, J=9.5, 2.0 Hz, 1 H, 5-H), 4.85 (br t, J=8.0 Hz, 1 H, 13-H), 4.49 (dd, J=10.5, 6.5 Hz, 1 H, 7-H), 4.31 (d, J=8.0 Hz, IH, 20-H), 4.25 (d, J=8.0 Hz, 1 H, 20-H), 3.89 (d, J=7.0 Hz, 1 H, 3-H), 2.53 (ddd, J=14.5, 9.5, 6.5 Hz, 1 H, 6-H), 2.36–2.11 (m, 2 H, 14-CH$_2$), 2.25 (s, 3 H, Me), 2.19 (d, J=1.0 Hz, 3 H, 18-Me), 2.18 (s, 3 H, Me), 1.88 (ddd, J=14.0, 10.5, 2.5 Hz, 1 H, 6-H), 1.70 (s, 3 H, Me), 1.20 (s, 3 H, Me), 1.05 (s, 3 H, Me), 0.92 (t, J=8.0 Hz, 9 H, OSi(CH$_2$CH$_3$)$_3$), 0.65–0.51 (band, 6 H, OSi(CH$_2$CH$_3$)$_3$); FAB HRMS (NBA/CsI) m/e 834.2311, M+Cs$^+$ calcd for C$_{36}$H$_{51}$O$_{11}$NSi 834.2286.

DiTES taxoid 39. To a solution of alcohol 38 (10.3 mg, 0.0147 mmol, previously azeotroped twice with benzene) and β-lactam 24 (17.0 mg, 0.0446 mmol, previously azeotroped twice with benzene) in THF (0.75 mL) at 0° C., prepared from the Ojima-Holton protocol (Holton, R. A. *Chem Abstr.* 1990, 114, 164568q; Ojima, I.; Habus, I.; Zhao, M.; Georg, G. I.; Jayasinghe, L. R. *J. Org. Chem.* 1991, 56, 1681–1683; Ojima, I.; Habus, I.; Zhao, M.; Zucco, M.; Park, Y. H.; Sun, C. M.; Brigaud, T. *Tetrahedron* 1992, 48, 6985–7012), was added NaN(SiMe$_3$)$_2$ (0.038 mL of a 1.0 M solution in THF, 0.038 mmol) dropwise. The resulting solution was stirred for 20 min and poured into a mixture of ethylacetate (10 mL) and aqueous NH$_4$Cl (5 mL). The organic layer was separated and the aqueous layer was extracted with ethylacetate (2×5 mL). The combined organic layer was washed with brine (5 mL), dried (MgSO$_4$), concentrated, and purified by preparative TLC (silica, 60% ethylacetate in petroleum ether) to give 39 (2.7 mg, 17%) as a film.

Physical Data for DiTES taxoid 39. $R_f$=0.28 (silica, 50% ethylacetate in hexane); IR (film) $v_{max}$ 3429, 2952, 2927, 2878, 1728, 1662, 1585, 1369, 1236, 1124, 1016, 984, 742 cm$^{-1}$; $^1$H NMR (500 MHz, CDCl$_3$) δ8.78 (br d, J=4.5 Hz, 1 H, pyridine), 8.21 (d, J=8.0 Hz, 1 H, pyridine), 7.95 (ddd, J=8.0, 8.0, 1.7 Hz, 1 H, pyridine), 7.75–7.70 (m, 2 H), 7.54–7.22 (band, 9 H), 7.12 (d, J=9.0 Hz, 1 H, NH), 6.45 (s, 1 H, 10-H), 6.27 (br t, J=9.0 Hz, 1 H, 13-H), 5.73–5.67 (m, 2 H, 2-H, 3'-H), 4.95 (dd, J=9.5, 2.0 Hz, 1 H, 5-H), 4.70 (d, J=2.0 Hz, 1 H, 2'-H), 4.48 (dd, J=10.5, 6.5, 1 H, 7-H), 4.32 (br s, 2 H, 20-CH$_2$), 3.85 (d, J=7.0 Hz, 1 H, 3-H), 2.56–2.48 (m, 1 H, 6-H), 2.52 (s, 3 H, Me), 2.40 (dd, J=15.0 Hz, 9.5 Hz, 1 H, 14-H), 2.20–2.12 (m, 2 H, 14-H, OH), 2.18 (s, 3 H, Me), 2.04 (s, 3 H, Me), 1.92 (ddd, J=14.5, 10.5, 2.0 Hz, 1 H, 6-H), 1.72 (s, 3 H, Me), 1.22 (s, 3 H, Me), 1.19 (s, 3 H, Me), 0.93 (t, J=8.0 Hz, 9 H, OSi(CH$_2$CH$_3$)$_3$), 0.81 (t, J=8.0 Hz, 9 H, OSi(CH$_2$CH$_3$)$_3$), 0.64–0.34 (band, 12 H, OSi(CH$_2$CH$_3$)$_3$); FAB HRMS (NBA/CsI) m/e 1215.4065, M+Cs$^+$ calcd for C$_{58}$H$_{78}$O$_{14}$N$_2$Si$_2$ 1215.4046.

Taxoid 40. A solution of silyl ether 39 (2.7 mg, 0.00249 mmol) in THF (0.4 mL) at 25° C. was treated with HF•pyridine (0.170 mL) and stirred for 3 h. The reaction mixture was poured into a mixture of ethylacetate (10 mL) and aqueous NaHCO$_3$ (5 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by preparative TLC (silica, ethylacetate) to give 40 (0.8 mg, 38%) as a colorless film.

Physical Data for Taxoid 40. $R_f$=0.54 (silica, ethylacetate); $^1$H NMR (500 MHz, CDCl$_3$) δ8.80 (br d, J=4.5 Hz, 1 H, pyridine), 8.22 (d, J=7.5 Hz, 1 H, pyridine), 7.93 (ddd, J=7.5, 7.5, 1.5 Hz, 1 H, pyridine), 7.75–7.71 (m, 2 H), 7.54–7.30 (band, 9 H), 6.98 (d, J=9.0 Hz, 1 H, NH), 6.30–6.24 (m, 2 H, 10-H, 13-H), 5.82 (dd, J=9.0, 2.5 Hz, 1 H, 3'-H), 5.67 (d, J=7.0 Hz, 1 H, 2-H), 4.95 (dd, J=10.0, 2.0 Hz, 1 H, 5-H), 4.81 (dd, J=4.5, 2.5 Hz, 1 H, 2'-H), 4.41 (ddd, J=11.0, 7.0, 4.5 Hz, 1 H, 7-H), 4.31 (s, 2 H, 20-CH$_2$), 3.81 (d, J=7.0 Hz, 1 H, 3-H), 3.52 (br s, 1 H, OH), 3.50 (d, J=4.5 Hz, 1 H, 2'-OH), 2.56 (ddd, J=14.5, 9.5, 7.0 Hz, 1 H, 6-H), 2.46 (d, J=4.0 Hz, 1 H, 7-OH), 2.43–2.30 (m, 2 H, 14-CH$_2$), 2.38 (s, 3 H, OAc), 2.25 (s, 3 H, OAc), 1.90 (ddd, J=14.5, 11.0, 2.0 Hz, 1 H, 6-H), 1.81 (s, 3 H, Me), 1.71 (s, 3 H, Me), 1.26 (s, 3 H, Me), 1.15 (s, 3 H, Me).

Prepartion of 3-pyridinyl-C-2-taxol (44)

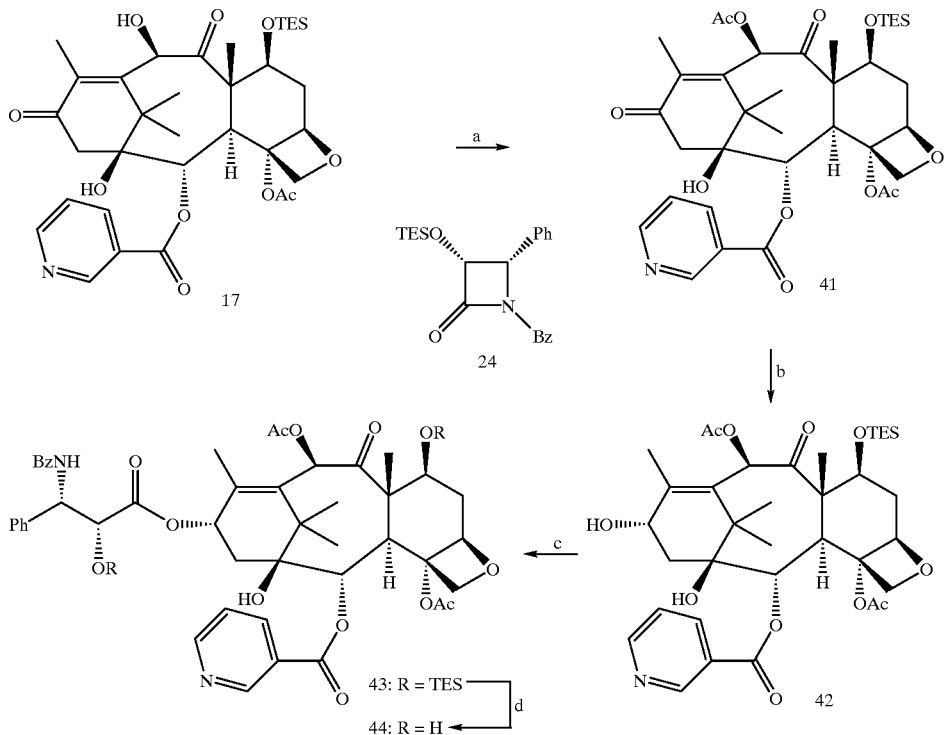

Acetate 41. A solution of alcohol 17 (42.9 mg, 0.0652 mmol) and 4-dimethylaminopyridine (DMAP, 23.9 mg, 0.196 nmmol) in CH$_2$Cl$_2$ (2.8 mL) at 25° C. was treated with acetic anhydride (0.235 mL, 2.49 mmol) and stirred for 2 h. The reaction mixture was diluted with ethylacetate (5 mL), treated with aqueous NaHCO$_3$ (7 mL), and stirred vigorously for 25 min. The organic layer was separated and the aqueous layer was extracted with ethylacetate (2×10 mL). The combined organic layer was washed with brine (5 mL), dried (MgSO$_4$), concentrated, and purified by flash chromatography (silica, ethylacetate) to give 41 (43.5 mg, 95%) as a white solid.

Physical Data for Acetate 41. R$_f$=0.61 (silica, ethylacetate); IR (film) v$_{max}$ 3470, 3327, 2955, 2881, 1731, 1675, 1592, 1370, 1279, 1229, 1108, 822, 738 cm$^{-1}$; $^1$H NMR (500 MHz, CDCl$_3$) δ9.23 (br s, 1 H, pyridine), 8.79 (br s, 1 H, pyridine), 8.30 (ddd, J=8.0, 2.0, 2.0 Hz, 1 H, pyridine), 7.43 (dd, J=8.0, 5.0 Hz, 1 H, pyridine), 6.58 (s, 1 H, 10-H), 5.70 (dd, J=6.5, 1.0 Hz, 1 H, 2-H), 4.91 (dd, J=9.5, 2.0 Hz, 1 H, 5-H), 4.47 (dd, J=10.5, 7.0 Hz, 1 H, 7-H), 4.28 (d, J=8.0 Hz, 1 H, 20-H), 4.11 (d, J=8.0 Hz, 1 H, 20-H), 3.91 (d, J=6.5 Hz, 1 H, 3-H), 2.93 (d, J=20.0 Hz, 1 H, 14-H), 2.68 (dd, J=20.0, 1.0 Hz, 1 H, 14-H), 2.53 (ddd, J=14.5, 9.5, 7.0 Hz, 1 H, 6-H), 2.24 (br s, 1 H, OH), 2.22 (s, 3 H, De), 2.18 (s, 3 H, Me), 2.17 (s, 3 H, Me), 1.85 (ddd, J=14.5, 10.5, 2.0 Hz, 1 H, 6-H), 1.66 (s, 3 H, Me), 1.26 (s, 3 H, Me), 1.18 (s, 3 H, Me), 0.90 (t, J=8.0 Hz, 9 H, OSi(CH$_2$CH$_3$)$_3$), 0.63–0.51 (band, 6 H, OSi(CH$_2$CH$_3$)$_3$); FAB HRMS (NBA/CsI) m/e 832.2145, M+Cs$^+$ calcd for C$_{36}$H$_{49}$O$_{11}$NSi 832.2129.

Alcohol 42. A solution of enone 41 (39.8 mg, 0.0569 mmol) in MeOH-THF (5:1, 3.1 mL) at 0° C. was treated with NaBH$_4$ (65.0 mg, 1.72 mmol, added by portions) and stirred for 1.5 h. The reaction mixture was diluted with ethylacetate (10 mL), treated with aqueous NH$_4$Cl (5 mL), and stirred for 10 min. The organic layer was separated and the aqueous layer was extracted with ethylacetate (2×10 mL). The combined organic layer was washed with brine (5 mL), dried (MgSO$_4$), concentrated, and purified by flash chromatography (silica, ethylacetate) to give 41 (3.7 mg, 9%) and 42 (24.3 mg, 67% based on 91% conversion) as an amorphous solid.

Physical Data for Alcohol 42. R$_f$=0.42 (silica, ethylacetate); IR (film) v$_{max}$ 3490, 2953, 2881, 1727, 1592, 1369, 1235, 1110, 822, 740 cm$^{-1}$; $^1$H NMR (500 MHz, CDCl$_3$) δ9.30 (d, J=2.0 Hz, 1 H, pyridine), 8.81 (dd, J=5.0, 2.0 Hz, 1 H, pyridine), 8.35 (ddd, J=8.0, 2.0, 2.0 Hz, 1 H, pyridine), 7.44 (dd, J=8.0, 5.0 Hz, 1 H, pyridine), 6.46 (s, 1 H, 10-H), 5.64 (d, J=7.0 Hz, 1 H, 2-H), 4.96 (dd, J=9.5, 1.5 Hz, 1 H, 5-H), 4.83 (br dd, J=12.5, 7.5 Hz, 1 H, 13-H), 4.49 (dd, J=10.5, 6.5 Hz, 1 H, 7-H), 4.28 (d, J=8.0 Hz, 1 H, 20-H), 4.15 (d, J=8.0 Hz, 1 H, 20-H), 3.89 (d, J=7.0 Hz, 1 H, 3-H), 2.53 (ddd, J=14.5, 9.5, 6.5 Hz, 1 H, 6-H), 2.30–2.20 (m, 2 H, 14-CH$_2$), 2.28 (s, 3 H, Me), 2.19 (d, J=1.0 Hz, 3 H, 18-Me), 2.18 (s, 3 H, Me), 1.87 (ddd, J=14.5, 10.5, 2.0 Hz, 1 H, 6-H), 1.68 (s, 3 H, Me), 1.63 (br s, 2 H, OH, OH), 1.19 (s, 3 H, Me), 1.04 (s, 3 H, Me), 0.92 (t, J=8.0 Hz, 9 H, OSi(CH$_2$CH$_2$)$_3$), 0.64–0.51 (band, 6 H, OSi(CH$_2$CH$_3$)$_3$); FAB HRMS (NBA/CsI) m/e 834.2270, M+Cs$^+$ calcd for C$_{36}$H$_{51}$O$_{11}$NSi 834.2286.

DiTES taxoid 43. To a solution of alcohol 42 (12.6 mg, 0.018 mmol, previously azeotroped twice with benzene) and β-lactam 24 (17.0 mg, 0.0446 mmol, previously azeotroped twice with benzene) in THF (0.97 mL) at 0° C., prepared from the Ojima-Holton protocol (Holton, R. A. Chem Abstr. 1990, 114, 164568q; Ojima, I.; Habus, I.; Zhao, M.; Georg, G. I.; Jayasinghe, L. R. J. Org. Chem. 1991, 56, 1681–1683; Ojima, I.; Habus, I.; Zhao, M.; Zucco, M.; Park, Y. H.; Sun, C. M.; Brigaud, T. Tetrahedron 1992, 48, 6985–7012), was added NaN(SiMe$_3$)$_2$ (0.054 mL of a 1.0 M solution in THF, 0.054 mmol) dropwise. The resulting solution was stirred for 0.5 h and poured into a mixture of ethylacetate (10 mL) and aqueous NH$_4$Cl (5 mL). The organic layer was separated and the aqueous layer was extracted with ethylacetate (2×5 mL). The combined organic layer was washed with brine (5 mL), dried (MgSO$_4$), concentrated, and purified by flash chromatography (silica, 50→95% ethylacetate in hexanes) to give 42 (1.0 mg, 8%) and 43 (8.6. mg, 48% based on 92% conversion) as a white solid.

Physical Data for DiTES taxoid 43. $R_f$=0.40 (silica, 50% ethylacetate in hexanes); IR (film) $v_{max}$ 3433, 2955, 2880, 1730, 1662, 1370, 1238, 1112, 1018, 985, 824, 740 cm$^{-1}$; $^1$H NMR (500 MHz, CDCl$_3$) δ9.34 (d, J=2.0 Hz, 1 H, pyridine), 8.82 (dd, J=5.0, 2.0 Hz, 1 H, pyridine), 8.42 (ddd, J=8.0, 2.0, 2.0 Hz, 1 H, pyridine), 7.74–7.69 (m, 2 H), 7.51–7.20 (band, 9 H), 7.08 (d, J=9.0 Hz, 1 H, NH), 6.46 (s, 1 H, 10-H), 6.22 (br t, J=9.0 Hz, 1 H, 13-H), 5.74–5.66 (m, 2 H, 2-H, 3'-H), 4.95 (dd, J=9.5, 2.0 Hz, 1 H, 5-H), 4.70 (d, J=2.0 Hz, 1 H, 2'-H), 4.48 (dd, J=10.5,6.5 Hz, 1 H, 7-H), 4.30 (d, J=8.0 Hz, 1 H, 20-H), 4.21 (d, J=8.0 Hz, 1 H, 20-H), 3.86 (d, J=7.0 Hz, 1 H, 3-H), 2.58–2.48 (m, 1 H, 6-H), 2.54 (s, 3 H, Me), 2.40 (dd, J=15.5, 9.0 Hz, 1 H, 14-H), 2.17 (s, 3 H, Me), 2.14 (dd, J=15.5, 9.0 Hz, 1 H, 14-H), 2.03 (br s, 3 H, Me), 1.95–1.86 (m, 1 H, 6-H), 1.73 (s, 4 H, Me, OH), 1.22 (s, 3 H, Me), 1.18 (s, 3 H, Me), 0.93 (t, J=8.0 Hz, 9 H, OSi(CH$_2$Cl$_3$)$_3$), 0.82 (t, J=8.0 Hz, 9 H, OSi(CH$_2$CH$_3$)$_3$), 0.65–0.37 (band, 12 H, OSi(CH$_2$CH$_3$)$_3$, OSi(CH$_2$CH$_3$)$_3$); FAB HRMS (NBA/CsI) m/e 1215.4066, M+Cs$^+$ calcd for C$_{58}$H$_{78}$O$_{14}$N$_2$Si$_2$ 1215.4046.

Taxoid 44. A solution of silyl ether 43 (6.4 mg, 0.0059 mmol) in THF (0.4 mL) at 25° C. was treated with HF-pyridine (0.160 mL) and stirred for 1.25 h. The reaction mixture was poured into a mixture of ethylacetate (10 mL) and aqueous NaHCO$_3$ (5 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by preparative TLC (silica, ethylacetate) to give 44 (3.8 mg, 75%) as a colorless film.

Physical Data for Taxoid 44. $R_f$=0.59 (silica, ethylacetate); IR (film) $v_{max}$ 3396, 2928, 1728, 1644, 1371, 1273, 1241, 1111, 1071 cm$^{-1}$; $^1$H NMR (500 MHz, CDCl$_3$) δ9.34 (br s, 1 H, pyridine), 8.83 (br d, J=3.5 Hz, 1 H, pyridine), 8.41 (br d, J=8.0 Hz, 1 H, pyridine), 7.75–7.68 (m, 2 H), 7.53–7.34 (band, 9 H), 6.91 (d, J=9.0 Hz, 1 H, NH), 6.27 (s, 1 H, 10-H), 6.23 (br t, J=9.0 Hz, 1 H, 13-H), 5.78 (dd, J=9.0, 2.5 Hz, 1 H, 3'-H), 5.69 (d, J=7.0 Hz, 1 H, 2-H), 4.95 (dd, J=9.5, 2.0 Hz, 1 H, 5-H), 4.79 (dd, J=5.5, 2.5 Hz, 1 H, 2'-H), 4.41 (ddd, J=11.0, 6.5, 4.0 Hz, 1 H, 7-H), 4.29 (d, J=8.5 Hz, 1 H, 20-H), 4.20 (d, J=8.5 Hz, 1 H, 20-H), 3.82 (d, J=7.0 Hz, 1 H, 3-H), 3.54 (d, J=5.5 Hz, 1 H, 2'-OH), 2.56 (ddd, J=14.5, 9.5, 6.5 Hz, 1 H, 6-H), 2.49 (d, J=4.0 Hz, 1 H, 7-OH), 2.43–2.26 (m, 2 H, 14-CH$_2$), 2.38 (s, 3 H, Me), 2.24 (s, 3 H, Me), 1.89 (ddd, J=14.5, 11.0, 2.0 Hz, 1 H, 6-H), 1.83 (s, 1 H, OH), 1.82 (s, 3 H, Me), 1.69 (s, 3 H, Me), 1.25 (s, 3 H, Me), 1.14 (s, 3 H, Me); FAB HRMS (NBA/CsI) m/e 987.2325, M+Cs$^+$ calcd for C$_{46}$H$_{50}$O$_{14}$N$_2$ 987.2316.

Preparation of 4-N, N-dimethylaniline-C-2 taxol (48)

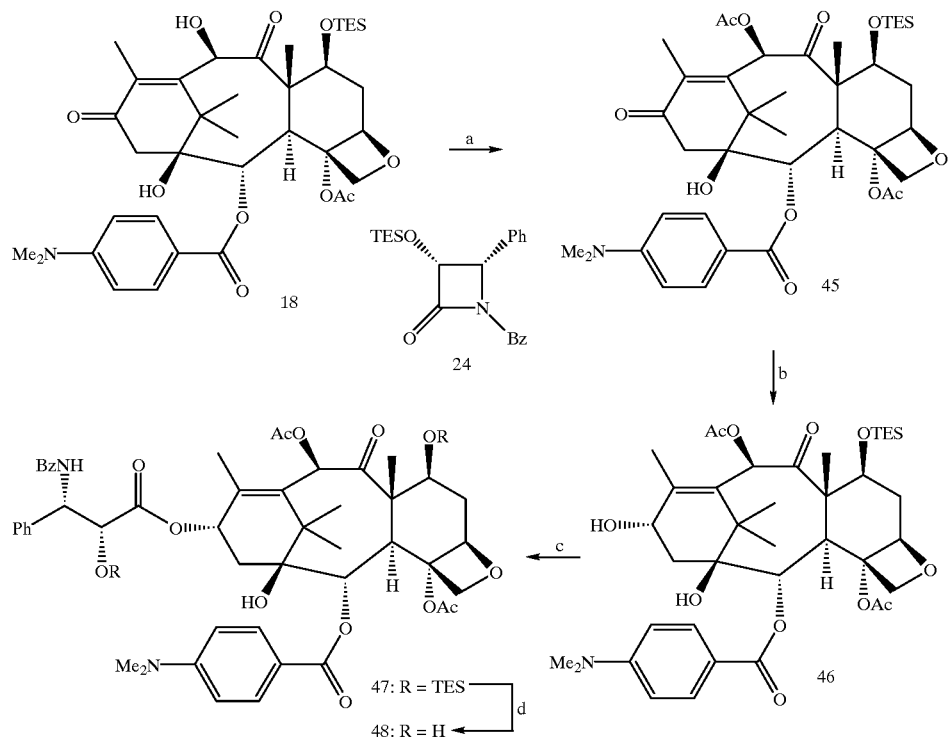

Acetate 45. A solution of alcohol 18 (50.0 mg, 0.0714 mmol) and 4-dimethylaminopyridine (DMAP, 26.0 mg, 0.213 mmol) in CH$_2$Cl$_2$ (3.0 mL) at 25° C. was treated with acetic anhydride (0.250 mL, 2.65 mmol) and stirred for 2.5 h. The reaction mixture was diluted with CH$_2$Cl$_2$ (10 mL), treated with aqueous NaHCO$_3$ (7 mL), and stirred vigorously for 25 min. The organic layer was separated and the aqueous layer was extracted with CH$_2$Cl$_2$ (2×10 mL). The combined organic layer was washed with brine (5 mL), dried (MgSO$_4$), concentrated, and purified by flash chromatography (silica, 10% ethylacetate in benzene) to give 45 (41.0 mg, 77%) as an amorphous solid.

Physical Data for Acetate 45. $R_f$=0.27 (silica, 35% ethylacetate in hexanes); IR (film) $v_{max}$ 3425, 2945, 1722, 1674, 1605, 1365, 1275, 1232, 1179, 1094; $^1$H NMR (500 MHz, CDCl$_3$) δ7.89 (d, J=9.0 Hz, 2 H, Ar), 6.64 (d, J=9.0 Hz, 2 H, Ar), 6.56 (s, 1 H, 10-H), 5.64 (d, J=6.5 Hz, 1 H, 2-H), 4.90 (br d, J=8.0 Hz, 1 H, 5-H), 4.45 (dd, J=10.5, 7.0 Hz, 1 H, 7-H), 4.36 (d, J=9.0 Hz, 1 H, 20-H), 4.11 (d, J=9.0 Hz, 1 H, 20-H), 3.85 (d, J=6.5 Hz, 1 H, 3-H), 3.05 (s, 6 H, NMe$_2$), 2.90 (d, J=20.0 Hz, 1 H, 14-H), 2.62 (d, J=20.0 Hz, 1 H, 14-H), 2.51 (ddd, J=14.0, 8.0, 7.0, 1 H, 6-H), 2.20 (s, 3 H, Me), 2.16 (s, 3 H, Me), 2.15 (s, 3 H, Me), 2.04 (s, 1 H, OH), 1.84 (ddd, J=14.0, 10.5, 2.0 Hz, 1 H, 6-H), 1.63 (s, 3 H, Me), 1.23 (s, 3 H, Me), 1.16 (s, 3 H, Me), 0.89 (t, J=8.0 Hz, 9 H, OSi(CH$_2$CH$_3$)$_3$), 0.58–0.53 (band, 6 H, OSi(CH$_2$CH$_3$)$_3$); FAB HRMS (NBA/CsI) m/e 874.8589, M+Cs$^+$ calcd for C$_{39}$H$_{55}$O$_{11}$NSi 874.8594.

Alcohol 46. A solution of enone 45 (40.0 mg, 0.0539 mmol) in MeOH-THF (5.8:1, 4.1 mL) at 0° C. was treated with NaBH$_4$ (30.2 mg, 0.80 mmol, added by portions), stirred for 1 h, allowed to warm to 25° C. and stirred for 1.5 h. The reaction mixture was diluted with CH$_2$Cl$_2$ (15 mL), treated with aqueous NH$_4$Cl (5 mL), and stirred for 10 min. The organic layer was separated and the aqueous layer was extracted with CH$_2$Cl$_2$ (2×10 mL). The combined organic layer was washed with brine (5 mL), dried (MgSO$_4$), concentrated, and purified by flash chromatography (silica, 25→50% ethylacetate in petroleum ether) to give 45 (6.0 mg, 15%) and 46 (30.0 mg, 88% based on 85% conversion) as an amorphous solid.

Physical Data for Alcohol 46. R$_f$=0.30 (silica, 50% ethylacetate in petroleum ether); $^1$H NMR (500 MHz, CDCl$_3$) δ7.93 (d, J=9.0 Hz, 2 H, Ar), 6.64 (d, J=9.0 Hz, 2 H, Ar), 6.42 (s, 1 H, 10-H), 5.57 (d, J=7.0 Hz, 1 H, 2-H), 4.94 (br d, J=8.0 Hz, 1 H, 5-H), 4.83–4.75 (m, 1 H, 13-H), 4.46 (dd, J=10.5, 6.5 Hz, 1 H, 7-H), 4.34 (d, J=8.5 Hz, 1 H, 20-H), 4.13 (d, J=8.5 Hz, 1 H, 20-H), 3.82 (d, J=7.0 Hz, 1 H, 3-H), 3.04 (s, 6 H, Me$_2$N), 2.54–2.44 (m, 1 H, 6-H), 2.26 (s, 3 H, Me), 2.23 (d, J=7.5 Hz, 2 H, 14-CH$_2$), 2.16 (s, 6 H, Me, Me), 2.08 (d, J=4.5 Hz, 1 H, OH), 1.89–1.80 (m, 2 H, 6-H, OH), 1.64 (s, 3 H, Me), 1.16 (s, 3 H, Me), 1.01 (s, 3 H, Me), 0.89 (t, J=8.5 Hz, 9 H, OSi(CH$_2$Cl$_3$)$_3$), 0.62–0.48 (band, 6 H, OSi(CH$_2$CH$_3$)$_3$).

DiTES taxoid 47. To a solution of alcohol 46 (14.0 mg, 0.0188 mmol, previously azeotroped twice with benzene) and β-lactam 24 (25.0 mg, 0.0656 mmol, previously azeotroped twice with benzene) in THF (0.75 mL) at 0° C., prepared from the Ojima-Holton protocol (Holton, R. A. Chem Abstr. 1990, 114, 164568q; Ojima, I.; Habus, I.; Zhao, M.; Georg, G. .; Jayasinghe, L. R. J. Org. Chem. 1991, 56, 1681–1683; Ojima, I.; Habus, I.; Zhao, M.; Zucco, M.; Park, Y. H.; Sun, C. M.; Brigaud, T. Tetrahedron 1992, 48, 6985–7012), was added NaN(SiMe$_3$)$_2$ (0.056 mL of a 1.0 M solution in THF, 0.056 mmol) dropwise. The resulting solution was stirred for 20 min and poured into a mixture of CH$_2$Cl$_2$ (10 mL) and aqueous NH$_4$Cl (5 mL). The organic layer was separated and the aqueous layer was extracted with CH$_2$Cl$_2$ (2×5 mL). The combined organic layer was washed with brine (5 mL), dried (MgSO$_4$), concentrated, and purified by flash chromatography (silica, 10→15% ethylacetate in benzene, then 50% ethylacetate in petroleum ether) to give 47 (12.0 mg, 57%) as a white solid.

Physical Data for DiTES taxoid 47. R$_f$=0.26 (silica, 15% ethylacetate in PhH); IR (film) V$_{max}$ 3425, 2946, 2882, 1722, 1669, 1600, 1365, 1275, 1238, 1179, 1094 cm$^{-1}$; $^1$H NMR (500 MHz, CDCl$_3$) δ7.96 (d, J=9.0 Hz, 2 H, Ar), 7.77–7.72 (m, 2 H), 7.54–7.26 (band, 8 H), 7.12 (d, J=8.5 Hz, 1 H, NH), 6.69 (d, J=9.0 Hz, 2 H), 6.43 (s, 1 H, 10-H), 6.23 (br t, J=9.0 Hz, 1 H, 13-H), 5.68–5.63 (m, 2 H, 2-H, 3'-H), 4.93 (br d, J=8.0 Hz, 1 H, 5-H), 4.67 (d, J=2.0 Hz, 1 H, 2'-H), 4.45 (dd, J=10.5 Hz, 6.5 Hz, 1 H, 7-H), 4.36 (d, J=8.5 Hz, 1 H, 20-H), 4.20 (d, J=8.5 Hz, 1 H, 20-H), 3.78 (d, J=7.0 Hz, 1 H, 3-H), 3.04 (s, 6 H, Me$_2$N), 2.55–2.46 (m, 1 H, 6-H), 2.53 (s, 3 H, OAc), 2.36 (dd, J=15.5, 9.0 Hz, 1 H, 14-H), 2.15 (s, 3 H, Me), 2.09 (dd, J=15.5, 9.0 Hz, 1 H, 14-H), 2.00 (d, J=1.0 Hz, 3 H, Me), 1.92–1.84 (m, 2 H, 6-H, OH), 1.67 (s, 3 H, Me), 1.20 (s, 3 H, 5 Me), 1.16 (s, 3 H, Me), 0.90 (t, J=8.0 Hz, 9 H, OSi(CH$_2$CH$_3$)$_3$), 0.79 (t, J=8.0 Hz, 9 H, OSi(CH$_2$CH$_3$)$_3$), 0.63–0.35 (band, 12 H, OSi(CH$_2$CH$_3$)$_3$); FAB HRMS (NBA/CsI) m/e 1257.4503, M+Cs$^+$ calcd for C$_{61}$H$_{84}$O$_{14}$N$_2$Si$_2$ 1257.4515.

Taxoid 48. A solution of silyl ether 47 (12.0 mg, 0.0107 mmol) in THF (1.0 mL) at 25° C. was treated with HF·pyridine (0.05 mL) and stirred for 1.5 h. The reaction mixture was poured into a mixture of ethylacetate (10 mL) and aqueous NaHCO$_3$ (5 mL) and the resulting mixture was stirred for 10 min. The organic layer was separated and the aqueous layer was extracted with ethylacetate (2×10 mL). The combined organic layer was washed with brine (5 mL), dried (MgSO$_4$), concentrated, and purified by flash chromatography (silica, 50→75% ethylacetate in petroleum ether) to give 48 (8.0 mg, 84%) as a colorless film.

Physical Data for Taxoid 48. R$_f$=0.44 (silica, 75% ethylacetate in petroleum ether); IR (film) V$_{max}$ 3414, 2914, 2850, 1722, 1664, 1660, 1371, 1275, 1243, 1179 cm$^{-1}$; $^1$H NMR (500 MHz, CDCl$_3$) δ7.95 (d, J=9.0 Hz, 2 H), 7.77–7.72 (m, 2 H), 7.55–7.30 (band, 8 H), 7.03 (d, J=9.0 Hz, 1 H, NH), 6.67 (d, J=9.0 Hz, 2 H), 6.24 (s, 1 H, 10-H), 6.20 (br t, J=9.0 Hz, 1 H, 13-H), 5.76 (dd, J=9.0, 2.5 Hz, 1 H, 3'-H), 5.62 (d, J=7.0 Hz, 1 H, 2-H), 4.93 (br d, J=7.5 Hz, 1 H, 5-H), 4.76 (dd, J=5.0, 2.5 Hz, 1 H, 2'-H), 4.37 (ddd, J=11.5, 6.5, 4.0 Hz, 1 H, 7-H), 4.34 (d, J=8.5 Hz, 1 H, 20-H), 4.18 (d, J=8.5 Hz, 1 H, 20-H), 3.73 (d, J=7.0 Hz, 1 H, 3-H), 3.57 (d, J=5.0 Hz, 1 H, 2'-OH), 3.04 (s, 6 H, Me$_2$N), 2.58–2.48 (m, 1 H, 6-H), 2.44 (d, J=4.0 Hz, 1 H, 7-OH), 2.37 (s, 3 H, Me), 2.30–2.25 (m, 2 H, 14-CH$_2$), 2.22 (s, 3 H, Me), 1.95 (s, 1 H, OH), 1.88–1.81 (m, 1 H, 6-H), 1.74 (d, J=1.0 Hz, 3 H, Me), 1.65 (s, 3 H, Me), 1.21 (s, 3 H, Me), 1.11 (s, 3 H, Me); FAB HRMS (NBA/CsI) m/e 1029.2760, M+Cs$^+$ calcd for C$_{49}$H$_{56}$N$_2$O$_{14}$ 1029.2786.

Preparation of 1-naphthalene-C-2-taxol (52)

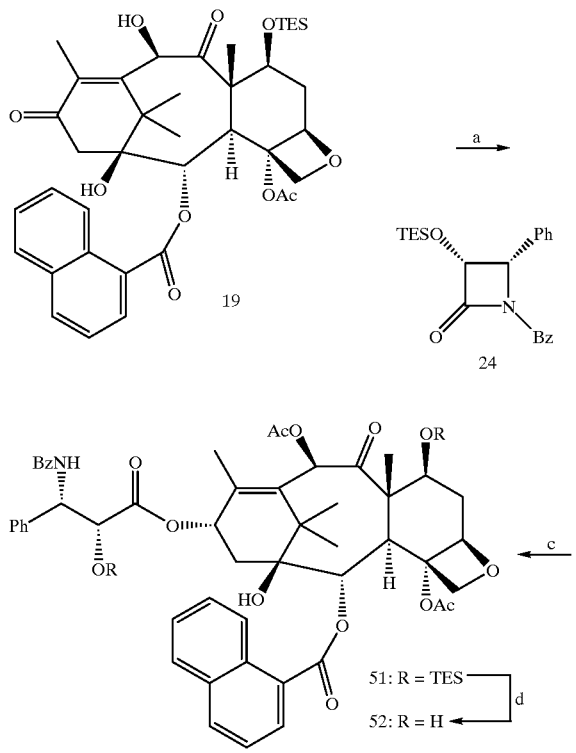

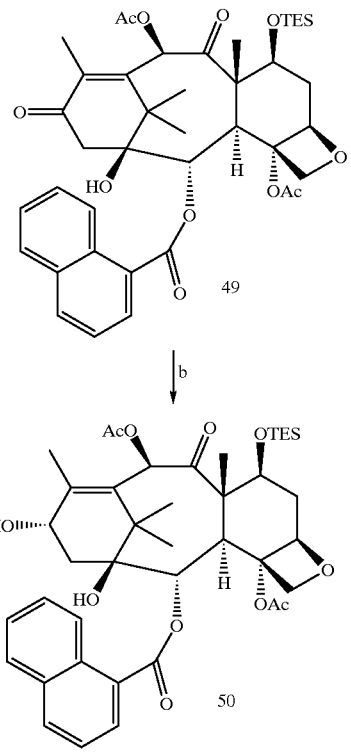

Acetate 49. A solution of previous alcohol 19 and 4-dimethylaminopyridine (DMAP, 100 mg, 0.819 mmol) in $CH_2Cl_2$ (3 mL) at 25° C. was treated with acetic anhydride (0.50 mL, 5.30 mmol) and stirred for 3 h. The reaction mixture was diluted with $CH_2Cl_2$ (5 mL), treated with aqueous $NaHCO_3$ (7 mL), and stirred vigorously for 25 min. The organic layer was separated and the aqueous layer was extracted with $CH_2Cl_2$ (2×10 mL). The combined organic layer was washed with brine (5 mL), dried ($MgSO_4$), concentrated, and purified by preparative TLC (silica, 10% ethylacetate in benzene) to give 49 (54.1 mg, 89% from carbonate 7) as an amorphous solid.

Physical Data for Acetate 49. $R_f$=0.27 (20% ethylacetate in petroleum ether); IR (film) $v_{max}$ 3416, 2953, 2879, 1726, 1676, 1370, 1224, 1089 cm$^{-1}$; $^1$H NMR (500 MHz, CDCl$_3$) δ8.66 (s, 1 H, naphthalene), 8.06 (dd, 1 H, J=9.0, 2.0 Hz, naphthalene), 7.98–7.89 (m, 3 H, naphthalene), 7.68–7.55 (m, 2 H, naphthalene), 6.61 (s, 1 H, 10-H), 5.75 (d, J=7.0 Hz, 1 H, 2-H), 4.95 (br d, J=8.0 Hz, 1 H, 5-H), 4.50 (dd, J=10.5, 7.0 Hz, 1 H, 7-H), 4.35 (d, J=8.5 Hz, 1 H, 20-H), 4.16 (d, J=8.5 Hz, 1H, 20-H), 3.96 (d, J=8.5 Hz, 1 H, 20-H), 3.96 (d, J=7.0 Hz, 1 H, 3-H), 3.03 (d, J=20.0 Hz, 1 H, 14-H), 2.70 (d, J=20.0 Hz, 1 H, 14-H), 2.61–2.50 (m, 2 H, 6-H, OH), 2.27 (s, 3 H, Me), 2.24 (s, 3 H, Me), 2.21 (s, 3 H, Me), 1.91–1.83 (m, 1 H, 6-H), 1.70 (s, 3 H, Me), 1.30 (s, 3 H, Me), 1.20 (s, 3 H, Me), 0.93 (t, J=8.0 Hz, 9 H, OSi(CH$_2$CH$_3$)$_3$), 0.66–0.57 (band, 6 H, OSi(CH$_2$CH$_3$)$_3$); FAB HRMS (NBA/CsI) m/e 881.2326, M+Cs$^+$ calcd for $C_{41}H_{52}O_{11}Si$ 881.2333.

Alcohol 50. A solution of enone 49 (54.1 mg, 0.0722 mmol) in MeOH (10 mL) at 25° C. was treated with NaBH$_4$ (54.5 mg, 1.44 mmol, added by portions) and stirred for 2.0 h. The reaction mixture was diluted with $CH_2Cl_2$ (10 mL), treated with aqueous NH$_4$Cl (5 mL), and stirred for 10 min. The organic layer was separated and the aqueous layer was extracted with $CH_2Cl_2$ (2×10 mL). The combined organic layer was washed with brine (5 mL), dried (MgSO$_4$), concentrated, and purified by preparative TLC (silica, 20% ethylacetate in petroleum ether) to give 50 (26 mg, 48%) as an amorphous solid.

Physical Data for Alcohol 50. $R_f$=0.12 (20% ethylacetate in petroleum ether); IR (film) $v_{max}$ 3524, 2953, 1719, 1369, 1231, 1093, 829 cm$^{-1}$; $^1$H NMR (500 MHz, CDCl$_3$) δ8.70 (s, 1 H, naphthalene), 8.11 (dd, J=8.5, 1.5 Hz, 1 H, naphthalene), 7.96–7.86 (m, 3 H, naphthalene), 7.65–7.54 (m, 2 H, naphthalene), 6.45 (s, 1 H, 10-H), 5.68 (d, J=7.0 Hz, 1 H, 2-H), 4.98 (br d, J=8.0 Hz, 1 H, 5-H), 4.884.81 (m, 1 H, 13-H), 4.51 (dd, J=10.5, 7.0 Hz, 1 H, 7-H), 4.34 (d, J=8.5 Hz, 1 H, 20-H), 4.19 (d, J=8.5 Hz, 1 H, 20-H), 3.93 (d, J=7.0 Hz, 1 H, 3-H), 2.58–2.50 (m, 1, 6-H), 2.41–2.14 (m, 3 H, 14-CH$_2$, 13-OH), 2.37 (s, 3 H, Me), 2.21 (br s, 3 H, Me), 2.19 (s, 3 H, Me), 1.92–1.84 (m, 1 H, 6-H), 1.72 (s, 1 H, OH) 1.71 (s, 3 H, Me), 1.22 (s, 3 H, Me), 1.05 (s, 3 H, Me), 0.93 (t, J=8.0 Hz, 9 H, OSi(CH$_2$Cl$_3$)$_3$), 0.65–0.51 (band, 6 H, OSi(CH$_2$CH$_3$)$_3$); FAB HRMS (NBA/CsI) m/e 883.2484, M+Cs$^+$ calcd for $C_{41}H_{54}O_{11}Si$ 883.2490.

DiTES taxoid 51. To a solution of alcohol 50 (20.0 mg, 0.0266 mmol, previously azeotroped twice with benzene) and β-lactam 24 (20.0 mg, 0.0525 mmol, previously azeotroped twice with benzene) in THF (1.1 mL) at −78° C., prepared from the Ojima-Holton protocol (Holton, R. A. *Chem Abstr.* 1990, 114, 164568q; Ojima, I.; Habus, I.; Zhao, M.; Georg, G. I.; Jayasinghe, L. R. *J. Org. Chem.* 1991, 56, 1681–1683; Ojima, I.; Habus, I.; Zhao, M.; Zucco, M.; Park, Y. H.; Sun, C. M.; Brigaud, T. *Tetrahedron* 1992, 48, 6985–7012), was added NaN(SiMe$_3$)$_2$ (0.065 mL of a 1.0 M solution in THF, 0.065 mmol) dropwise. The resulting solution was stirred for 10 min and poured into a mixture of $CH_2Cl_2$ (10 mL) and aqueous NH$_4$Cl (5 mL). The organic layer was separated and the aqueous layer was extracted with $CH_2Cl_2$ (2×5 mL). The combined organic layer was washed with brine (5 mL), dried ($MgSO_4$), concentrated, and purified by preparative TLC (silica, 20% ethylacetate in petroleum ether) to give 51 (18.7 mg, 62%) as a white solid.

Taxoid 52. A solution of silyl ether 51 (18.7 mg, 0.0165 mmol) in THF (2 mL) at 25° C. was treated with 20-H), 3.76 (d, J=7.0 Hz, 1 H, 3-H), 3.53 (br s, 1 H, OH), 2.52–2.43 (m, 1 H, 6-H), 2.42 (d, J=4.0 Hz, 1 H, OH), 2.40 (s, 3 H, Me), 2.36 (dd, J=15.5, 9.0 Hz, IH, 14-H), 2.25 (dd, J=15.5, 9.0 Hz, 1 H, 14-H), 2.17 (s, 3 H, Me), 1.85–1.77 (m, 2 H, 6-H, OH), 1.74 (br s, 3 H, Me), 1.63 (s, 3 H, Me), 1.17 (s, 3 H, Me), 1.09 (s, 3 H, Me); FAB HRMS (NBA/CsI) m/e 1036.2505, M+Cs$^+$ calcd for $C_{51}H_{53}NO_{14}$ 1036.2520

Preparation of thioether-C-2 taxol (56)

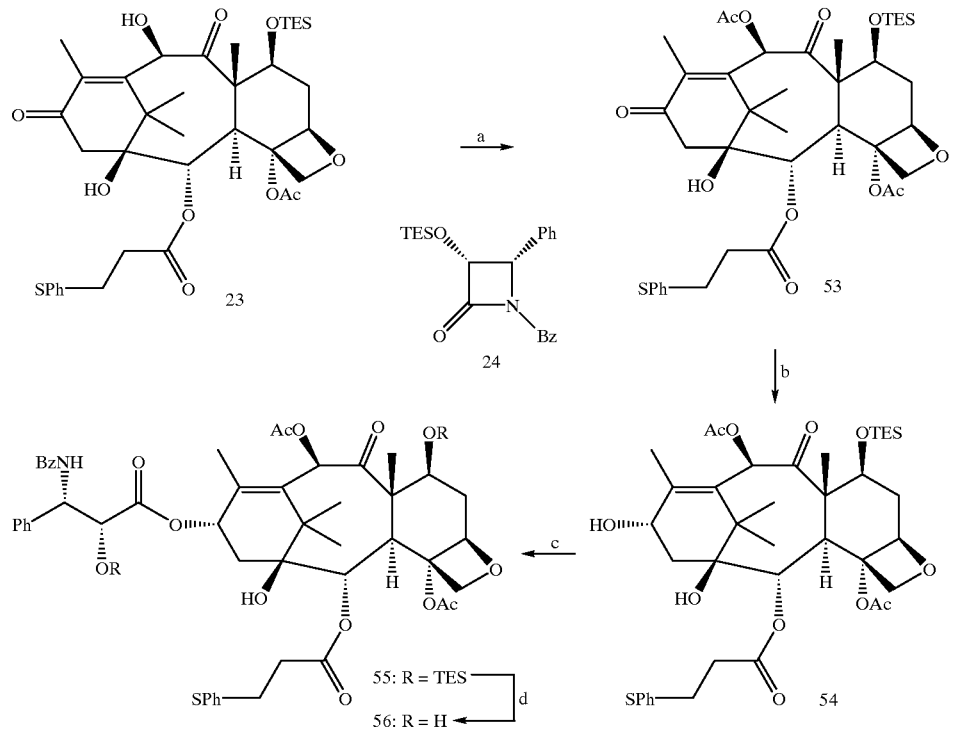

HF•pyridine (1 mL) and stirred for 1 h. The reaction mixture was poured into a mixture of ethylacetate (10 mL) and aqueous $NaHCO_3$ (5 mL) and the resulting mixture was stirred for 10 min. The organic layer was separated and the aqueous layer was extracted with ethylacetate (2×10 mL). The combined organic layer was washed with brine (5 mL), dried ($MgSO_4$), concentrated, and purified by preparative TLC (silica, 50% ethylacetate in petroleum ether) to give 52 (12.8 mg, 86%) as a colorless film.

Physical Data for Taxoid 52. $R_f$=0.16 (silica, 50% ethylacetate in petroleum ether); IR (film) $v_{max}$ 3420, 2967, 2896, 1721, 1652, 1519, 1370, 1233, 1073, 776 cm$^{-1}$; $^1$H NMR (500 MHz, CDCl$_3$) δ8.67 (s, 1 H, naphthalene), 8.04 (dd, J=8.5, 1.5 Hz, 1 H, naphthalene), 7.95 (br d, J=8.5 Hz, 1 H, naphthalene), 7.87 (br d, J=9.0 Hz, 1 H), 7.81 (br d, J=8.5 Hz, IH), 7.65–7.61 (m, 2 H), 7.56–7.51 (m, 1 H), 7.49–7.22 (band, 9 H), 6.94 (d, J=9.0 Hz, 1 H, NH), 6.23–6.16 (m, 2 H, 10-H, 13-H), 5.78 (dd, J=9.0, 2.0 Hz, 1 H, 3'-H), 5.64 (br d, J=7.0 Hz, 1 H, 2-H), 4.87 (br d, J=8.0 Hz, 1 H, 5-H), 4.78–4.72 (m, 1 H, 2'-H), 4.38–4.31 (m, 1 H, 7-H), 4.24 (d, J=8.5 Hz, 1 H, 20-H), 4.16 (d, J=8.5 Hz, 1 H, Acetate 53. A solution of alcohol 23 (25.2 mg, 0.0351 mmol) and 4-dimethylaminopyridine (DMAP, 12.2 mg, 0.0999 mmol) in $CH_2Cl_2$ (1.5 mL) at 25° C. was treated with acetic anhydride (0.120 mL, 1.27 mmol) and stirred for 1.5 h. The reaction mixture was diluted with $CH_2Cl_2$ (5 mL), treated with aqueous $NaHCO_3$ (7 mL), and stirred vigorously for 25 min. The organic layer was separated and the aqueous layer was extracted with $CH_2Cl_2$ (2×10 mL). The combined organic layer was washed with brine (5 mL), dried ($MgSO_4$), concentrated, and purified by flash chromatography (silica, 30% ethylacetate in petroleum ether) to give 53 (25.3 mg, 95%) as a colorless oil.

Physical Data for Acetate 53. $R_f$=0.41 (silica, 10% ethylacetate in benzene, 2 elutions); IR (film) $v_{max}$ 3471, 2954, 2881, 1729, 1675, 1370, 1226, 986, 824, 738 cm$^{-1}$; $^1$H NMR (500 MHz, CDCl$_3$) δ7.38–7.25 (band, 5 H, SPh), 6.54 (s, 1 H, 10-H), 5.49 (br d, J=6.5 Hz, 1 H, 2-H), 4.90 (dd, J=9.5, 2.0 Hz, 1 H, 5-H), 4.42 (dd, J=10.5, 6.5 Hz, IH, 7-H), 4.37 (d, J=8.0 Hz, 1 H, 20-H), 4.17 (d, J=8.0 Hz, 1 H, 20-H), 3.78 (d, J=6.5 Hz, 1 H, 3-H), 3.23–3.13 (m, 2 H, CH$_2$SPh), 2.78 (d, J=20.0 Hz, 1 H, 14-H), 2.72–2.58 (m, 3 H, CH$_2$CH$_2$SPh, 14-H), 2.52 (ddd, J=14.5, 9.5, 6.5, 1 H, 6-H), 2.45 (s, 1 H, OH), 2.21 (s, 3 H, Me), 2.15 (s, 3 H, Me), 2.04 (s, 3 H, Me), 1.86 (ddd, J=10.5, 2.0 Hz, 1 H, 6-H), 1.62 (s, 3 H, Me), 1.23 (s, 3 H, Me), 1.19 (s, 3 H, Me), 0.91 (t, J=8.0 Hz, 9 H, OSi(CH$_2$CH$_3$)$_3$), 0.64–0.52 (band, 6 H, OSi(CH$_2$CH$_3$)$_3$); FAB HRMS (NBA/CsI) m/e 891.2225, M+Cs$^{30}$ calcd for $C_{39}H_{54}O_{11}SSi$ 891.2210.

Alcohol 54. A solution of enone 53 (24.4 mg, 0.032 mmol) in MeOH-THF (5:1, 1.9 mL) at 0° C. was treated with $NaBH_4$ (18.1 mg, 0.48 mmol, added by portions) and stirred for 1.25 h. The reaction mixture was diluted with $CH_2Cl_2$ (5 mL), treated with aqueous $NH_4Cl$ (5 mL), and stirred for 10 min. The organic layer was separated and the aqueous layer was extracted with $CH_2Cl_2$ (2×5 mL). The combined organic layer was washed with brine (5 mL), dried ($MgSO_4$), concentrated, and purified by flash chromatography (silica, 30% ethylacetate in hexanes) to give 54 (14.6 mg, 60%) as an amorphous solid.

Physical Data for Alcohol 54. $R_f$=0.11 (silica, 30% ethylacetate in hexanes); IR (film) $v_{max}$ 3487, 2938, 2880, 1729, 1586, 1369, 1234, 977, 738 $cm^{-1}$; $^1H$ NMR (500 MHz, $CDCl_3$) δ7.40–7.23 (band, 5 H, SPh), 6.42 (s, 1 H, 10-H), 5.43 (d, J=7.0 Hz, 1 H, 2-H), 4.94 (dd, J=9.5, 2.0 Hz, 1 H, 5-H), 4.85–4.78 (m, 1 H, 13-H), 4.43 (dd, J=10.5, 6.5 Hz, 1 H, 7-H), 4.37 (d, J=8.0 Hz, 1H, 20-H), 4.18 (d, J=8.0 Hz, 1 H, 20-H), 3.74 (d, J=7.0 Hz, 1 H, 3-H), 3.25–3.15 (m, 2 H, $CH_2SPh$), 2.71–2.57 (m, 2 H, $CH_2CH_2SPh$), 2.51 (ddd, J=14.5, 9.5, 6.5 Hz, 1 H, 6-H), 2.25 (dd, J=15.5, 9.5 Hz, 1 H, 14-H), 2.16 (s, 3 H, Me), 2.15 (d, J=1.0 Hz, 3 H, 18-Me), 2.15 (s, 3 H, Me), 2.09 (dd, J=15.5, 7.0 Hz, 1 H, 14-H), 2.05 (br s, 1 H, OH), 1.99–1.96 (m, 1 H, OH), 1.86 (ddd, J=14.5, 10.5, 2.0 Hz, 1 H, 6-H), 1.63 (S, 3 H, Me), 1.15 (s, 3 H, Me), 1.04 (s, 3 H, Me), 0.91 (t, J=8.0 Hz, 9 H, $OSi(CH_2CH_3)_3$), 0.64–0.50 (band, 6 H $Si(CH_2CH_4H_3)_3$); FAB HRMS (NBA/CsI) m/e 893.2350, $M+Cs^+$ calcd for $C_{39}H_{56}O_{11}SSi$ 893.2367.

DiTES taxoid 55. To a sulution of alcohol 54 (21.8 mg, 0.0286 mmol, prcviously azenti-oped twice with benzcnc) and β-lactam 24 (33.0 mg, 0.0866 mmol, previously azentroped twice with benzene) in THF (1.1 mL) at 0° C., prepared from thc Ojima-Holton. protocol (Holton, R. A. Chem Abstr. 1990. 114, 164568q; Ojima, I.; Habus, I.; Zliao, M.- Georg, (C. T.: Jayasinghe, L. R. J. Org. Chem. 1991. 56, 1681–1683; Ojima, 1.; Habus, I.; Zhlao. M.: Zucco. M., Park, Y. H.; Sun, C. M..; Brigaud. T. Tetrnhedron 1992, 48, 6985–7012), was added $NaN(SiMe_3)_2$ (0.086 mL of a 1.0 M solution in THF, 0.086 mmol) dropwise. The resulting solution was stirred for 20 min and poured into a mixture of $C_2Cl_2$ (10 mL) and aqueous $NH_4Cl$ (5 mL). The organic layer was separated and the aqueous laycr was extracted with $CH_2Cl_2$ (2×5 mL). Thc combined organic layer was washed with brine (5 mL), dried ($MgSO_4$), concentrated, and purified by flash chromatography (silica, 15→30→50% ethylacetate in petrolcum ether) to give 55 (13.8 mg, 42%) as an amorphous solid.

Physical Data for DiTES taxoid 55. $R_f$=0.40 (silica, 30% etylacetate in hexanes); IR (film) $v_{max}$ 3437, 2952, 2879, 1735. 1662, 1482, 1369, 1236, 1128, 981, 740 $cm^{-1}$; $^1H$ NMR (500 MHz, $CDCl_3$) δ7.82–7.76 (m, 2 H), 7.54–7.16 (band, 13 H), 7.11 (d, J=9.0 Hz, 1 H, NH), 6.41 (s, 1 H, 10-H), 6.18 ( hr r, J=9.0 Hz, 1 H, 13-H), 5.62 (dd, J=9.0, 2.0 Hz, 1 H, 3'-H), 5.49 (d, J=7.0 Hz. 1H, 2-H). 4.93 (dd, J=9.5, 2.0 Hz, 1 H, 5-II), 4.64 (d. J=2.0 Hz, 1 H, 2'-H), 4.42 (dd, J=10.5, 6.5 Hz. 1 H, 7-H), 4.40 (d, J=8.0 Hz, 1 H, 20-H), 4.21 (d, J=8.0 Hz, 1 H, 20-H), 3.70 (d, J=7.0 IIz, 1 H, 3-H) 3.23–3.17 (m, 2 H, $CH_2SPh$), 2.78 2.69 (m, 1 H, $HCHCH_2SPh$), 2.67–2.57 (m, 1 H, $HCIICII_2SPh$), 2.55–2.46 (m, 2 H, 6-H, OH), 2.38 (s, 3 H, Me), 2.27–2.10 (m, 2 H, 14-$CH_2$), 2.16 (s, 3 H, Me), 1.98 (d. J=1.0 Hz, 3 H, Me), 1.89 (ddd, J=14.0, 11.0, 2.0 Hz, 1 H, 6-H), 1.64 (s, 3 H, Me), 1.18 (s, 3 H, Me), 1.17 (s, 3 H, Me), 0.91 (t, J=8.0 Hz, 9 H, $OSi(CH_2CH_3)_3$), 0.81 (t, J=8.0 Hz, 9 H, $OSi(CII_2CH_3)_3$), 0.64–0.36 (band, 12 H, $OSi(CH_2CII_3)_3$); FAB HRMS (NBA/CsI) m/e $M+Cs^+$1274.4125 calcd for $C_{61}H_{83}O_{14}SSi_2$ 1274.4127.

Taxoid 56. A solution of silyl ether 55 (8.1 mg, 0.0071 mmol) in THF (0.5 mL) at 25° C. was treated with HF•pyridine (0.150 mL) and stirred for 3.75 h. The reaction mixture was poured into a mixture of ethylacetate (10 mL) and aqueous $NaHCO_3$ (5 mL) and the resulting mixture was stirred for 10 min. The organic layer was separated and the aqueous layer was extracted with ethylacetate (2×10 mL). The combined organic layer was washed with brine (5 mL), dried ($MgSO_4$), concentrated, and purified by preparative TLC (silica, 60% ethylacetate in petroleum ether) to give 56 (3.2 mg, 49%) as a colorless film.

Physical Data for Taxoid 56. $R_f$=0.39 (silica, 60% ethylacetate in petroleum ether); IR (film) $v_{max}$ 3426, 2928, 1731, 1642, 1371, 1238, 1070, 739, 709 $cm^{-1}$; $^1H$ NMR (500 MHz, $CDCl_3$) δ7.80–7.75 (m, 2 H), 7.55–7.18 (band, 13 H), 6.94 (d, J=9.0 Hz, 1 H, NH), 6.23 (s, 1 H, 10-H), 6.19 (br t, J=9.0 Hz, 1 H, 13-H), 5.74 (dd, J=9.0, 2.5 Hz, 1 H, 3'-H), 5.47 (d, J=7.0 Hz, 1 H, 2-H), 4.93 (dd, J=9.5, 2.0 Hz, 1 H, 5-H), 4.74 (dd, J=5.0, 2.5 Hz, 1 H, 2'-H), 4.38 (d, J=8.0 Hz, 1 H, 20-H), 4.35 (ddd, J=11.0, 6.5 Hz,-4.5 Hz, 1 H, 7-H), 4.21 (d, J=8.0 Hz, 1 H, 20-H), 3.67 (d, J=7.0 Hz, 1 H, 3-H), 3.51 (d, J=5.0 Hz, 1 H, 2'-OH), 3.28–3.14 (m, 2 H, $CH_2SPh$), 2.77–2.68 (m, 1 H, $HCHCH_2SPh$), 2.67–2.59 (m, 1 H, $HCHCH_2SPh$), 2.54 (ddd, J=14.5, 9.5, 6.5 Hz, 1 H, 6-H), 2.44 (d, J=4.5 Hz, 1 H, 7-OH), 2.36 (dd; J=15.5, 9.0 Hz, 1 H, 14-H), 2.26 (br s, 1 H, OH), 2.23 (s, 3 H, Me), 2.21 (s, 3 H, Me), 2.18 (dd, J=15.5, 9.0 Hz, 1 H, 14-H), 1.88 (ddd, J=14.5, 11.0, 2.0 Hz, 1 H, 6-H), 1.75 (d, J=1.0 Hz, 3 H, Me), 1.63 (s, 3 H, Me), 1.24 (s, 3 H, Me), 1.10 (s, 3 H, Me); FAB HRMS (NBA/CsI) m/e 1046.2410, $M+Cs^+$ calcd for $C_{49}H_{55}O_{14}NS$ 1046.2398.

Preparation of MPA taxoid 57

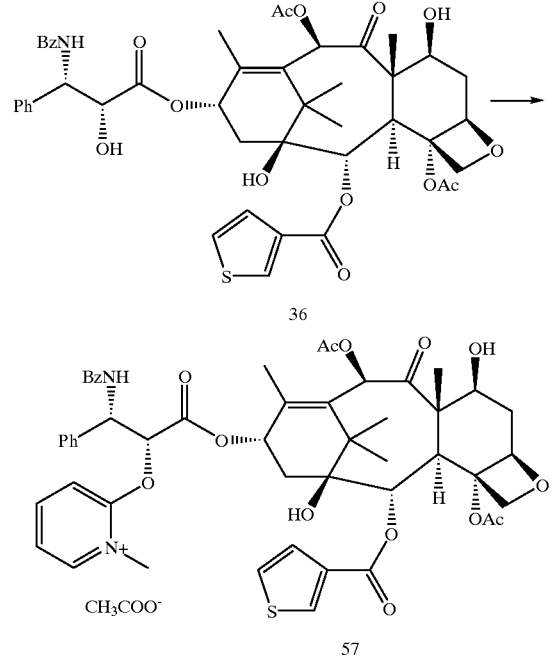

MPA taxoid 57. A solution of taxoid 36 (4.3 mg, 0.005 mmol) and triethylamine (0.0033 mL, 0.0237 mmol) in $CH_2Cl_2$ (0.2 mL) at 25° C. was treated with 2-fluoro-1-methylpyridinium p-toluenesulfonate (2.1 mg, 0.0075 mmol) and stirred for 35 min. The clear colorless solution rapidly turned to a clear pale yellow. The course of the reaction was monitored through thin layer chromatography (TLC)(E. Merck RP- 18 silica, 65 tetrahydrofuran: 35 water, UV/phospho-molybidic acid) and after thirty minutes of stirring at ambient temperature, judged complete as no taxol remained and only one compound was apparent by TLC. The reaction mixture was directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give 36 (0.8 mg, 19%) and 57 (4.1 mg, 100% based on 81% conversion) as a colorless film.

Physical Data for taxoid 57 $^1$H NMR (500 MHz, CDCl$_3$) δ10.5 (d, J=7.5 Hz, 1 H), 8.44 (ddd, J=9.0, 7.5, 2.0 Hz, 1 H), 8.33–8.29 (m, 2 H), 8.15 (dd, J=3.0, 1.0 Hz, 1 H, thiophene), 8.12 (br d, J=6.0 Hz, 1 H), 7.84 (br d, J=8.5 Hz, 1 H), 7.74–7.69 (m, 2 H), 7.53 (dd, J=5.0, 1.0 Hz, 1 H, thiophene), 7.48–7.34 (band, 7H), 7.16–7.12 (m, 1 H), 6.53–6.43 (m, 1 H, 2'-H), 6.21 (s, 1 H, 10-H), 6.03 (dd, J=10.5, 8.0 Hz, 1 H, 3'-H), 5.82 (br t, J=9.0 Hz, 1 H, 13-H), 5.44 (d, J=7.0 Hz, 1 H, 2-H), 4.90 (dd, J=9.5, 2.0 Hz, 1 H, 5-H), 4.33 (dd, J=11.0, 6.5 Hz, 1 H, 7-H), 4.30 (d, J=8.0 Hz, 1 H, 20-H), 4.15 (d, J=8.0 Hz, 1 H, 20-H), 4.08 (s, 3 H, N+Me), 3.68 (d, J=7.0 Hz, 1 H, 3-H), 2.58–2.49 (m, 1 H, 6-H), 2.52 (s, 3 H, OAc), 2.21 (s, 3 H, OAc), 2.04 (s, 3 H, OAc), 2.02 (br s, 2 H, OH, OH), 1.88 (ddd, J=14.5, 11.5, 2.0 Hz, 1 H, 6-H), 1.78 (br s, 3 H, 18-Me), 1.64 (s, 3 H, Me), 1.61 (dd, J=16.0, 7.0 Hz, 1 H, 14-H), 1.18 (dd, J=16.0, 9.0 Hz, 1 H, 14-H), 1.13 (s, 3 H, Me), 1.08 (s, 3 H, Me).

Preparation of MPA taxoid 58

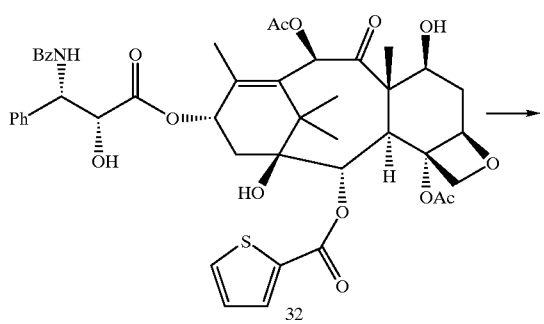

32

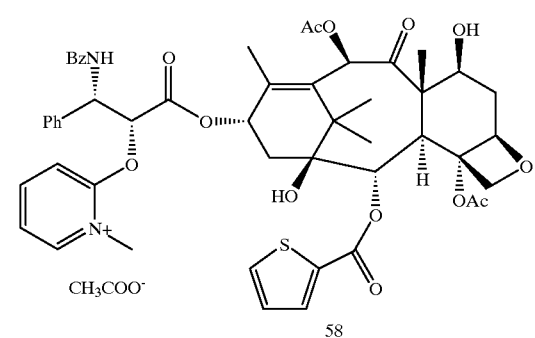

58

MPA taxoid 58. A solution of taxoid 32 (1.0 equiv.) and triethylamine (4.7 equiv.) in CH$_2$Cl$_2$ (0.025 M) at 25° C. is treated with 2-fluoro-1-methylpyridinium p-toluenesulfonate from Aldrich Chemical company inc. (1.5 equiv.) and stirred for 35 minutes. The course of the reaction was monitored through thin layer chromatography (TLC)(E. Merck RP-18 silica, 65 tetrahydrofuran: 35 water, UV/phospho-molybidic acid) and after thirty minutes of stirring at ambient temperature, judged complete as no taxol remained and only one compound was apparent by TLC. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give 58 as a colorless film.

Preparation of MPA taxoid 59

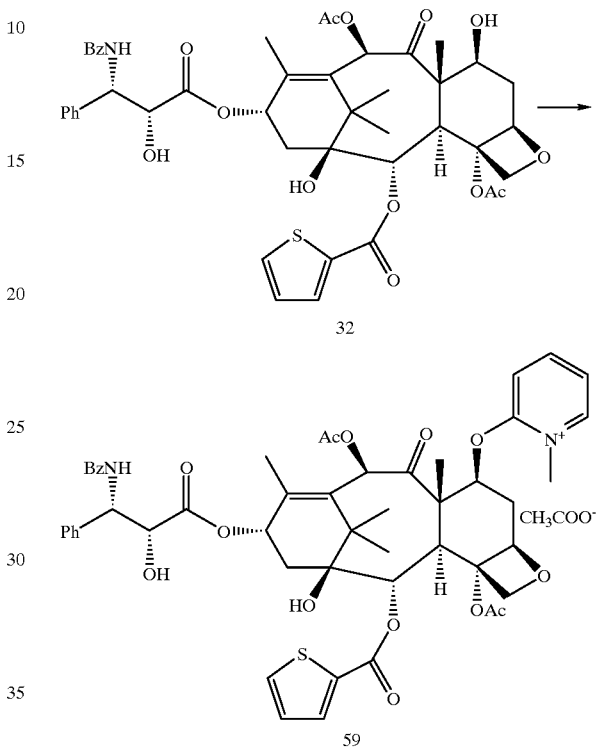

32

59

MPA taxoid 59. The synthesis of the taxoid-7-MPA 59 differs only slightly from the synthesis of taxoid-2'-MPA 58. The C-2 taxoid 32 is dissolved in methylene chloride (0.006 M) and treated sequentially with triethylamine (40 equivalents) and 2-fluoro-1-methyl-pyridinium tosylate (10 equivalents) Aldrich Chemicals, and allowed to stir at ambient temperature for 5 minutes. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give 59 as a colorless film.

Preparation of MPA taxoid 60

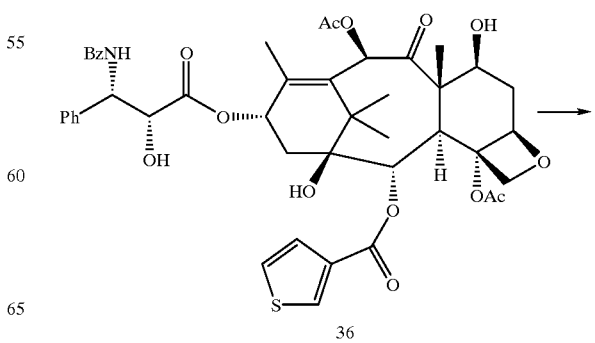

36

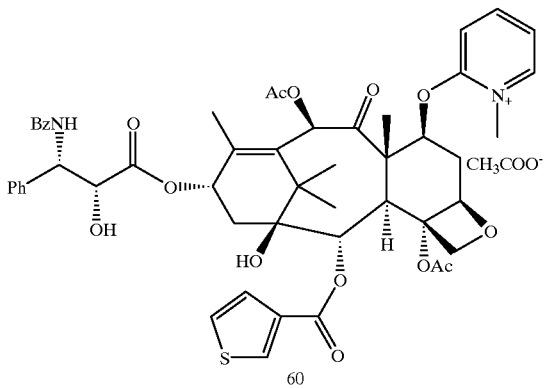

60

MPA taxoid 60. The synthesis of the taxoid-7-MPA 60 differs only slightly from the synthesis of taxoid-2'-MPA 57. The C-2 taxoid 36 is dissolved in methylene chloride (0.006 M) and treated sequentially with triethylamine (40 equivalents) and 2-fluoro-1-methyl-pyridinium tosylate (10 equivalents) Aldrich Chemicals, and allowed to stir at ambient temperature for 5 minutes. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give 60 as a colorless film.

Preparation of C-2-taxoid-2'-methyl-pyridinium salts

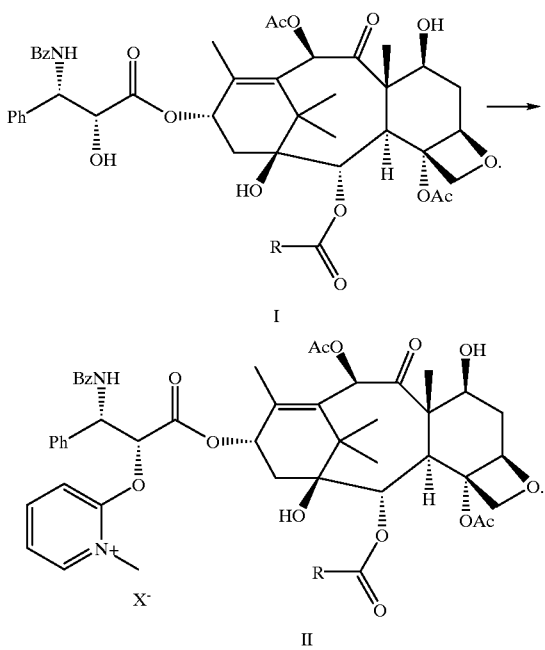

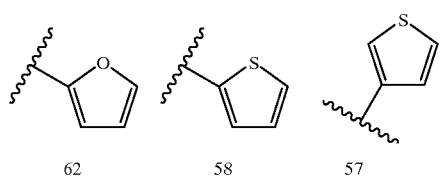

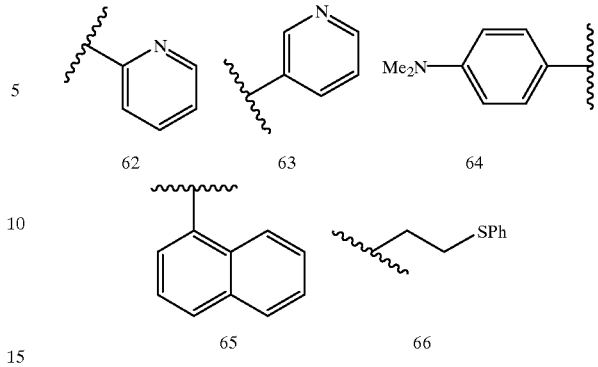

C-2-taxoid-2'-onium salts 62–66. A solution of taxoid (62–66) 1. (1.0 equiv.) and triethylamine (4.7 equiv.) in CH$_2$Cl$_2$ (0.025 M) at 25° C. is treated with 2-fluoro-1-methylpyridinium p-toluenesulfonate from Aldrich Chemical company inc. (1.5 equiv.) and stirred for 35 minutes. The course of the reaction was monitored through thin layer chromatography (TLC)(E. Merck RP-18 silica, 65 tetrahydrofuran: 35 water, UV/phospho-molybidic acid) and after thirty minutes of stirring at ambient temperature, judged complete as no taxol remained and only one compound was apparent by TLC. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give (62–66) II. as a colorless film.

Preparation of C-2-taxoid-7-methyl-pyridinium salts

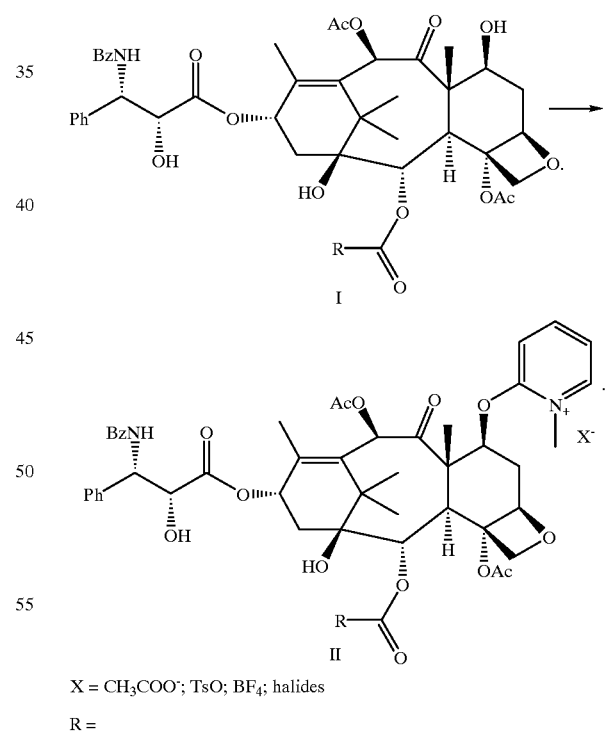

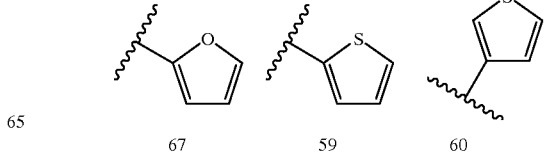

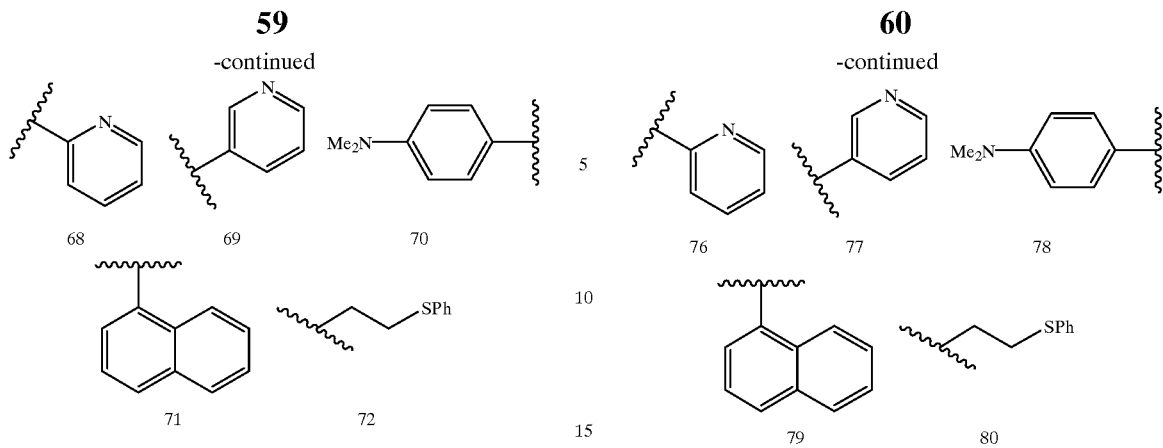

C-2-taxoid-7-onium salts 67–72. The synthesis of the taxoid-7-methyl-pyridinium salts (67–72) II, differs only slightly from the synthesis of taxoid-2'-methyl-pyridinium salts (62–66) II. The C-2 taxoid (67–72) I is dissolved in methylene chloride (0.006 M) and treated sequentially with triethylamine (40 equivalents) and 2-fluoro-1-methyl-pyridinium tosylate (10 equivalents) Aldrich Chemicals, and allowed to stir at ambient temperature for 5 minutes. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give (67–72) II as a colorless film.

Preparation of C-2-taxoid-bis-2',7-methyl-pyridinium salts

C-2-taxoid-bis-2',7-onium salts 73–80. The synthesis of C-2-taxoid-bis-2',7-methyl-pyridinium salts II (73–80), differs from the synthesis of taxoid-7-methyl-pyridinium salts (67–72) II only with respect to reaction time. The C-2 taxoid (73–80) I is dissolved in methylene chloride (0.006 M) and treated sequentially with triethylamine (40 equivalents) and 2-fluoro-1-methyl-pyridinium tosylate (10 equivalents) Aldrich Chemicals, and allowed to stir at ambient temperature for 18 hours. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give (73–80) II as a colorless film.

Preparation of C-2-taxoid-2'-benzothiazolium salts

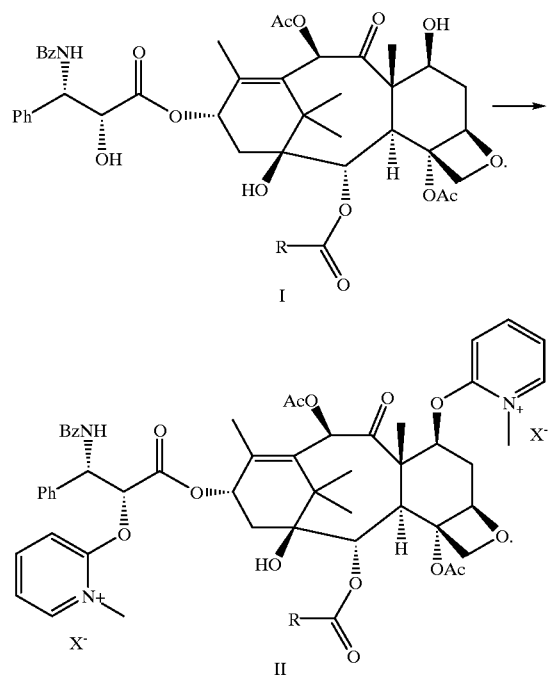

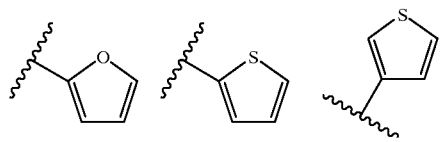

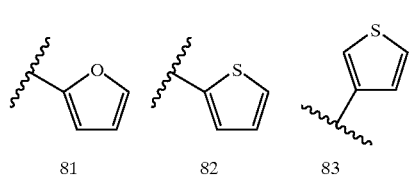

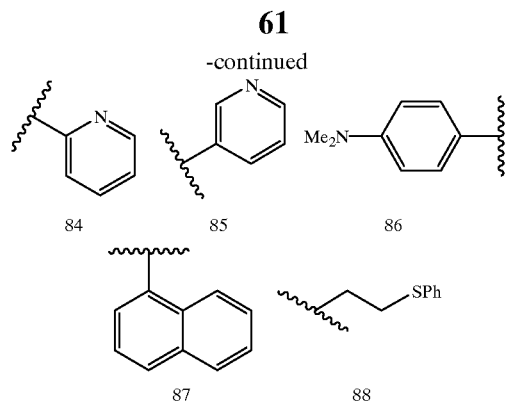

84  85  86

87  88

C-2-taxoid-2'-benzothiazolium salts 81–88. A solution of taxoid 81–88 (1.0 equiv.) and triethylamine (4.7 equiv.) in $CH_2Cl_2$ (0.025 M) at 25° C. is treated with 2-fluoro-1-methylpyridinium p-toluenesulfonate from Aldrich Chemical company inc. (1.5 equiv.) and stirred for 35 minutes. The course of the reaction was monitored through thin layer chromatography (TLC)(E. Merck RP-18 silica, 65 tetrahydrofuran: 35 water, UV/phospho-molybidic acid) and after thirty minutes of stirring at ambient temperature, judged complete as no taxol remained and only one compound was apparent by TLC. The reaction mixture is then directly purified by HPLC (Vydak RP-18, 22.5×3 mm, A→B 0.5 h linear, A: 20% MeOH in 20 mM $NH_{40}Ac$, B: 100% MeOH, 9 mL/min. RT=26.12) to give 81–88 as a colorless film.

Preparation of C-2-taxoid-7-benzothiazolium salts

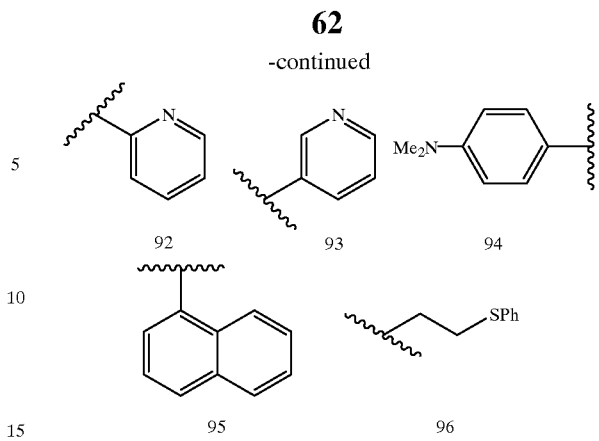

92  93  94

95  96

C-2-taxoid-7-benzothiazolium salts (89–96). The synthesis of the taxoid-7-benzothiazolium salts (89–96) II, differs only slightly from the synthesis of taxoid-2'-benzothiazolium salts (81–88) II. The C-2 taxoid (89–96) I is dissolved in methylene chloride (0.006 M) and treated sequentially with triethylamine (40 equivalents) and 2-fluoro-3-ethylbenzothiazolium tetrafluoroborate (10 equivalents) Aldrich Chemicals, and allowed to stir at ambient temperature for 5 minutes. The reaction mixture is then directly purified by HPLC (Vydak RP-18, 22.5×3 mm, A→B 0.5 h linear, A: 20% MeOH in 20 mM $NH_4OAc$, B: 100% MeOH, 9 mL/min, RT=26.12) to give (89–96) II as a colorless film.

Preparation of C-2-taxoid-2'-benzoxazolium salts

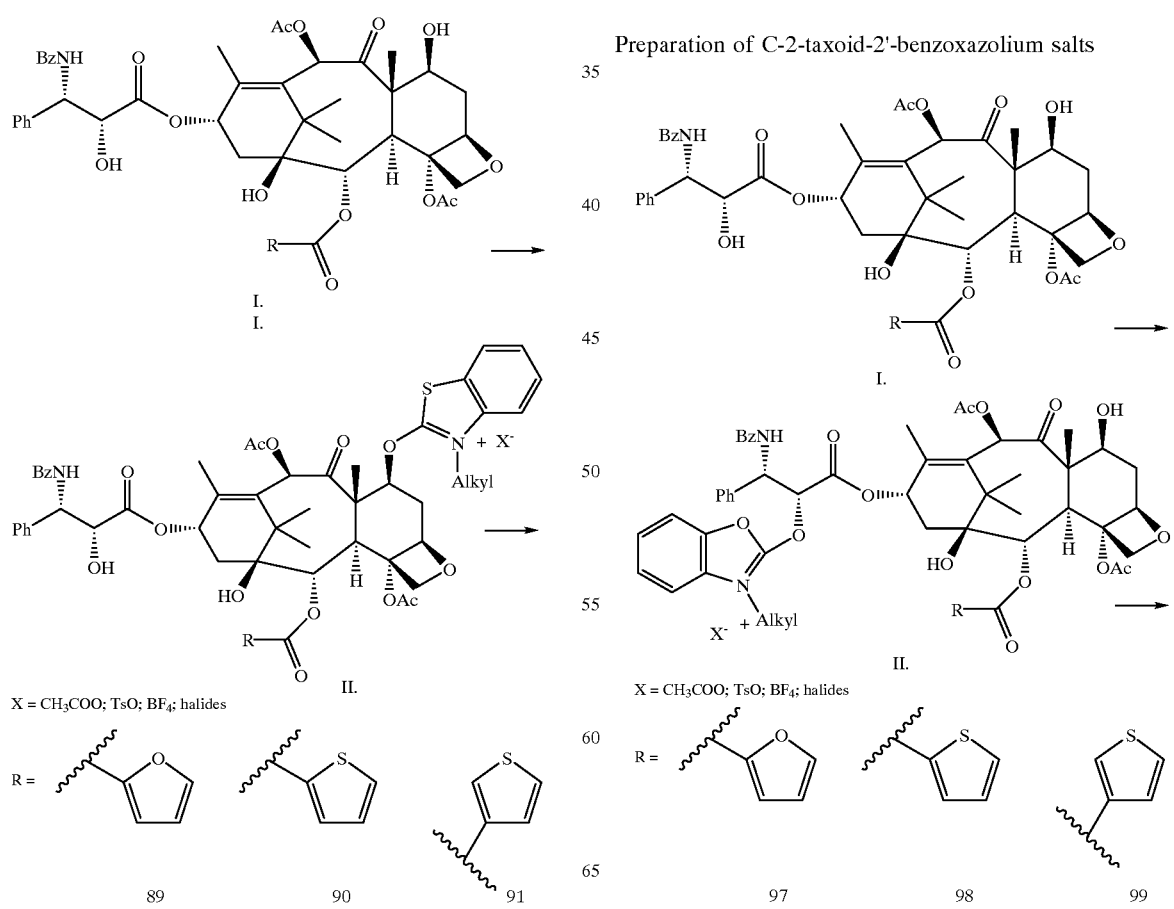

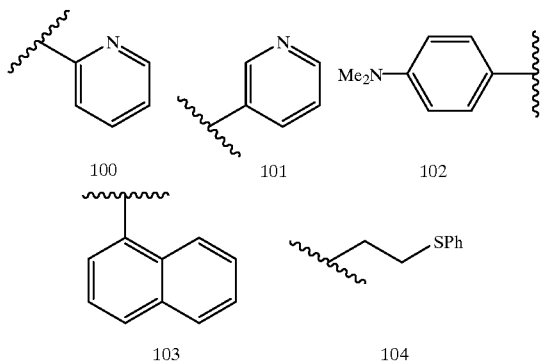

100   101   102

103   104

C-2-taxoid-2'-benzoxazolium salts 97–104. A solution of taxoid (97–104) I. (1.0 equiv.) and triethylamine (4.7 equiv.) in $CH_2Cl_2$ (0.025 M) at 25° C. is treated with 2-chloro-3-ethylbenzoxazolium tetrafluoroborate from Aldrich Company (1.5 equiv.) and stirred for 35 minutes. The course of the reaction was monitored through thin layer chromatography (TLC)(E. Merck RP-18 silica, 65 tetrahydrofuran: 35 water, UV/phospho-molybidic acid) and after thirty minutes of stirring at ambient temperature, judged complete as no taxol remained and only one compound was apparent by TLC. The reaction mixture is then directly purified by HPLC (Vydak RP-18, 22.5×3 mm, A→B 0.5 h linear, A: 20% MeOH in 20 mM $NH_4OAc$, B: 100% MeOH, 9 mL/min, RT=26.12) to give (97–104) II. as a colorless film.

Preparation of C-2-taxoid-7-benzoxazolium salts

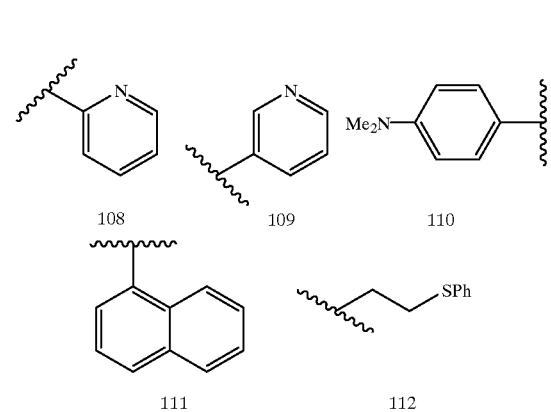

108   109   110

111   112

C-2-taxoid-7-benzoxazolium salts (105–112). The synthesis of the taxoid-7-benzoxazolium salts (105–112) II, differs only slightly from the synthesis of taxoid-2'-benzoxazolium salts (97–104) II. The C-2 taxoid (105–112) I is dissolved in methylene chloride (0.006 M) and treated sequentially with triethylamine (40 equivalents) and 2-chloro-3-ethylbenzoxazolium tetrafluoroborate from Aldrich Company (10 equivalents) Aldrich Chemicals, and allowed to stir at ambient temperature for 5 minutes. The reaction mixture is then directly purified by HPLC (Vydak RP-18, 22.5×3 mm, A→B 0.5 h linear, A: 20% MeOH in 20 mM $NH_4OAc$, B: 100% MeOH, 9 mL/min, RT=26.12) to give (105–112) II as a colorless film.

Preparation of C-2-taxoid-2'-pyrimidinium salts

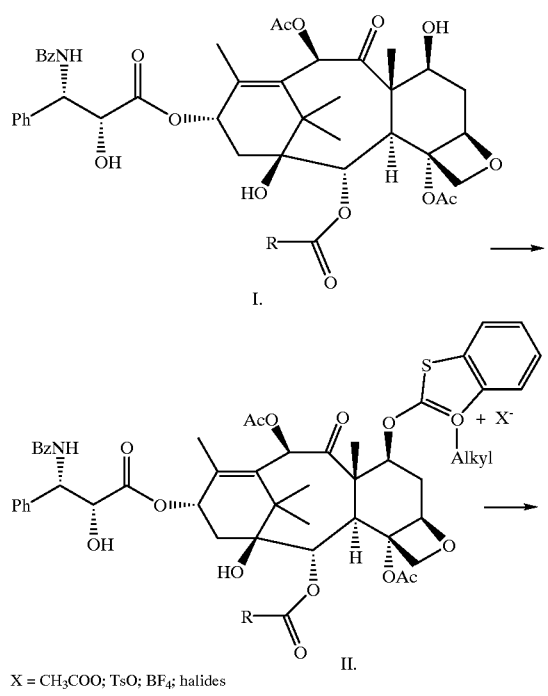

X = $CH_3COO$; TsO; $BF_4$; halides

R = 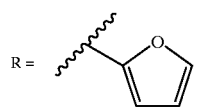 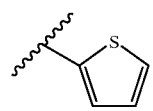 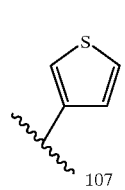

105   106   107

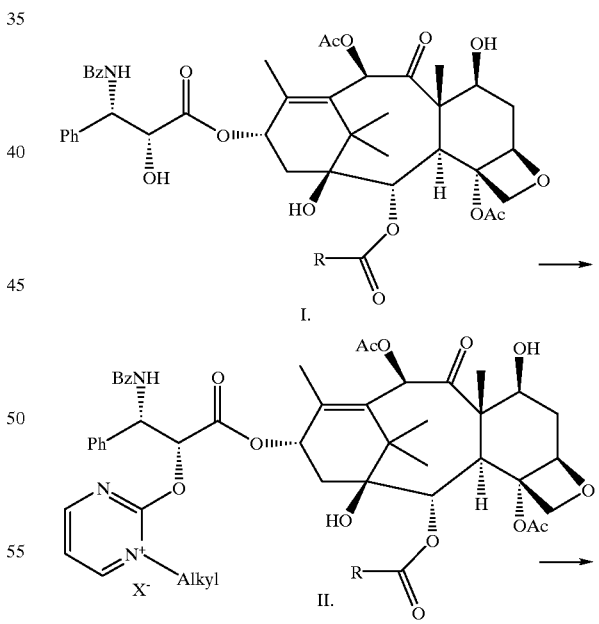

X = $CH_3COO$; TsO; $BF_4$; halides

R = 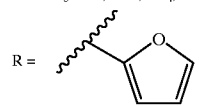 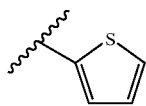 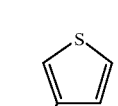

113   114   115

-continued

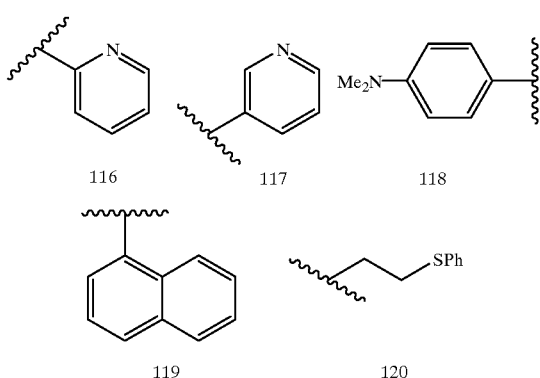

116  117  118

119  120

C-2-taxoid-2'-pyrimidinium salts 113–120. A solution of taxoid (113–120) I. (1.0 equiv.) and triethylamine (4.7 equiv.) in CH$_2$Cl$_2$ (0.025 M) at 25° C. is treated with 2-chloro-methyl-pyrimidinium fluoride from Aldrich Company (1.5 equiv.) and stirred for 35 minutes. The course of the reaction was monitored through thin layer chromatography (TLC)(E. Merck RP- 18 silica, 65 tetrahydrofuran: 35 water, UV/phospho-molybidic acid) and after thirty minutes of stirring at ambient temperature, judged complete as no taxol remained and only one compound was apparent by TLC. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give (113–120) II. as a colorless film.

Preparation of C-2-taxoid-7-pyrimidinium salts

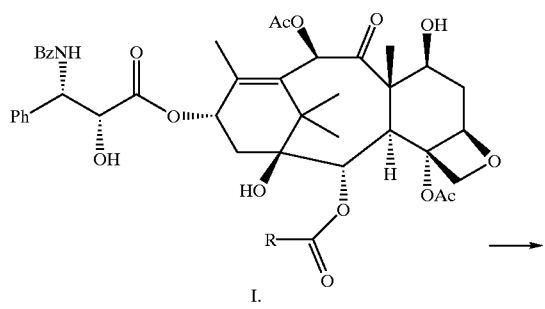

I.

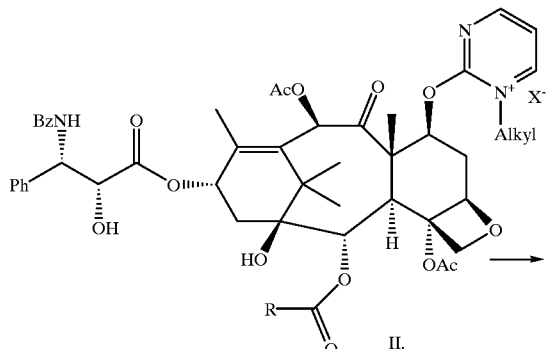

X = CH$_3$COO; TsO; BF$_4$; halides

II.

-continued

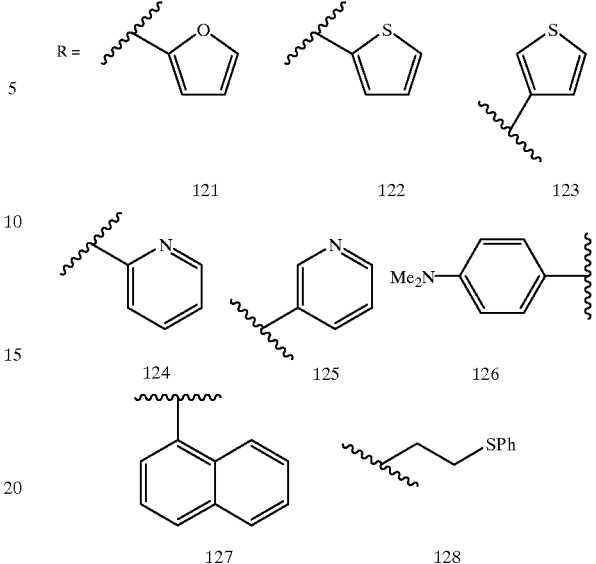

R = 121  122  123

124  125  126

127  128

C-2-taxoid-7-pyrimidinium salts (121–128). The synthesis of the taxoid-7-pyrimidinium salts (121–128) II, differs only slightly from the synthesis of taxoid-2'-pyrimidinium salts (113–120) II. The C-2 taxoid (121–128) I is dissolved in methylene chloride (0.006 M) and treated sequentially with triethylamine (40 equivalents) and 2-chloro-methyl-pyrimidinium fluoride from Aldrich Company (10 equivalents), and allowed to stir at ambient temperature for 5 minutes. The reaction mixture is then directly purified by HPLC (Vydak RP-18, 22.5×3 mm, A→B 0.5 h linear, A: 20% MeOH in 20 mM NH$_4$OAc, B: 100% MeOH, 9 mL/min, RT=26.12) to give (121–128) II as a colorless film.

What is claimed is:

1. A cyclic method employing chemical switching for solubilizing and desolubilizing a taxo-diterpenoid with respect to an aqueous solvent, an underivatized form of the taxo-diterpenoid having a low solubility and including a reactive C''-hydroxyl, the method comprising the following steps:

Step A: converting the underivatized form of the taxo-diterpenoid from low solubility to high solubility by derivatizing the reactive C''-hydroxyl with an onium salt of a 2-halogenated aza-arene to form an onium salt of a taxo-diterpenoid-C'',2-O-aza-arene derivative having high solubility, wherein the onium salt of the 2-halogenated aza-arene is represented by the following structures I and II:

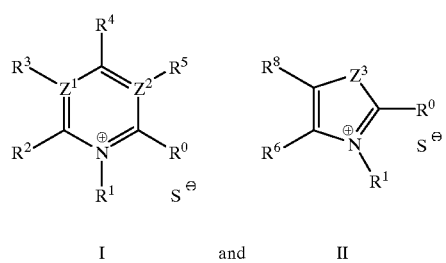

I  and  II wherein:

R$^0$ is a halogen selected from the group consisting of Cl, Br, F, and I;

$Z^1$ and $Z^2$ are each selected from the group consisting of C and N;

$Z^3$ is selected from the group consisting of S and O;

$R^1$ is selected from the goup consisting of $C_1$–$C_6$ alkyl, allyl, arenxyl, propargyl, and fused aryl;

$R^2$ and $R^6$ are each selected from the group consisting of H, $C_1$–$C_6$ alkyl, allyl, arenxyl, propargyl, and fused aryl;

if $Z^1$ is C, then $R^3$ is selected from the group consisting of H, $C_1$–$C_6$ alkyl, allyl, arenxyl, proparyl, $C_1$–$C_6$ O-alkyl, OH, halogen, and fused aryl;

if $Z^1$ is N, then $R^3$ is absent;

$R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and if $Z^2$ is C, then $R^5$ is selected from the group consisting of H, $C_1$–$C_6$ alkyl, allyl, arenxyl, propargyl, $C_1$–$C_6$ O-alkyl, OH, halogen, and fused aryl;

if $Z^2$ is N, then $R^5$ is absent, and $S^-$ is a counter ion; and then

Step B: converting the onium salt of the taxo-diterpenoid-$C^n$,2-O-aza-arene derivative produced in said Step A from high solubility by contacting the taxo-diterpenoid-$C^n$,2-O-aza-arene derivative with a serum protein for displacing the 2-O-aza-arene and forming a protein:taxo-diterpenoid intermediate, the protein:taxo-diterpenoid intermediate then dissociating to produce the underviatized form the onium salt of the 2-halogenated aza-arene employed in said Step A being selected from the group consisting of onium salts represented by the above indicated formulas II and III wherein:

$R^0$ is a halogen selected from the group consisting of Cl, Br, F, and I; and then Step B: converting the onium salt of the taxo-diterpenoid-$C^n$,2-O-aza-arene derivate produced in said Step A from high solubility to low solubility by contacting the taxo-diterpenoid-$C^n$,2-O-aza-arene derivative with a serum protein for displacing the 2-O-aza-arene and forming a protein:taxo-diterpenoid intermediate, the protein:taxo-diterpenoid intermediate then dissociating to produce the underviatized form of the taxo-diterpenoid employed in said Step A.

3. A cyclic method employing chemical switching for solubilizing and desolubilizing a taxo-diterpenoid with respect to an aqueous solvent, an underivatized form of the taxo-diterpeniod having a low solubility and including a reactive $C^n$-hydroxyl, the method comprising the following steps:

Step A: converting the underivatized form of the taxo-diterpenoid from low solubility to high solubility by derivating the reactive $C^n$-hydroxyl with an onium salt of a 2-halogenated aza-arene to form an onium salt of a taxo-diterpeniod-$C^n$,2-O-aza-arene derivative having high solubility, wherein the onium salt of the 2-halogenated aza-arene is represented by the following structures I and II:

I and II wherein:
$R^0$ is a halogen selected from the group consisting of Cl, Br, F, and I;
$Z^1$ and $Z^2$ are each selected from the group consisting of C and N;
$Z^3$ is selected from the group consisting of S and O;
$Z^1$ is selected from the group consisting of $C_1$–$C_6$ alkyl, allyl, arenxyl, propargyl, and fused aryl;
$R^2$ and $R^6$ are each selected from the group consisting of H, $C_1$–$C_6$ alkyl, allyl, arenxyl, propargyl, and fused aryl;
if $Z^1$ is C, then $R^3$ is selected from the group consisting of H, $C_1$–$C_6$ alkyl, allyl, arenxyl, propargyl, $C_1$–$C_6$ O-alkyl, OH, halogen, and fused aryl;
if $Z^1$ is N, then $R^3$ is absent;
$R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and
if $Z^2$ is C, then $R^5$ is selected from the group consisting of H, $C_1$–$C_6$ alkyl, allyl, arenxyl, propargyl, $C_1$–$C_6$ O-alkyl, OH, halogen, and fused aryl;
if $Z^2$ is N, then $R^5$ is absent; and
S⁻ is a counter ion; then Step B: contacting the taxo-diterpenoid-$C^n$,2-O-aza-arene derivative produced in said Step A with serum protein for displacing the 2-O-aza-arene and forming a protein:taxo-diterpenoid intermediate having a high solubility; and then Step C: converting the taxo-diterpenoid:protein conjugate produced in said Step B from high solubility to low solubility by releasing the taxo-diterpeniod from the protein:taxo-diterpenoid conjugate to produce the underviatized form of the taxo-diterpenoid employed in said Step A.

4. A method for solubilizing a taxo-diterpenoid with respect to an aqueous solvent, the taxo-diterpenoid including a reactive $C^n$-hydroxyl, the method comprising the following step:

Step A: converting the taxo-diterpenoid from low solubility to high solubility by derivatizing the $C^n$-hydroxyl with an onium salt of a 2-halogenated aza-arene to form an onium salt of a taxo-diterpenoid-$C^n$,2-O-aza-arene derivative having high solubility, wherein the onium salt of the 2-halogenated aza-arene is represented by the following structures I and II:

I and II wherein:
$R^0$ is a halogen selected from the group consisting of Cl, Br, F, and I;
$Z^1$ and $Z^2$ are each selected from the group consisting of C and N;
$Z^3$ is selected from the group consisting of S and O;
$R^1$ is selected from the group consisting of $C_1$–$C_6$ alkyl, allyl, arenxyl, propargyl, and fused aryl;
$R^2$ and $R^6$ are each selected from the group consisting of H, $C_1$–$C_6$ alkyl, allyl, arenxyl, propargyl, and fused aryl;
if $Z^1$ is C, then $R^3$ is selected from the group consisting of H, $C_1$–$C_6$ alkyl, allyl, arenxyl, propargyl, $C_1$–$C_6$ O-alkyl, OH, halogen, and fused aryl;
if $Z^1$ is N, then $R^3$ is absent;
$R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and
if $Z^2$ is C, then $R^5$ is selected from the group consisting of H, $C_1$–$C_6$ alkyl, allyl, arenxyl, propargyl, $C_1$–$C_6$ O-alkyl, OH, halogen, and fused aryl;
if $Z^2$ is N, then $R^5$ is absent; and
S⁻ is a counter ion.

5. A method for solubilizing an underivatized form of a taxo-diterpenoid having a low solubility with respect to an aqueous solvent, the underivated form of the taxo-diterpenoid including a reactive $C^n$-hydroxyl, the method comprising the following steps:

Step A: converting the underivatized form of the taxo-diterpenoid from low solubility to high solubility by derivatizing the reactive $C^n$-hydroxyl with an onium salt of a 2-halogenated aza-arene to form an onium salt of a taxo-diterpenoid-$C^n$,2-O-aza-arene derivative having high solubility, the underivatized form of the taxo-diterpeniod being represented by formula I as follows:

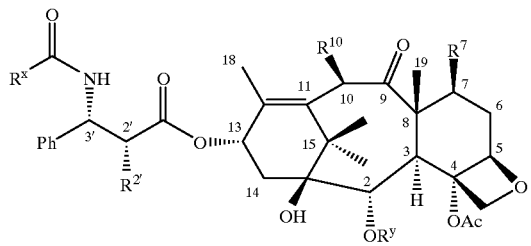

I wherein:

C" is selected from the group of C⁷ and C²';

$R^x$ is selected from the group consisting of Ph and tBuO;

$R^{10}$ is selected from the group consisting of OAc and OH; and $R^y$ is selected from the group consisting of benzyl and the following structures:

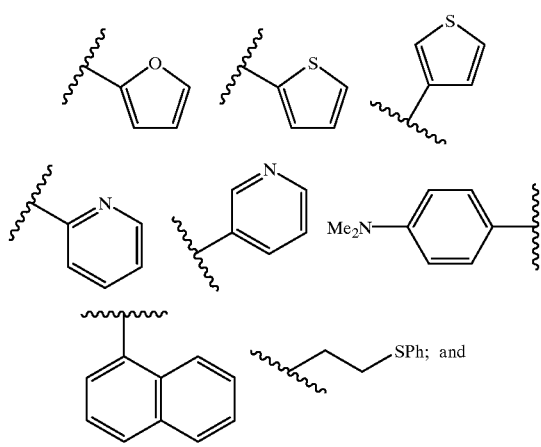

$R^{2'}$ and $R^7$ are each OH;

the onium salt of the taxo-diterpenoid-C",2-O-aza-arene derivative produced in said Step A being represented by the above formula I wherein:

$R^{2'}$ and $R^7$ are each selected from the group consisting of OH and an onium salt of a 2-O-aza-arene, with the proviso that at least one of $R^{2'}$ and $R^7$ is said onium salt of the 2-O-aza-arene, said onium salt of the 2-O-aza-arene being selected from the group consisting of onium salts represented by the following formulas II and III:

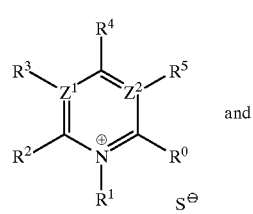

and

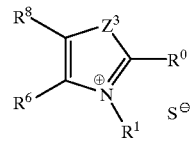

III wherein:

$R^0$ is oxygen and is bonded to C";

$Z^1$ and $Z^2$ are each selected from the group consisting of C and N;

$Z^3$ is selected from the group consisting of S and O;

$R^1$ is selected from the group consisting of $C_1$–$C_6$ alkyl, allyl, arenxyl, propargyl, and fused aryl;

$R^2$ and $R^6$ are each selected from the group consisting of H, $C_1$–$C_6$ alkyl, allyl, arenxyl, progargyl, and fused aryl;

if $Z^1$ is C, then $R^3$ is selected from the group consistng of H, $C_1$–$C_6$ alkyl, allyl, arenxyl, propargyl, $C_1$–$C_6$ O-alkyl, OH, halogen, and fused aryl;

if $Z^1$ is N, then $R^3$ is absent;

$R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and if $Z^2$ is C, then $R^5$ is selected from the group consisting of H, $C_1$–$C_6$ alkyl, allyl, arenxyl, progargyl, $C_1$–$C_6$ O-alkyl, OH, halogen, and fused aryl;

if $Z^2$ is N, then $R^5$ is absent; and

S⁻ is a counter ion; and the onium salt of the 2-halogenated aza-arene employed in said Step A being selected from the group consisting of onium salts represented by the above indicated formulas II and III wherein:

$R^0$ is a halogen selected from the group consisting of Cl, Br, F, and I.

6. A method for solubilizing a taxo-diterpenoid as described in claim 4, comprising the following additional step:

after said Step A

Step B: converting the onium salt of the taxo-diterpenoid-C",2-O-aza-arene derivative produced in said Step A to a taxo-diterpenoid:protein conjugate by displacement of 2-O-aza-arene and conjugation with a serum protein, the taxo-diterpenoid:protein conjugate having high solubility.

7. A method for converting an onium salt of a taxo-diterpenoid-C",2-O-aza-arene derivative into a taxo-diterpenoid:protein conjugate, the method employing the following step:

contacting the onium salt of the taxo-diterpeniod-C",2-O-aza-arene derivative with a serum protein for displacing 2-O-aza-arene and conjugating the taxo-diterpeniod with the serum protein to produce the taxo-diterpeniod:protein conjugate, the 2-O-aza-arene being selected from the group consisting of onium salt I and onium salt II represented by the following formulas:

Onium Salt I

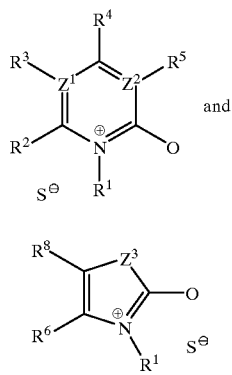

and

Onium Salt II wherein:
- $Z^1$ and $Z^2$ are each selected from the group consisting of C and N;
- $Z^3$ is selected from the group consisting of S and O;
- $R^1$ is selected from the group consisting of $C_1$–$C_6$ alkyl, allyl, arenxyl, propargyl, and fused aryl;
- $R^2$ and $R^6$ are each selected from the group consisting of H, $C_1$–$C_6$ alkyl, allyl, arenxyl, progargyl, and fused aryl;
- if $Z^1$ is C, then $R^3$ is selected from the group consisting of H, $C_1$–$C_6$ alkyl, allyl, arenxyl, propargyl, $C_1$–$C_6$ O-alkyl, OH, halogen, and fused aryl;
- if $Z^1$ is N, then $R^3$ is absent;
- $R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and
- if $Z^2$ is C, then $R^5$ is selected from the group consisting of H, $C_1$–$C_6$ alkyl, allyl, arenxyl, propargyl, $C_1$–$C_6$ O-alkyl, OH, halogen, and fused aryl;
- if $Z^2$ is N, then $R^5$ is absent; and
- $S^-$ is a counter ion.

8. A method for converting an onium salt of a taxo-diterpenoid-$C^n$,2-O-aza-arene derivative into a taxo-diterpeniod:protein conjugate, the method employing the following step:

contacting the onium salt of the taxo-diterpenoid-$C^n$,2-O-aza-arene derivative with a serum protein for displacing 2-O-aza-arene and conjugating the taxo-diterpeniod with the serum protein to produce the taxo-diterpenoid:protein conjugate, wherein the onium salt of the taxo-diterpenoid-$C^n$,2-O-aza-arene derivative produced being represented by the following formula:

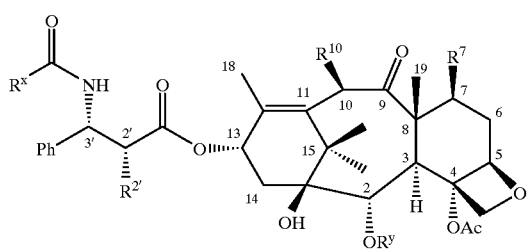

wherein:
- $C^n$ is selected from the group consisting of $C^7$ and $C^{2'}$;
- $R^x$ is selected from the group consisting of Ph and tBuO;
- $R^{10}$ is selected from the group consisting of OAc and OH;
- $R^y$ is a C-2 substituent selected from the following structures:

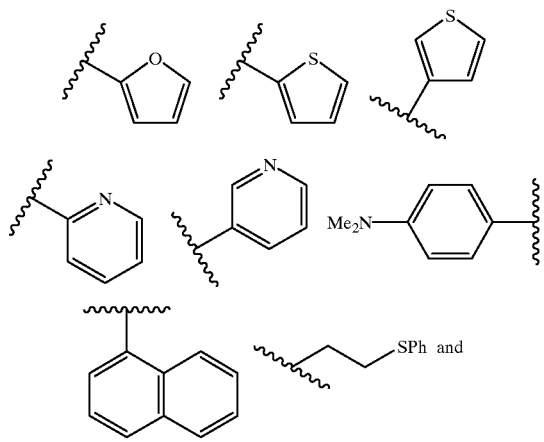

$R^{2'}$ and $R^7$ are each selected from the group consisting of OH and an onium salt of a 2-O-aza-arene, with the proviso that at least one of $R^{2'}$ and $R^7$ is said onium salt of the 2-O-aza-arene, said onium salt of the 2-O-aza-arene being selected from the group consisting of onium salt I and onium salt II represented by the following formulas:

Onium Salt I

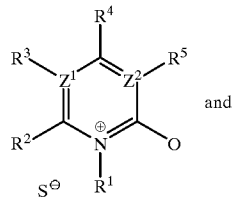

and

Onium Salt II

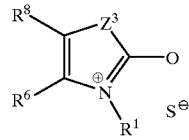

wherein:
- $R^0$ is oxygen and is bonded to $C^n$;
- $Z^1$ and $Z^2$ are each selected from the group consisting of C and N;
- $Z^3$ is selected from the group consisting of S and O;
- $R^1$ is selected from the group consisting of $C_1$–$C_6$ alkyl, allyl, arenxyl, progargyl, and fused aryl;
- $R^2$ and $R^6$ are each selected from the group consisting of H, $C_1$–$C_6$ alkyl, allyl, arenxyl, propargyl, and fused aryl;

if $Z^1$ is C, then $R^3$ is selected from the group consisting of H, $C^1$–$C^6$ alkyl, allyl, arenxyl, progargyl, $C_1$–$C_6$ O-alkyl, OH, halogen, and fused aryl;

if $Z^1$ is N, then $R^3$ is absent;

$R^4$ and $R^8$ are each selected from the group consisting of H, $C_1$–$C_6$ alkyl, allyl, arenxyl, propargyl, $C_1$–$C_6$ O-alkyl, OH, halogen, and fused aryl; and $Z^2$ is C, then $R^5$ is selected from the group consisting of H, $C_1$–$C_6$ alkyl, allyl, arenxyl, progargyl, $C_1$–$C_6$ O-alkyl, OH, halogen, and fused aryl;

if $Z^2$ is N, then $R^5$ is absent; and $S^-$ is a counter ion.

* * * * *

Disclaimer

6,252,094 B1 — Nicolaou et al., La Jolla, CA (US). CHEMICAL SWITCHING OF TAXO-DITERPENOIDS BETWEEN LOW SOLUBILITY ACTIVE FORMS AND HIGH SOLUBILITY INACTIVE FORMS. Patent dated June 26, 2001, Disclaimer filed August 9, 2004, by the Assignee, The Scripps Research Institute.

This patent is subject to a terminal disclaimer.

*(Official Gazette June 14, 2005)*